(12) United States Patent
Lee et al.

(10) Patent No.: US 9,139,602 B2
(45) Date of Patent: Sep. 22, 2015

(54) FUSED RING COMPOUND AND ORGANIC LIGHT-EMITTING DEVICE INCLUDING THE SAME

(71) Applicant: SAMSUNG DISPLAY CO., LTD., Yongin-si, Gyeonggi-do (KR)

(72) Inventors: Jung-Sub Lee, Yongin-si (KR); Seung-Gak Yang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 399 days.

(21) Appl. No.: 13/673,982

(22) Filed: Nov. 9, 2012

(65) Prior Publication Data

US 2014/0001442 A1    Jan. 2, 2014

(30) Foreign Application Priority Data

Jun. 27, 2012    (KR) ................. 10-2012-0069472

(51) Int. Cl.
| | |
|---|---|
| H01L 51/50 | (2006.01) |
| C07F 7/10 | (2006.01) |
| C07D 491/048 | (2006.01) |
| C07D 495/04 | (2006.01) |
| H01L 51/00 | (2006.01) |
| C07F 7/08 | (2006.01) |

(52) U.S. Cl.
CPC .............. *C07F 7/10* (2013.01); *C07D 491/048* (2013.01); *C07D 495/04* (2013.01); *C07F 7/0816* (2013.01); *H01L 51/0032* (2013.01); *H01L 51/0067* (2013.01); *H01L 51/0071* (2013.01); *H01L 51/0081* (2013.01); *H01L 51/0085* (2013.01); *H01L 51/5016* (2013.01); *H01L 51/5056* (2013.01); *H01L 51/5072* (2013.01); *H01L 51/5088* (2013.01); *H01L 51/5092* (2013.01)

(58) Field of Classification Search
CPC    C07D 491/048; C07D 495/04; C07F 7/0816; C07F 7/10; H01L 51/0032; H01L 51/0067; H01L 51/0071; H01L 51/0081; H01L 51/0085; H01L 51/5016; H01L 51/5056; H01L 51/5072; H01L 51/5088; H01L 51/5092; H01L 51/50; H01L 51/54; C09K 11/06; H05B 33/14

See application file for complete search history.

(56) References Cited

U.S. PATENT DOCUMENTS

| | | |
|---|---|---|
| 7,727,640 B2 | 6/2010 | Tada et al. |
| 2010/0044695 A1 | 2/2010 | Kai et al. |
| 2012/0018717 A1 | 1/2012 | Kim et al. |

FOREIGN PATENT DOCUMENTS

| | | |
|---|---|---|
| JP | 2005-129310 A | 5/2005 |
| JP | 2006-210884 A | 8/2006 |
| KR | 10-2008-0080306 | 9/2008 |
| KR | 10-2011-0079401 A | 7/2011 |
| KR | 10-2011-0092264 | 8/2011 |
| WO | WO 2007/069569 A1 | 6/2007 |
| WO | WO 2008/123189 A1 | 10/2008 |

*Primary Examiner* — Dawn Garrett
(74) *Attorney, Agent, or Firm* — Christie, Parker & Hale, LLP

(57) ABSTRACT

A fused ring compound represented by Formula 1:

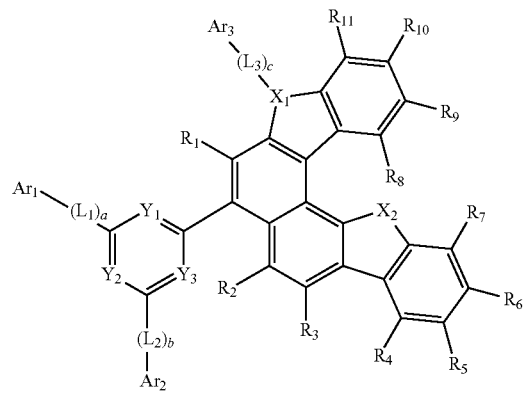

Formula 1

In Formula 1, $X_1$, $X_2$, $Y_1$ to $Y_6$, $Ar_1$ to $Ar_3$, $R_1$ to $R_{11}$, $L_1$ to $L_3$, a, b, and c are as defined in the specification.

21 Claims, 1 Drawing Sheet

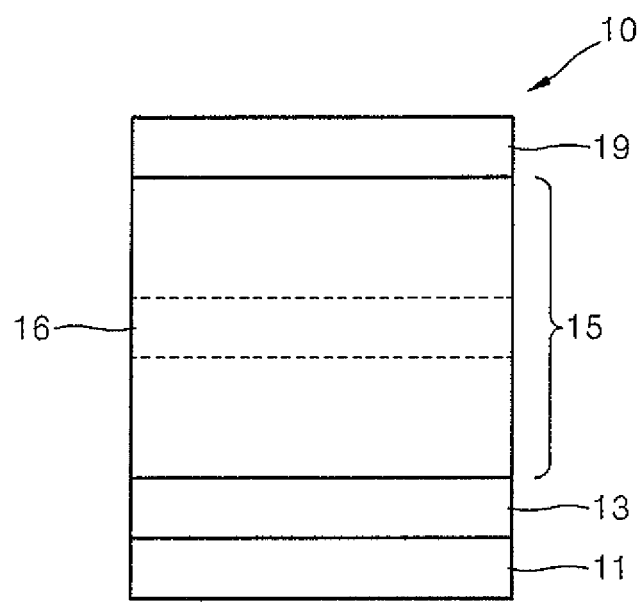

FUSED RING COMPOUND AND ORGANIC LIGHT-EMITTING DEVICE INCLUDING THE SAME

CROSS-REFERENCE TO RELATED PATENT APPLICATION

This application claims priority to and the benefit of Korean Patent Application No. 10-2012-0069472, filed on Jun. 27, 2012, in the Korean Intellectual Property Office, the entire content of which is incorporated herein by reference.

BACKGROUND

1. Field

The following description relates to a fused ring compound and an organic light-emitting device, and more particularly, to a novel fused ring compound, an organic light-emitting device with improved lifetime (lifespan) that includes an organic layer formed using the fused ring compound, and an organic light-emitting display apparatus including the organic light-emitting device.

2. Description of the Related Art

Organic light-emitting devices (OLEDs), which are self-emitting devices, have advantages such as wide viewing angles, excellent contrast, quick response, high brightness, excellent driving voltage characteristics, and can provide multicolored images. Due to these characteristics OLEDs have been receiving growing attention.

An existing organic light-emitting device has a structure that includes an anode disposed on a substrate, a hole transport layer (HTL), an emission layer, an electron transport layer (ETL) and a cathode that are sequentially disposed upon one another. The HTL, the EML, and the ETL are normally formed of organic compounds. When a voltage is applied between the anode and the cathode, holes injected from the anode move to the EML via the HTL, and electrons injected from the cathode move to the EML via the ETL. The holes and electrons (carriers) recombine in the EML to generate excitons. When the excitons drop from an excited state to a ground state, light is emitted.

A major factor affecting luminescent efficiency of an organic light-emitting device is its luminescent material. Fluorescent materials are widely used as light-emitting materials, and there is also an increasing use of phosphorescent materials that is capable of improving light-emitting efficiency up to four times based on theoretical electroluminescence mechanisms.

To lower consumption power of an organic light-emitting device, power efficiency of the organic light-emitting device may be increased. According to the relationship "power efficiency=(π/voltage)×current efficiency", reducing the voltage may lead to high power efficiency. In practice, an organic light-emitting device using a common phosphorescent (host) material such as BAlq or CBP may have a considerably higher current efficiency, but also have a higher driving voltage, as compared with an organic light-emitting device using a fluorescent material, and thus is not advantageous in terms of power efficiency.

Organic light-emitting devices using such an existing host material are also not satisfactory in terms of lifetime, and thus there is a need for development of a more stable host material with improved characteristics.

SUMMARY

An aspect of an embodiment of the present invention is directed toward a novel fused ring compound with a strong skeleton structure that is distinguishable from existing light-emitting materials.

An aspect of an embodiment of the present invention is directed toward an organic light-emitting device including an organic layer formed using the fused ring compound, wherein the organic light-emitting device has high luminescent efficiency, long lifetime, and appropriate color coordinates.

An aspect of an embodiment of the present invention is also directed toward a high-efficiency, long lifetime organic light-emitting display apparatus including the organic light-emitting device.

According to an embodiment of the present invention, there is provided a fused ring compound represented by Formula 1 below:

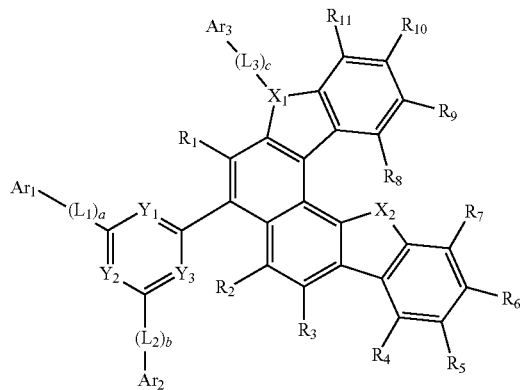

Formula 1 wherein, in Formula 1, $X_1$ is a nitrogen atom (N);

$X_2$ is one of S, O, $Si(R_{12})(R_{13})$, and $N(R_{14})$;

$Y_1$ to $Y_3$ are each independently one of C and N, wherein at least one of $Y_1$ to $Y_3$ is N;

$Ar_1$ to $Ar_3$ are each independently selected from among a substituted or unsubstituted $C_6$-$C_{40}$ aryl group, a substituted or unsubstituted $C_6$-$C_{40}$ arylalkyl, a substituted or unsubstituted $C_6$-$C_{40}$ aryloxy group, a substituted or unsubstituted $C_6$-$C_{40}$ arylthio group, a substituted or unsubstituted $C_6$-$C_{40}$ arylamino group, and a substituted or unsubstituted $C_2$-$C_{40}$ heteroaryl group;

$R_1$ to $R_{14}$ are each independently a hydrogen atom, a deuterium atom, a halogen atom, a hydroxyl group, a cyano group, a nitro group, an amino group, a carboxyl group, a substituted or unsubstituted $C_1$-$C_{40}$ alkyl group, a substituted or unsubstituted $C_1$-$C_{40}$ alkoxy group, a substituted or unsubstituted $C_2$-$C_{40}$ alkenyl group, a substituted or unsubstituted $C_2$-$C_{40}$ alkynyl group, a substituted or unsubstituted $C_3$-$C_{40}$ cycloalkyl group, a substituted or unsubstituted $C_3$-$C_{40}$ cycloalkenyl group, a substituted or unsubstituted $C_6$-$C_{40}$ aryl group, a substituted or unsubstituted $C_6$-$C_{40}$ arylalkyl group, a substituted or unsubstituted $C_6$-$C_{40}$ aryloxy group, a substituted or unsubstituted $C_6$-$C_{40}$ arylthio group, a substituted or unsubstituted $C_6$-$C_{40}$ arylamino group, and a substituted or unsubstituted $C_2$-$C_{40}$ heteroaryl group, wherein at least two adjacent groups of $R_1$ to $R_{14}$ are optionally fused;

$L_1$ to $L_3$ are each independently a substituted or unsubstituted $C_6$-$C_{40}$ arylene group; and a, b and c are each independently an integer from 0 to 3.

According to another embodiment of the present invention, there is provided an organic light-emitting device including a first electrode, a second electrode disposed opposite to the first electrode, and an organic layer disposed between the first electrode and the second electrode, the organic layer including the above-described fused ring compound.

The organic layer may include at least one of a hole injection layer, a hole transport layer, a functional layer having both hole injection and hole transport capabilities, a buffer layer, an emission layer, a hole blocking layer, an electron transport layer, an electron injection layer, and a functional layer having both electron injection and electron transport capabilities.

The organic layer may include at least one of a hole injection layer, a hole transport layer, and a functional layer having both hole injection and hole transport capabilities, and at least one of the hole injection layer, the hole transport layer, and the functional layer having both hole injection and hole transport capabilities comprises the fused ring compound.

At least one of the hole injection layer, the hole transport layer, and the functional layer having both hole injection and hole transport capabilities may further include a charge-generating material, and the charge-generating material may be at least one of a quinine derivative, a metal oxide, and a cyano group-containing compound.

The organic layer may include at least one of an electron injection layer, an electron transport layer, and a functional layer having both electron injection and electron transport capabilities, and at least one of the electron injection layer, the electron transport layer, and the functional layer having both electron injection and electron transport capabilities may include the fused ring compound.

The organic layer may include an emission layer, and the emission layer may include the fused ring compound.

The fused ring compound may serve as a phosphorescent host.

The organic layer may include an emission layer, and at least one of an electron injection layer, an electron transport layer and a functional layer having both electron injection and electron transport capabilities; and the emission layer may include an arylamine compound.

According to another embodiment of the present invention, there is provided an organic light-emitting display device including: a transistor including a source, a drain, a gate, and an active layer; and the above-described organic light-emitting device, wherein one of the source and the drain of the transistor is electrically connected to the first electrode of the organic light-emitting device.

BRIEF DESCRIPTION OF THE DRAWING

The above and other features and advantages of the present invention will become more apparent by describing in detail exemplary embodiments thereof with reference to the attached drawing in which:

The drawing is a schematic diagram of the structure of an organic light-emitting device according to an embodiment of the present invention.

DETAILED DESCRIPTION

As used herein, the term "and/or" includes any and all combinations of one or more of the associated listed items. Expressions such as "at least one of," when preceding a list of elements, modify the entire list of elements and do not modify the individual elements of the list.

According to an aspect of the present invention, there is provided a fused ring compound represented by Formula 1 below.

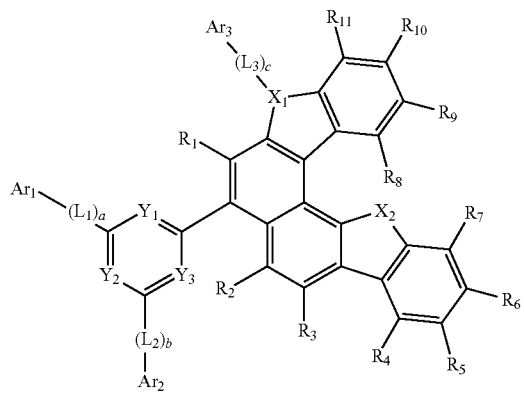

Formula 1 wherein, in Formula 1,
$X_1$ is a nitrogen atom (N);
$X_2$ is one of S, O, $Si(R_{12})(R_{13})$, and $N(R_{14})$;
$Y_1$ to $Y_3$ are each independently one of C (a carbon atom) and N, wherein at least one of $Y_1$ to $Y_3$ is N;
$A_1$ to $Ar_3$ are each independently selected from among a substituted or unsubstituted $C_6$-$C_{40}$ aryl group, a substituted or unsubstituted $C_6$-$C_{40}$ arylalkyl, a substituted or unsubstituted $C_6$-$C_{40}$ aryloxy group, a substituted or unsubstituted $C_6$-$C_{40}$ arylthio group, a substituted or unsubstituted $C_6$-$C_{40}$ arylamino group, and a substituted or unsubstituted $C_2$-$C_{40}$ heteroaryl group;
$R_1$ to $R_{14}$ are each independently a hydrogen atom, a deuterium atom, a halogen atom, a hydroxyl group, a cyano group, a nitro group, an amino group, a carboxyl group, a substituted or unsubstituted $C_1$-$C_{40}$ alkyl group, a substituted or unsubstituted $C_1$-$C_{40}$ alkoxy group, a substituted or unsubstituted $C_2$-$C_{40}$ alkenyl group, a substituted or unsubstituted $C_2$-$C_{40}$ alkynyl group, a substituted or unsubstituted $C_3$-$C_{40}$ cycloalkyl group, a substituted or unsubstituted $C_3$-$C_{40}$ cycloalkenyl group, a substituted or unsubstituted $C_6$-$C_{40}$ aryl group, a substituted or unsubstituted $C_6$-$C_{40}$ arylalkyl group, a substituted or unsubstituted $C_6$-$C_{40}$ aryloxy group, a substituted or unsubstituted $C_6$-$C_{40}$ arylthio group, a substituted or unsubstituted $C_6$-$C_{40}$ arylamino group, and a substituted or unsubstituted $C_2$-$C_{40}$ heteroaryl group, wherein at least two adjacent groups of $R_1$ to $R_{14}$ are optionally fused;
$L_1$ to $L_3$ are each independently a substituted or unsubstituted $C_6$-$C_{40}$ arylene group; and
a, b and c are each independently an integer from 0 to 3.

The fused ring compound represented by Formula 1 above may have a fused structure of intramolecular carbazols and heteroaromatic groups, or a fused structure of intramolecular carbazole and silol group.

In Formula 1, $X_1$ is a nitrogen atom (N), and a moiety with $X_1$ represents a carbazole group. In Formula 1, $X_2$ is one of S, O, $N(R_{14})$, and $Si(R_{12})(R_{13})$, and a moiety with $X_2$ represents a heteroaromatic group consisting of a hetero atom, such as S, O, or N, and a carbon atom, or a silol group consisting of a Si atom and a carbon atom. In the fused ring compound of Formula 1, a fused ring moiety including $X_1$ and $X_2$ may have a fused structure of a carbazole group and a heteroaromatic group, or a fused structure of a carbazole group and a silol group.

The fused ring compound of Formula 1 may have an intramolecular hetero ring with nitrogen.

In Formula 1, $Y_1$ to $Y_3$ are each independently one of C and N, wherein at least one of $Y_1$ to $Y_3$ is N. In Formula 1, a moiety including $Y_1$ to $Y_3$ represents a hetero ring with N. That is, in the fused ring compound of Formula 1, the moiety with $Y_1$ to $Y_3$ may represent a hetero ring, such as a triazine group, a pyrimidine group, or a pyridine group.

The fused ring compound of Formula 1 above may have a rigid fused structure of intramolecular carbazols and heteroaromatic groups, or of intramolecular carbazole and silol group, and thus may have a high glass transition temperature and a high melting point. Furthermore, the fused ring compound may have improved electrical characteristics, for example, in terms of electron transfer ability, due to having an intramolecular hetero ring with N.

In Formula 1, $Ar_1$ to $Ar_3$ each represent an aromatic or heteroaromatic group as a substituent bound to a hetero ring moiety including $Y_1$ to $Y_3$; and $R_1$ to $R_{14}$ each represent a substituent bound to a fused ring moiety including $X_1$ and $X_2$. $L_1$ to $L_3$ each represent a linker that may be between a hetero ring moiety including $Ar_1$ to $Ar_3$ and a hetero ring moiety including $Y_1$ to $Y_3$; and a, b, and c represent the number of linkers. If a is 0, $-(L_1)_a-$ represents a single bond. If a is 2 or greater, a plurality of $L_1$ may be the same or different. Likewise, if b is 0, $-(L_2)_b-$ represents a single bond. If b is 2 or greater, a plurality of $L_2$ may be the same or different. If c is 0, $-(L_3)_c-$ represents a single bond. If c is 2 or greater, a plurality of $L_3$ may be the same or different.

Hereinafter, the fused ring compound of Formula 1 will be described in greater detail.

In Formula 1, $X_1$ represents a nitrogen atom. In Formula 1, a moiety including $X_1$ represents a carbazole group. If $X_1$ is S or O, synthesis of the fused ring compound of Formula 1 may be relatively difficult, so this case is excluded.

In Formula 1, $X_2$ is one of S, O, $Si(R_{12})(R_{13})$, and $N(R_{14})$;

For example, $X_2$ is one of S, O, and $Si(R_{12})(R_{13})$. In one embodiment, if $X_2$ is one of S, O, and $Si(R_{12})(R_{13})$, the fused ring compound of Formula 1 is not bulky, and thus may easily form an organic layer. If $X_2$ is a nitrogen atom (N) substituted by a phenyl group, the fused ring compound may have a bulky structure, which may not be easily packed in forming an organic layer of an organic light-emitting device using the fused ring compound.

In Formula 1, $Y_1$ to $Y_3$ are each independently one of C and N, wherein at least one of $Y_1$ to $Y_3$ is N.

For example, $Y_1$ and $Y_2$ may each be N, and $Y_3$ may be C; $Y_1$ and $Y_3$ may each be N, and $Y_2$ may be C; or $Y_2$ and $Y_3$ may each be N, and $Y_1$ may be C. In these cases, the hetero ring including $Y_1$ to $Y_3$ represents a pyrimidine group with two nitrogen atoms and four carbon atoms. In an embodiment, $Y_1$, $Y_2$ and $Y_3$ may each be N. In this case, the hetero ring including $Y_1$ to $Y_3$ represents a triazine group with three nitrogen atoms and three carbon atoms.

In Formula 1, $Y_1$ and $Y_3$ may each be N, and $Y_2$ may be C. In this case, the hetero ring including $Y_1$ to $Y_3$ represents a pyramidine group, and a carbon atom between two nitrogen atoms (a carbon atom between $Y_1$ and $Y_3$) in the pyrimidine group is bound to a fused ring including $X_1$ and $X_2$.

The fused ring compound of Formula 1 may be represented by one of Formulae 2a to 2f below

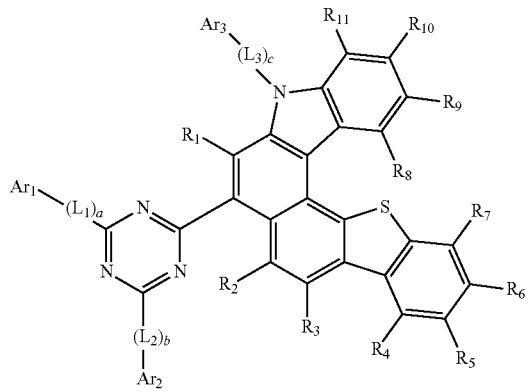

Formula 2a

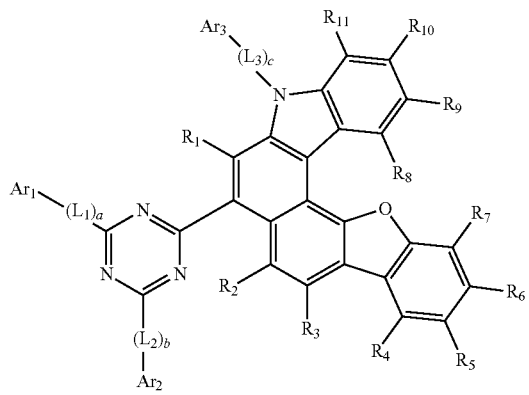

Formula 2b

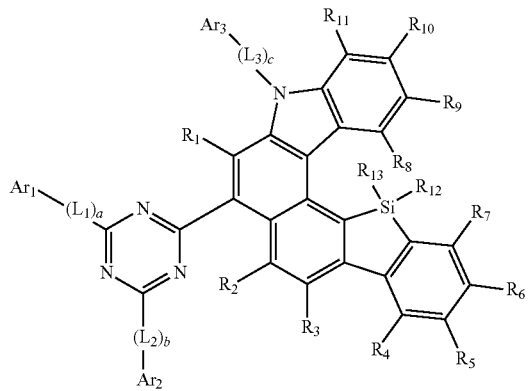

Formula 2c

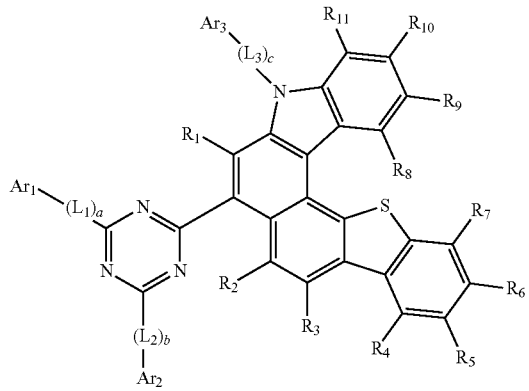

Formula 2d

Formula 2e
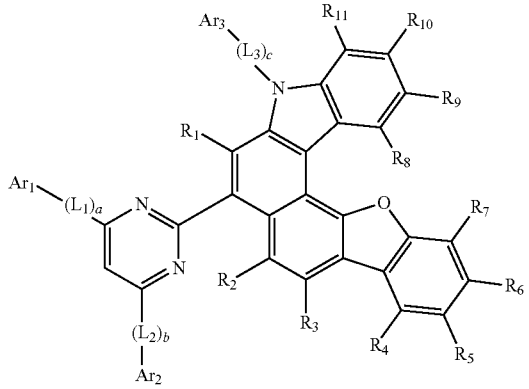

Formula 2f
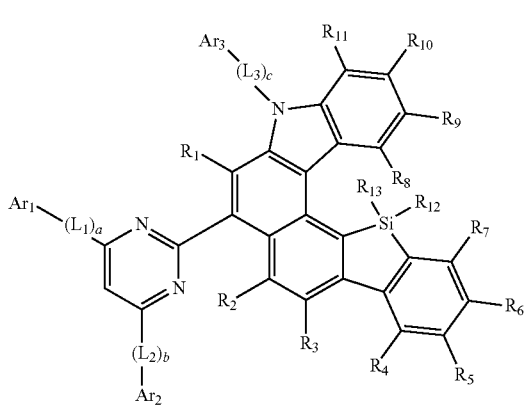

In Formulae 2a to 2f, $Ar_1$ to $Ar_3$, $R_1$ to $R_{13}$, $L_1$ to $L_3$, a, b, and c are as defined in conjunction with Formula 1.

In Formula 1, $Ar_1$ to $Ar_3$ may each be independently one of a substituted or unsubstituted $C_6$-$C_{40}$ aryl group and a substituted or unsubstituted $C_2$-$C_{40}$ heteroaryl group; $L_1$ to $L_3$ may each be independently one of a substituted or unsubstituted phenylene group, and a substituted or unsubstituted naphthylene group; and a, b and c may each be independently one of 0 and 1.

For example, $Ar_1$ to $Ar_3$ may each be independently one of a substituted or unsubstituted phenyl group, a substituted or unsubstituted naphthyl group, a substituted or unsubstituted anthryl group, a substituted or unsubstituted phenanthrenyl group, a substituted or unsubstituted phenalenyl group, a substituted or unsubstituted pyrenyl group, a substituted or unsubstituted chrysenyl group, a substituted or unsubstituted triphenylenyl group, a substituted or unsubstituted tetracenyl group, a substituted or unsubstituted tetraphenyl group, a substituted or unsubstituted benzoanthryl group, a substituted or unsubstituted benzophenanthrenyl group, a substituted or unsubstituted biphenyl group, a substituted or unsubstituted terphenyl group, a substituted or unsubstituted indenyl group, a substituted or unsubstituted fluorenyl group, a substituted or unsubstituted benzofluorenyl group, a substituted or unsubstituted fluoranthenyl group, a substituted or unsubstituted benzothiophenyl group, a substituted or unsubstituted dibenzothiophenyl group, a substituted or unsubstituted benzonaphthothiophenyl group, a substituted or unsubstituted benzofuranyl group, a substituted or unsubstituted dibenzofuranyl group, a substituted or unsubstituted benzonaphthofuranyl group, a substituted or unsubstituted benzosilolyl group, a substituted or unsubstituted dibenzosilolyl group, a substituted or unsubstituted benzonaphthosilolyl group, a substituted or unsubstituted indolyl group, a substituted or unsubstituted carbazolyl group, a substituted or unsubstituted benzocarbazolyl group, a substituted or unsubstituted quinolinyl group, a substituted or unsubstituted acridinyl group, a substituted or unsubstituted isoquinolinyl group, and a substituted or unsubstituted benzoisoquinolinyl group.

For example, $L_1$ to $L_3$ may each be independently one of a substituted or unsubstituted phenylene group, and a substituted or unsubstituted naphthalene group. For example, a, b and c may each be independently an integer of from 0 to 1;

$Ar_1$ to $Ar_3$ may each be independently one of a substituted or unsubstituted phenyl group, a substituted or unsubstituted naphthyl group, a substituted or unsubstituted anthryl group, a substituted or unsubstituted phenanthrenyl group, a substituted or unsubstituted phenalenyl group, a substituted or unsubstituted pyrenyl group, a substituted or unsubstituted chrycenyl group, a substituted or unsubstituted triphenylenyl group, a substituted or unsubstituted tetracenyl group, a substituted or unsubstituted tetraphenyl group, a substituted or unsubstituted benzoanthryl group, a substituted or unsubstituted benzophenanthrenyl group, a substituted or unsubstituted indenyl group, a substituted or unsubstituted fluorenyl group, a substituted or unsubstituted benzothiophenyl group, a substituted or unsubstituted dibenzothiophenyl group, a substituted or unsubstituted benzofuranyl group, a substituted or unsubstituted dibenzofuranyl group, a substituted or unsubstituted benzosilol group, a substituted or unsubstituted dibenzo silol group; a substituted or unsubstituted indolyl group, a substituted or unsubstituted carbazolyl group, a substituted or unsubstituted quinolinyl group, and a substituted or unsubstituted acridinyl group.

$Ar_1$ to $Ar_3$ are each independently represented by one of Formulae 3a to 3m below:

Formula 3a
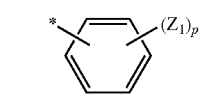

Formula 3b
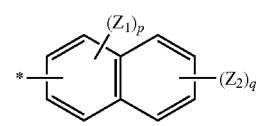

Formula 3c
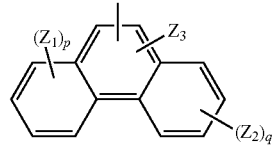

Formula 3d
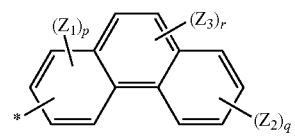

-continued

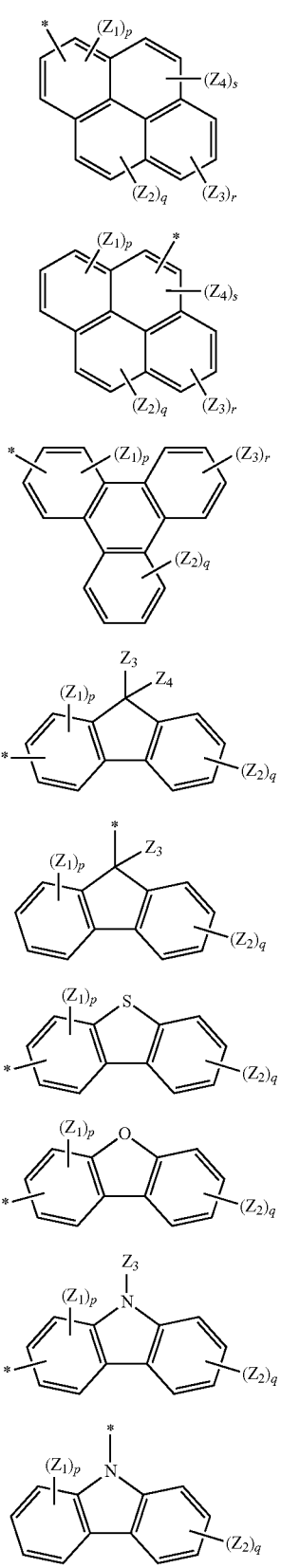

Formula 3e

Formula 3f

Formula 3g

Formula 3h

Formula 3i

Formula 3j

Formula 3k

Formula 3l

Formula 3m

In Formulae 3a to 3m, $Z_1$ to $Z_4$ may each be independently one of a hydrogen atom, a deuterium atom, a halogen atom, a hydroxyl group, a cyano group, a nitro group, an amino group, a carboxyl group, a substituted or unsubstituted methyl group, a substituted or unsubstituted ethyl group, a substituted or unsubstituted propyl group, a substituted or unsubstituted butyl group, and a substituted or unsubstituted phenyl group; and p, q, r and s may each be independently an integer from 1 to 5. The symbol * indicates a binding site with residue of the fused ring compound represented by Formula 1 excluding the moieties represented by Formulae 3a to 3m.

$Ar_1$ to $Ar_3$ may each be independently represented by one of Formulae 4a to 4j below:

Formula 4a

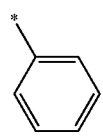

Formula 4b

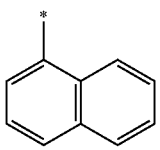

Formula 4c

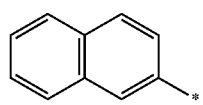

Formula 4d

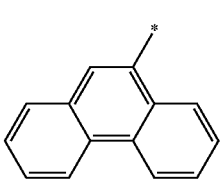

Formula 4e

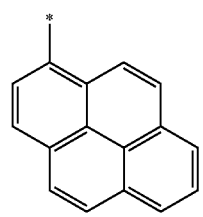

Formula 4f

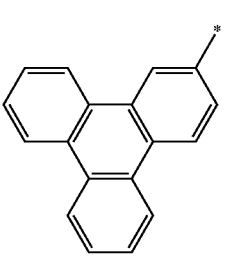

Formula 4g

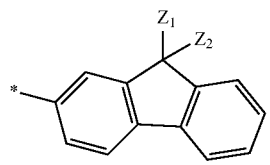

Formula 4h

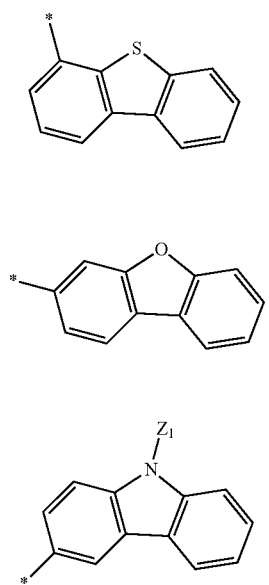

Formula 4i

Formula 4j

In Formulae 4a to 4j above, $Z_1$ and $Z_2$ may each be independently one of a hydrogen atom, a deuterium atom, a halogen atom, a hydroxyl group, a cyano group, a nitro group, an amino group, a carboxyl group, a substituted or unsubstituted methyl group, a substituted or unsubstituted ethyl group, a substituted or unsubstituted propyl group, a substituted or unsubstituted butyl group, and a substituted or unsubstituted phenyl group; and * indicates a binding site with residue of the fused ring compound represented by Formula 1 excluding the moieties represented by Formulae 3a to 3m.

In Formula 1, $R_1$ to $R_{14}$ may each be independently one of a hydrogen atom, a deuterium atom, a substituted or unsubstituted methyl group, a substituted or unsubstituted ethyl group, a substituted or unsubstituted propyl group, a substituted or unsubstituted butyl group, and a substituted or unsubstituted phenyl group.

The fused ring compound of Formula 1 may be one of Compounds 1 to 96 below, but is not limited thereto:

1

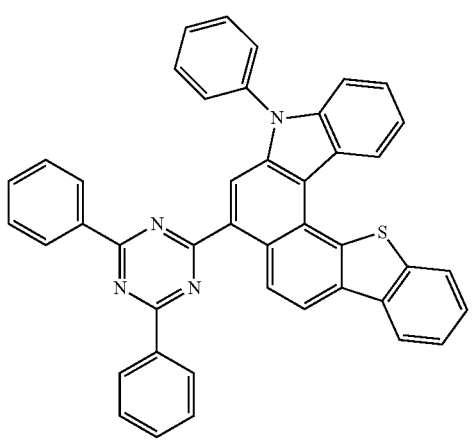

2

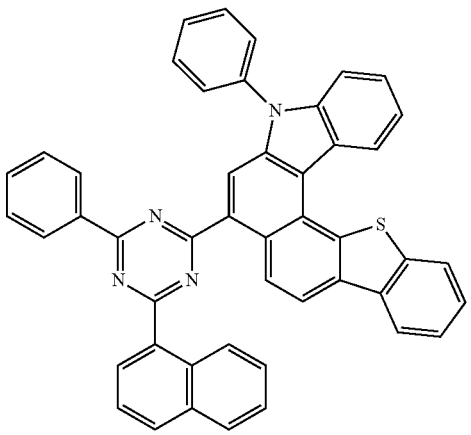

3

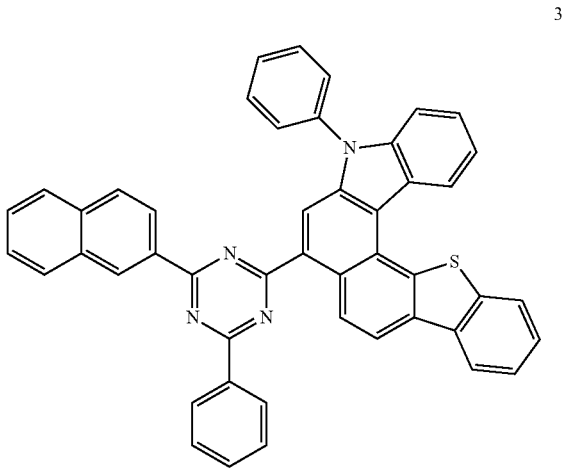

4

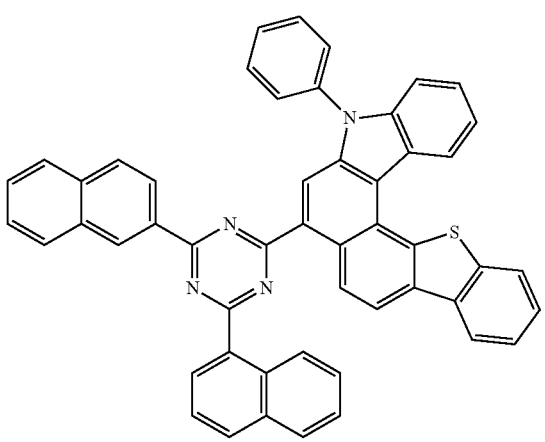

5
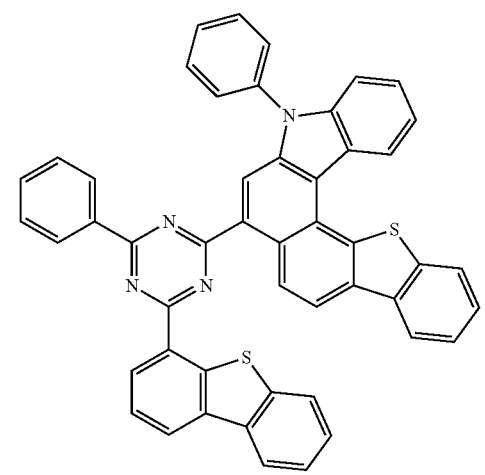
6
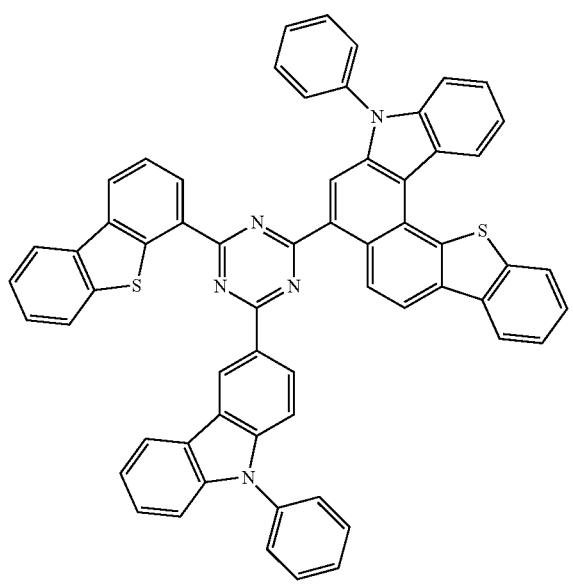
7
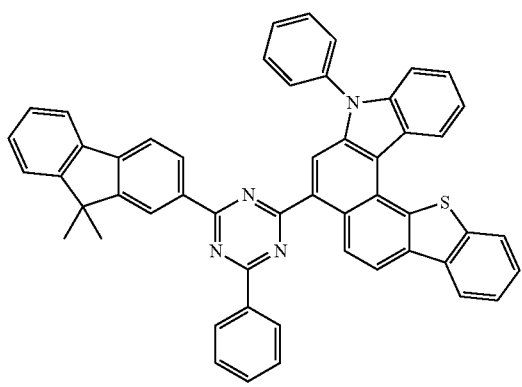
8
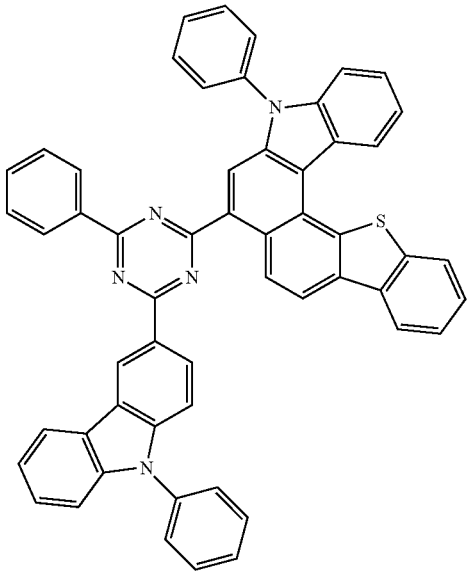
9
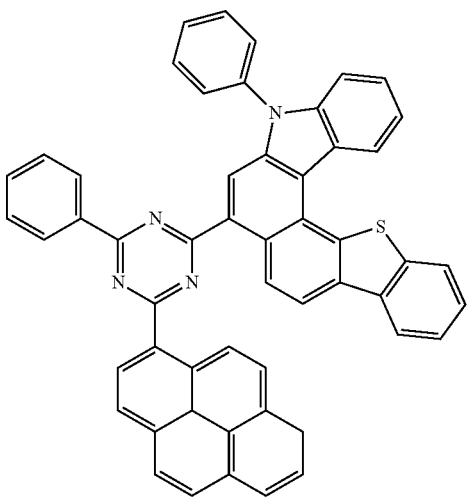
10
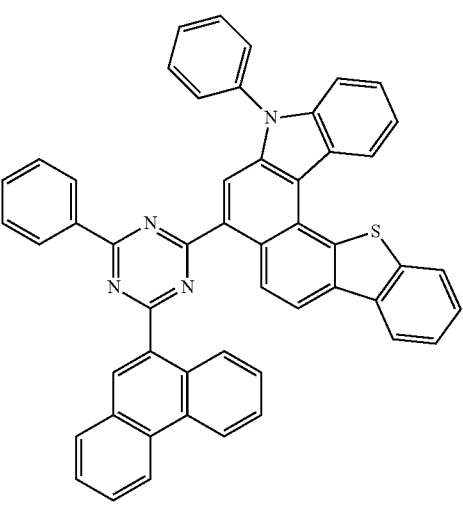

11
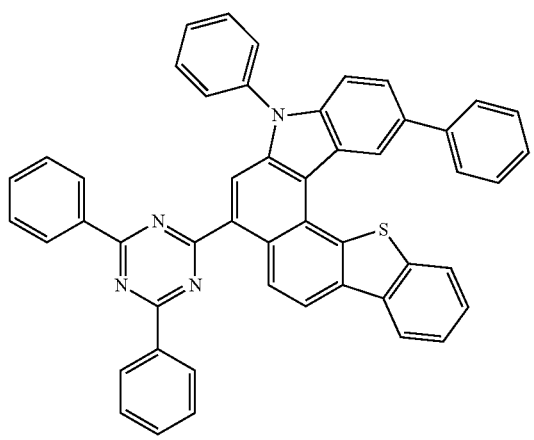
12
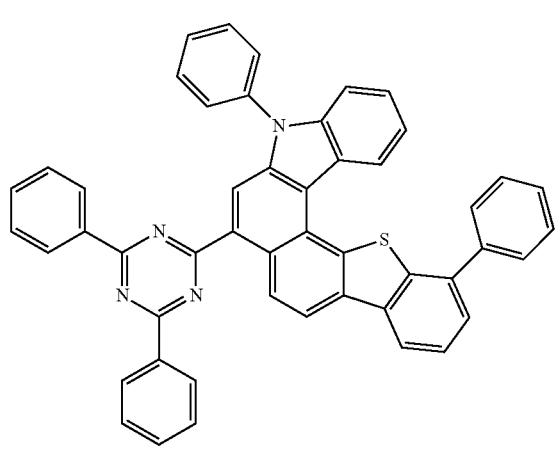
13
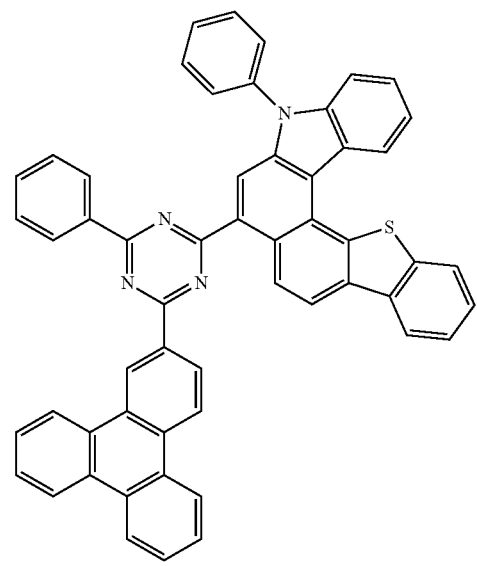
14
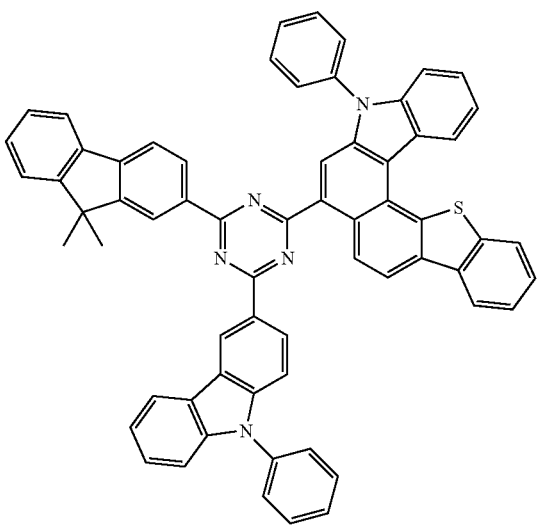
15
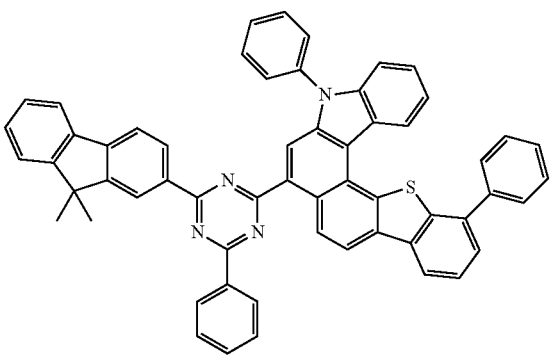
16
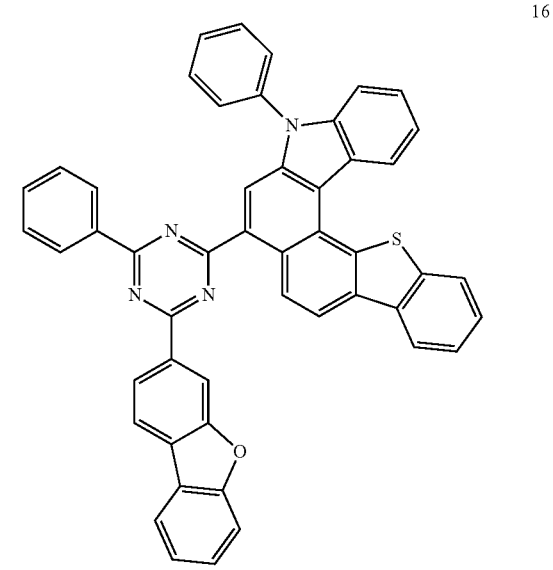

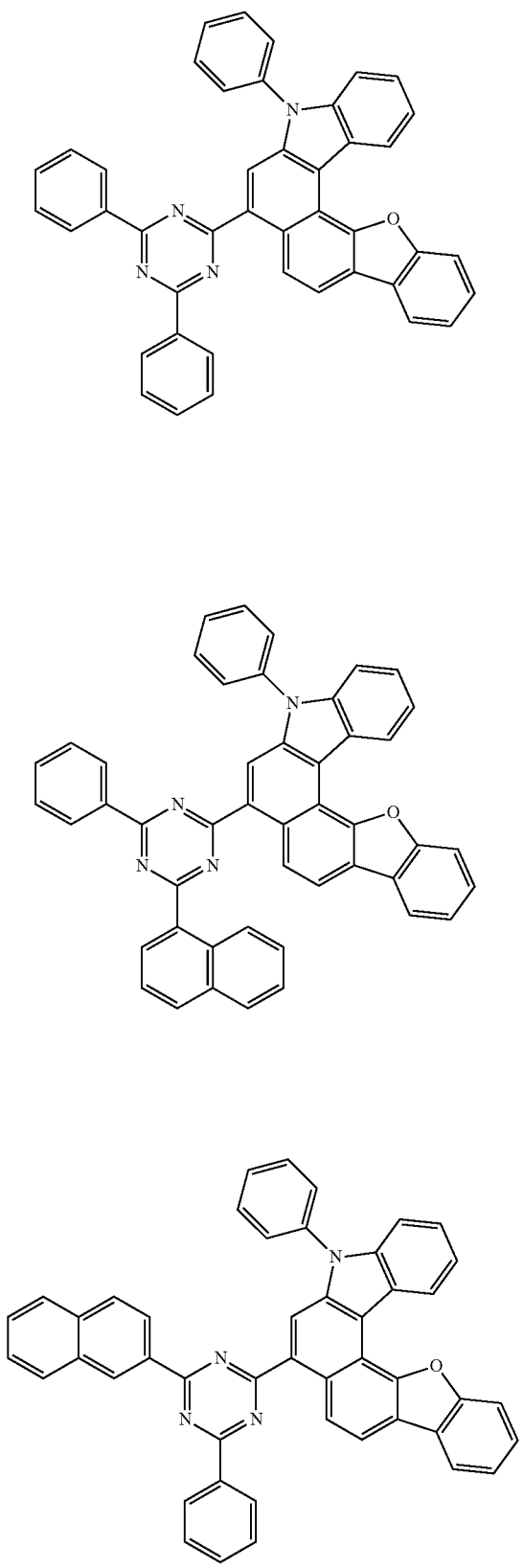
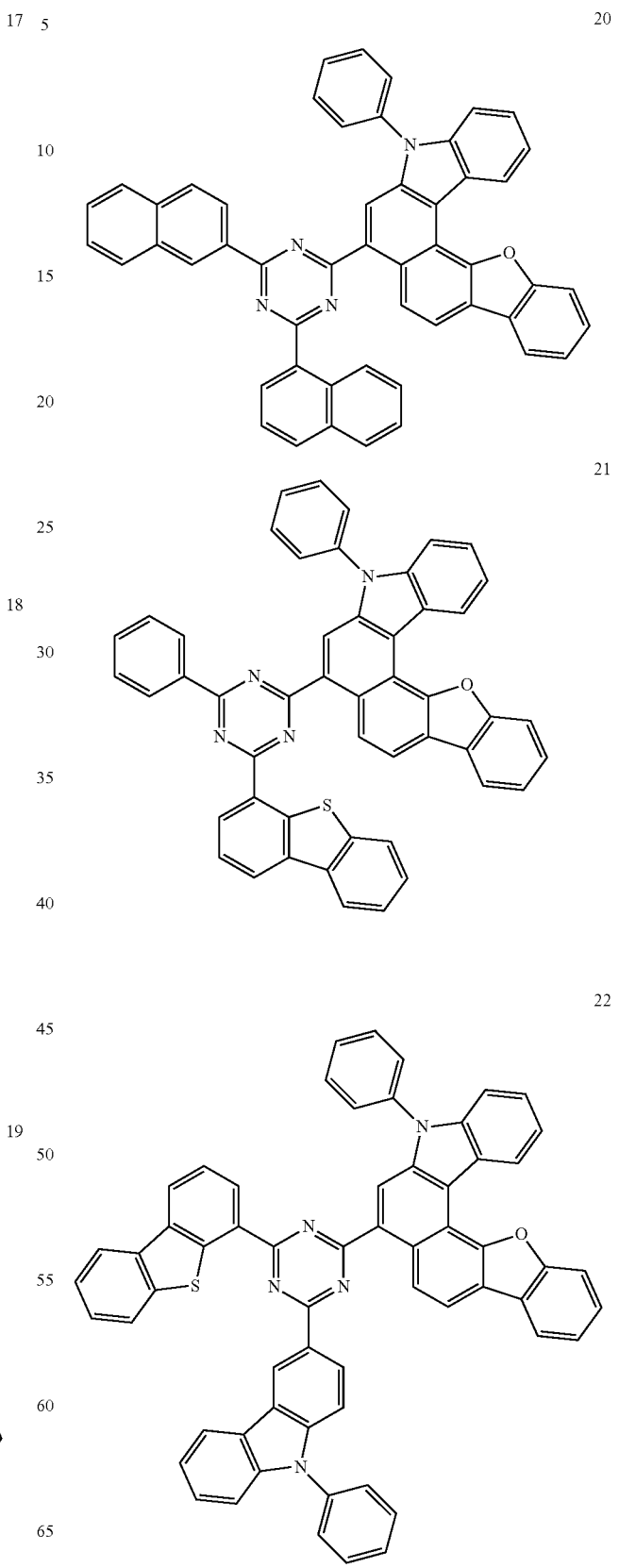

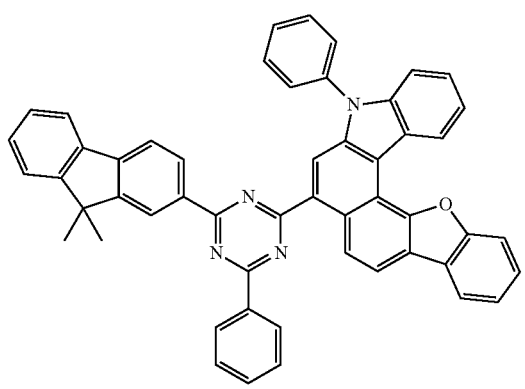
23
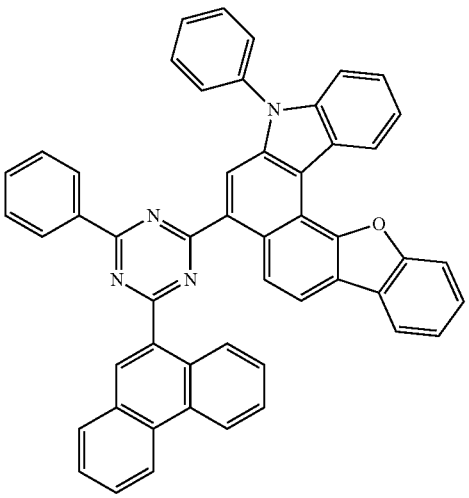
26
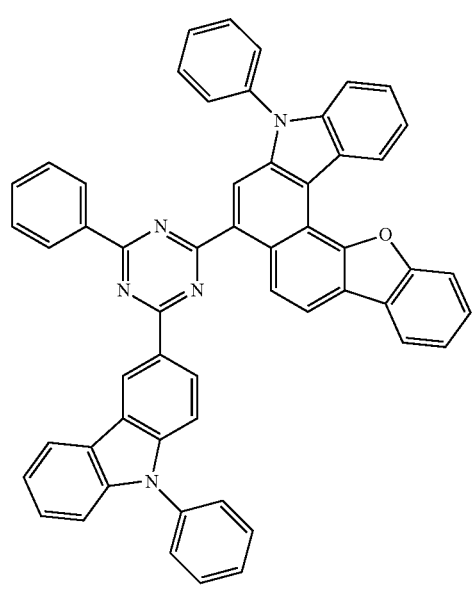
24
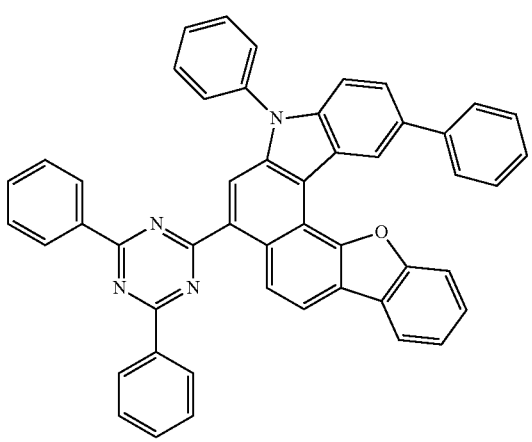
27
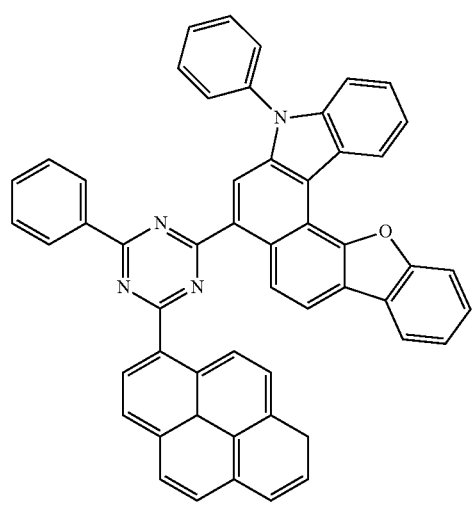
25
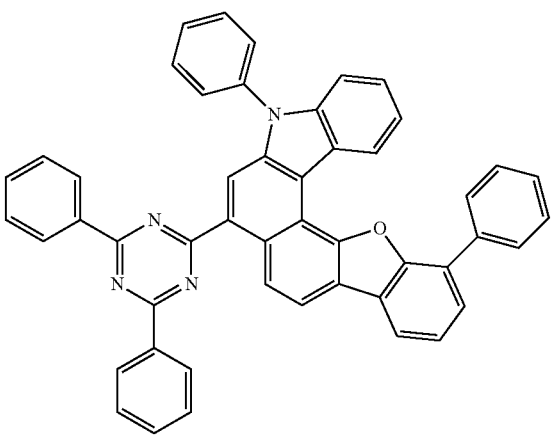
28

29
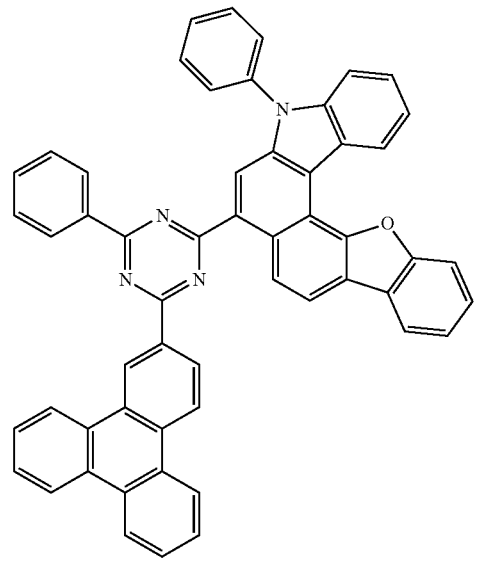
30
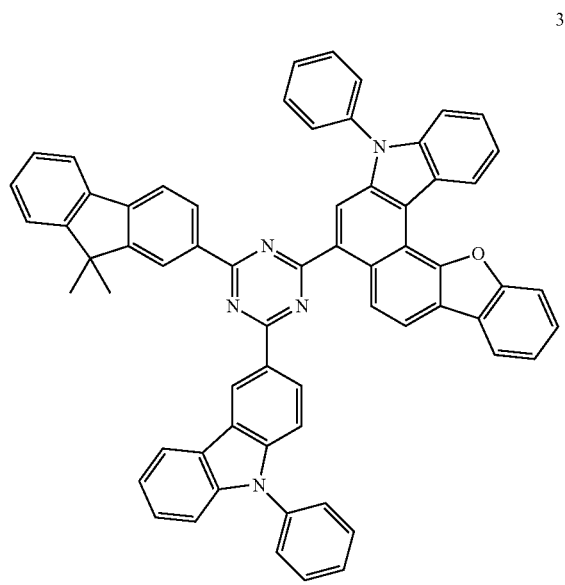
31
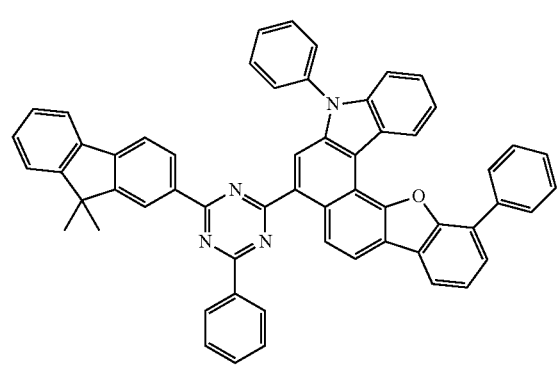
32
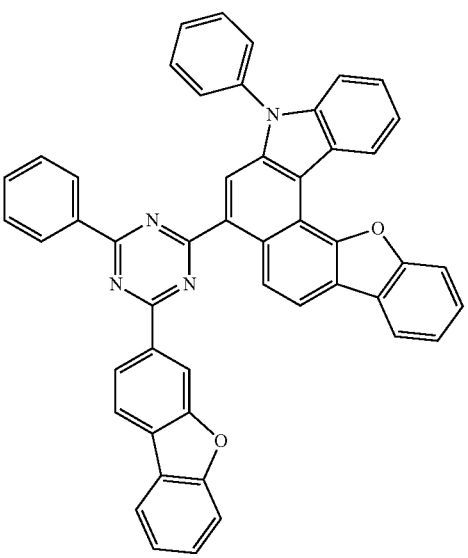
33
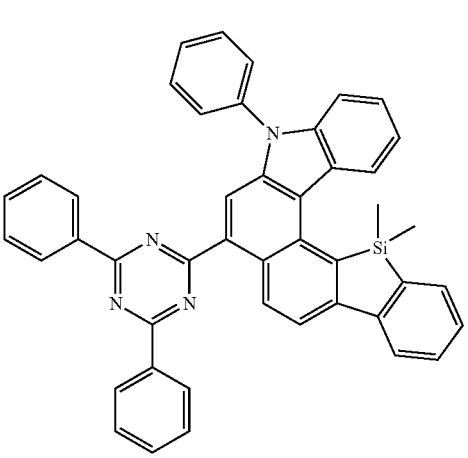
34
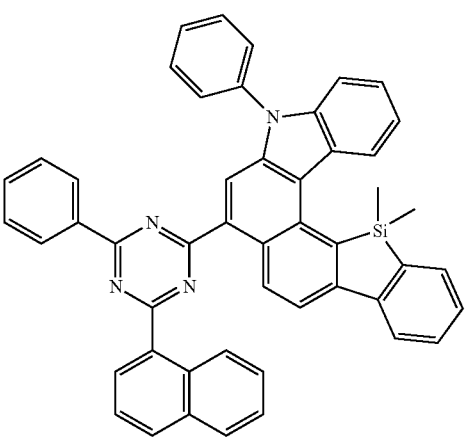

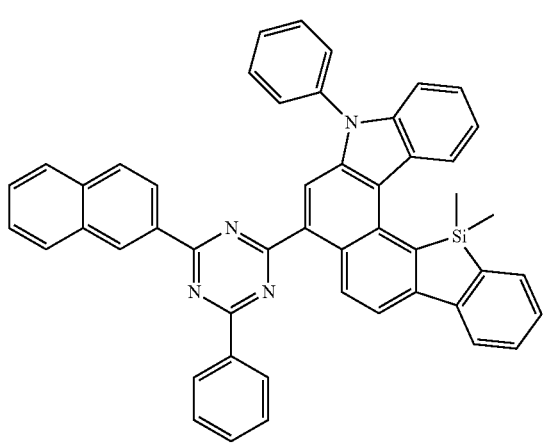
35
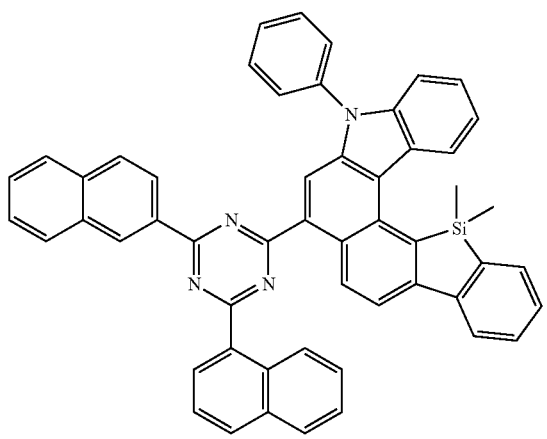
36
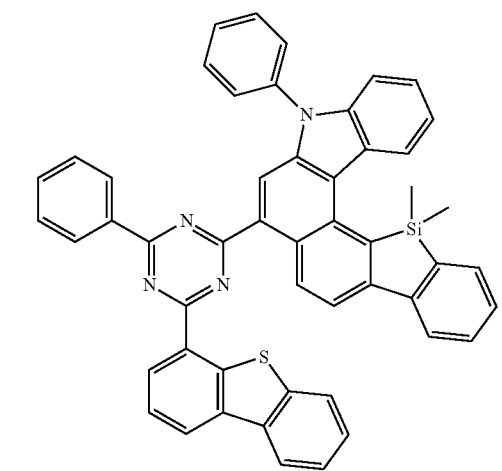
37
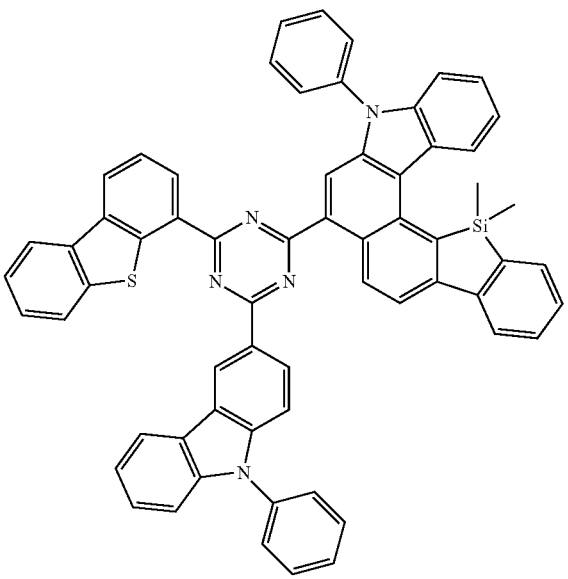
38
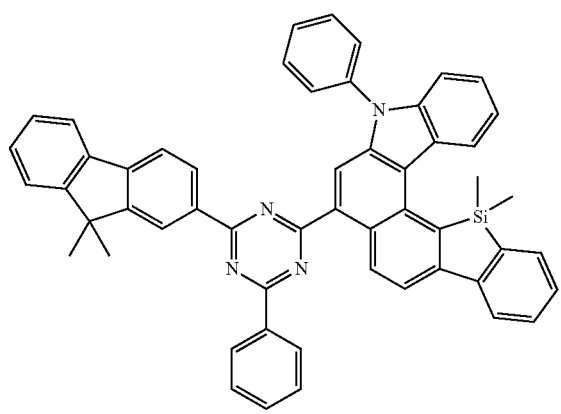
39
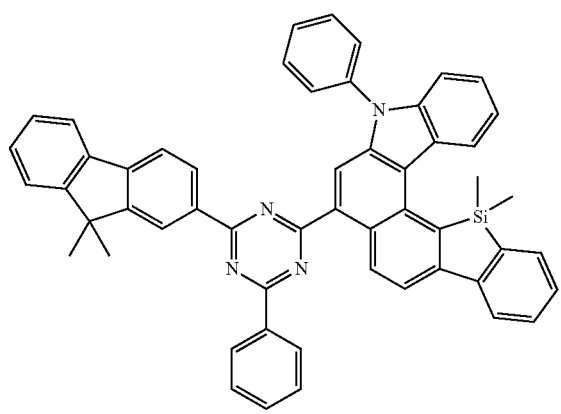
40

41
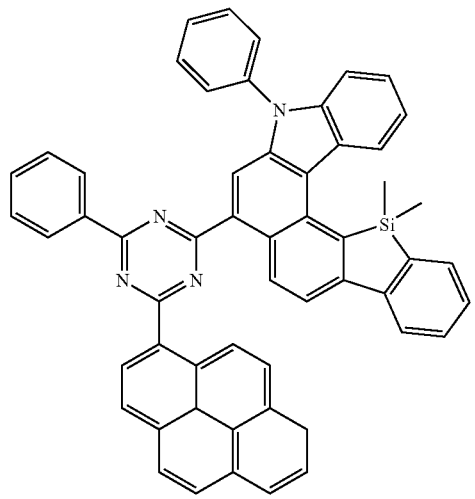
42
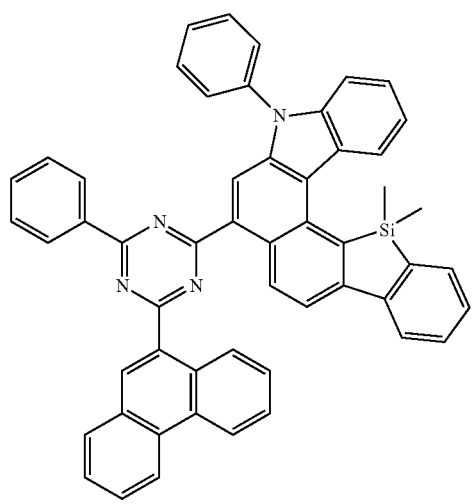
43
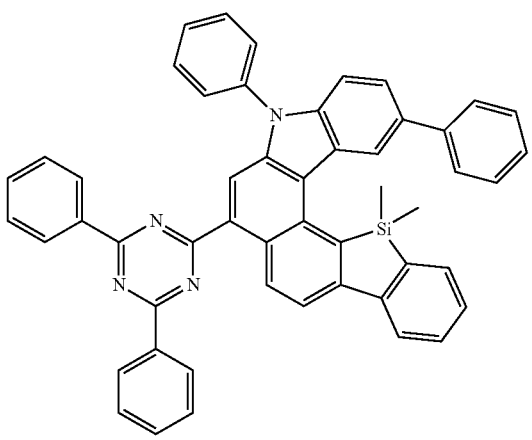
44
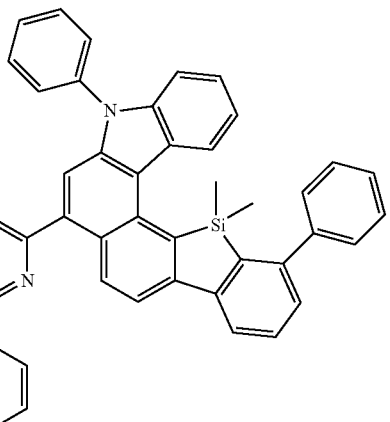
45
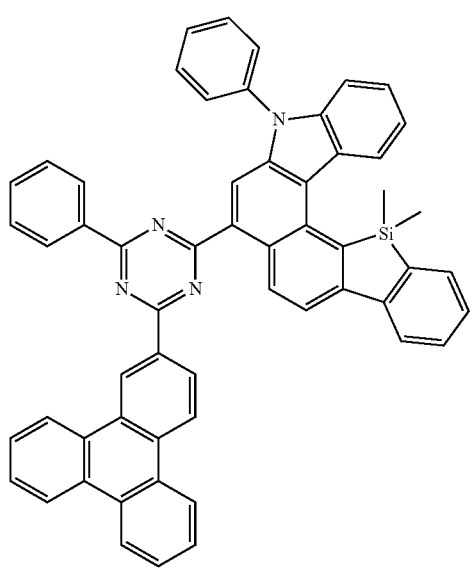
46
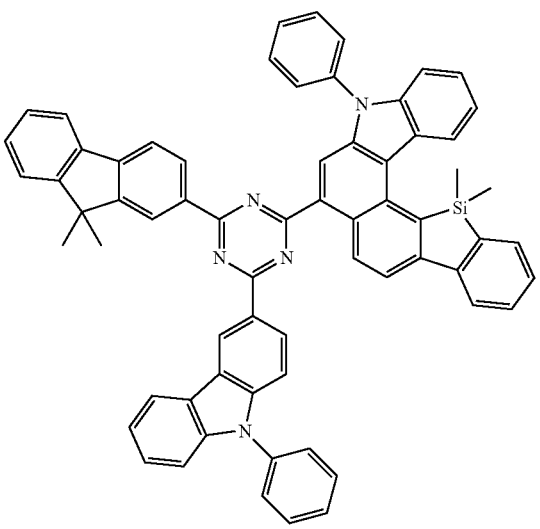

47
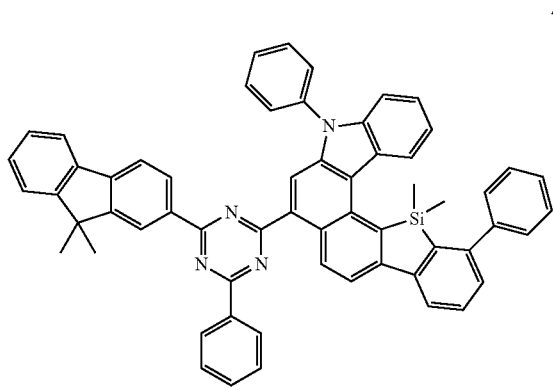
48
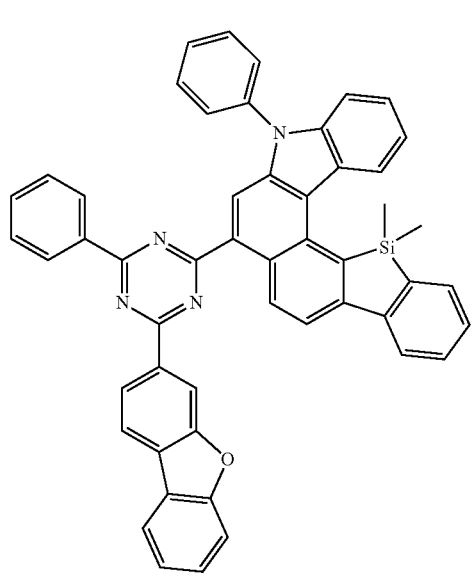
49
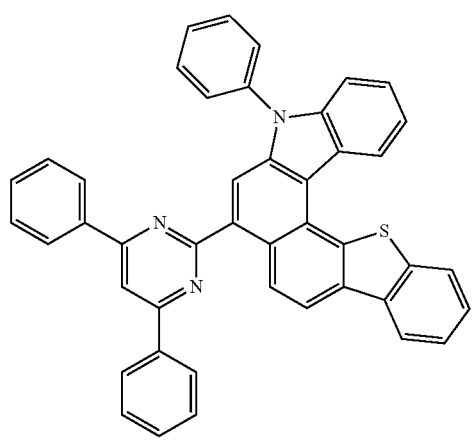
50
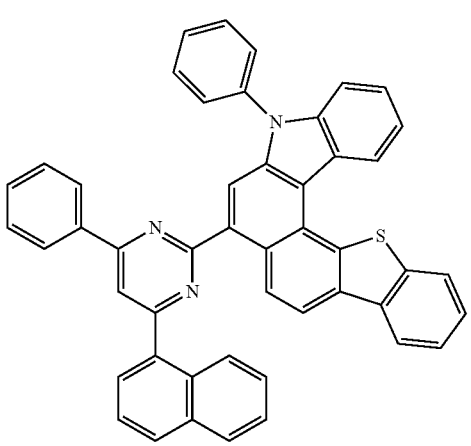
51
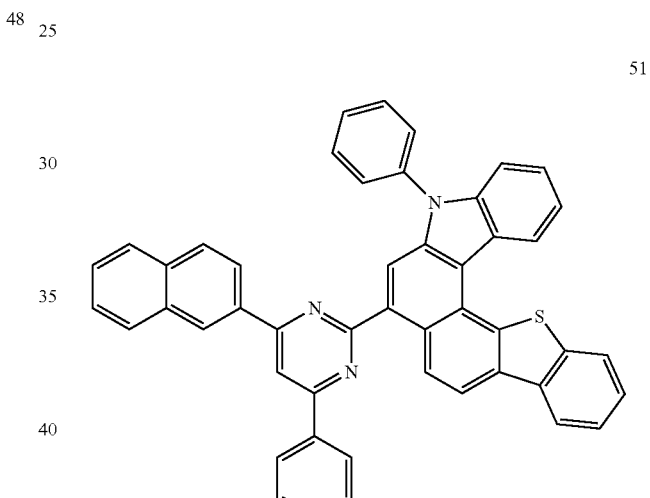
52
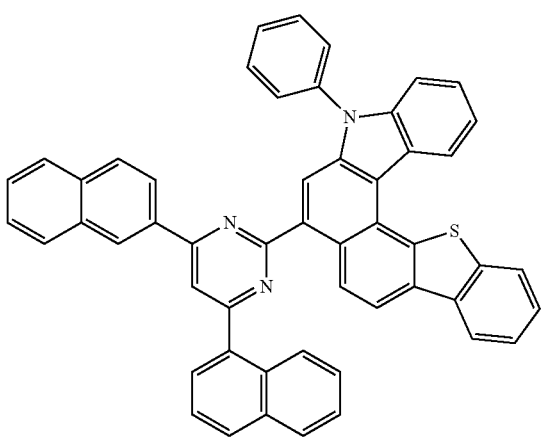

53
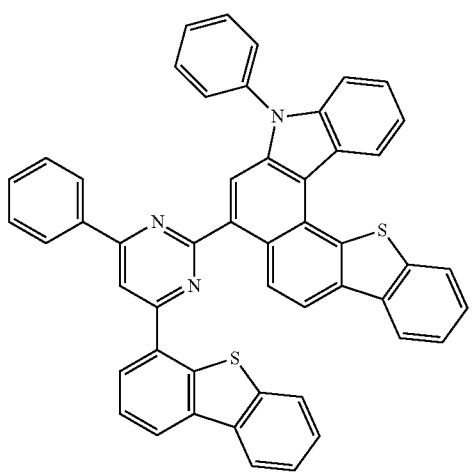
54
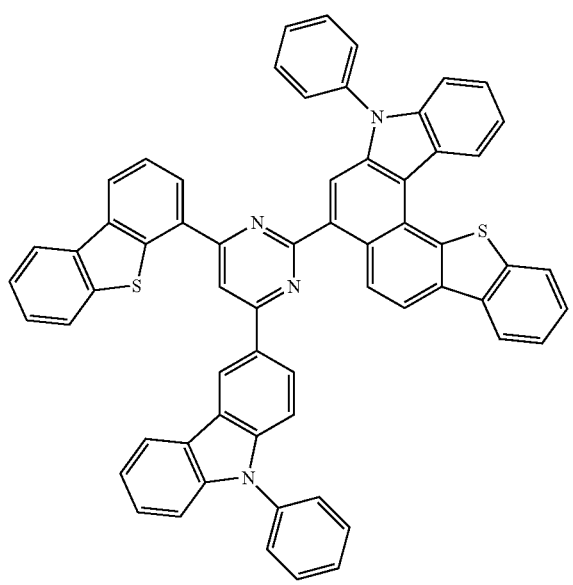
55
56
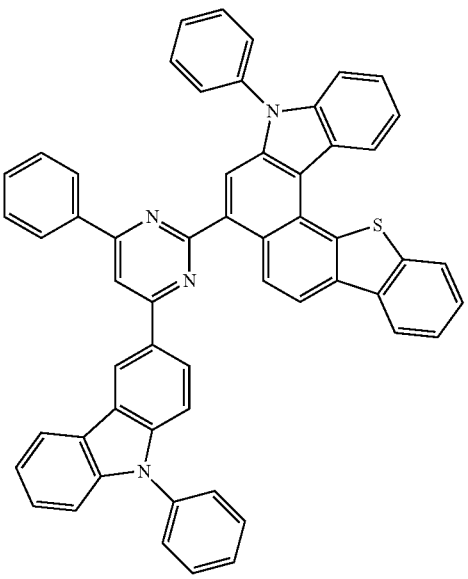
57
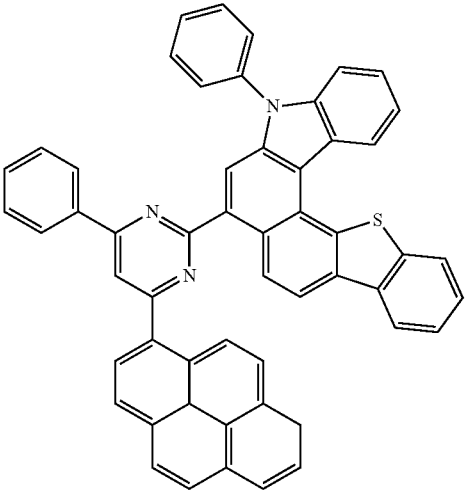
58
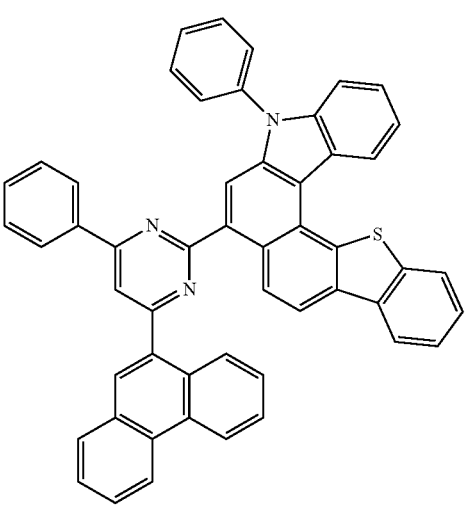

31
-continued
59
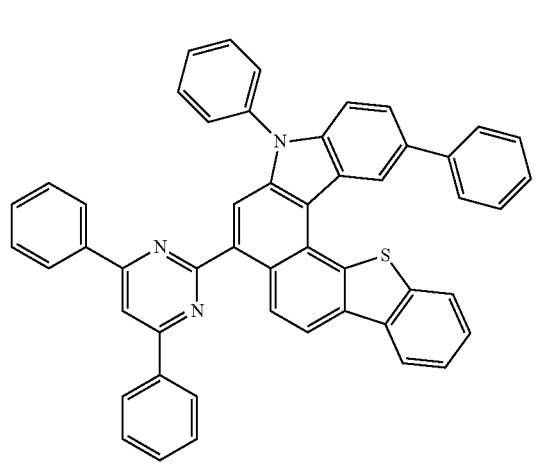
60
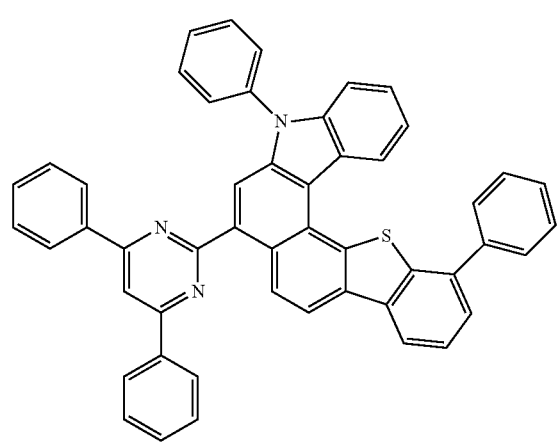
61
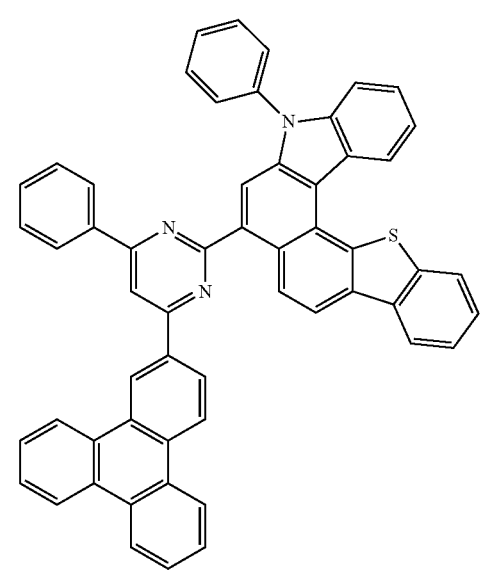
32
-continued
62
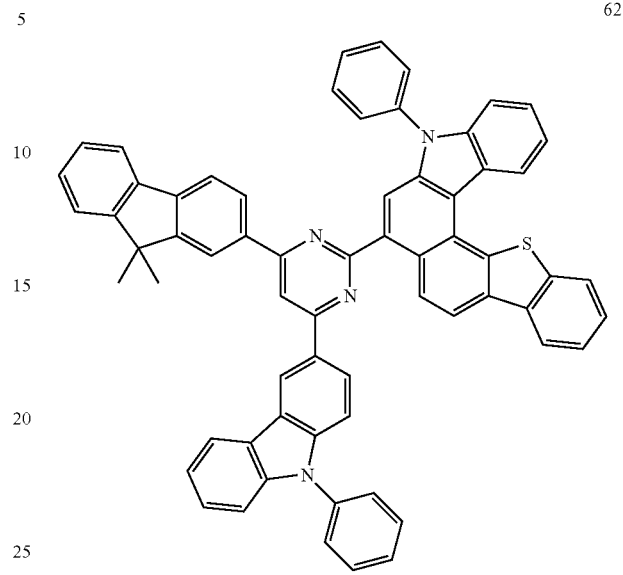
63
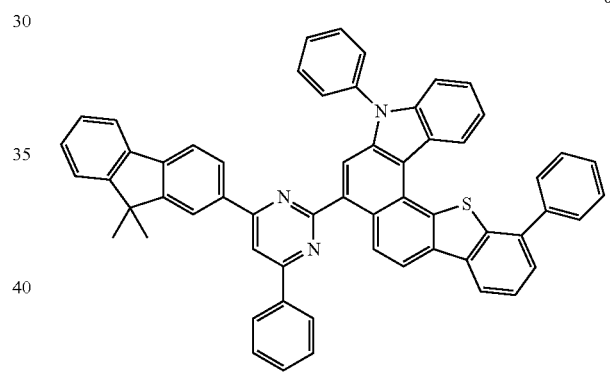
64
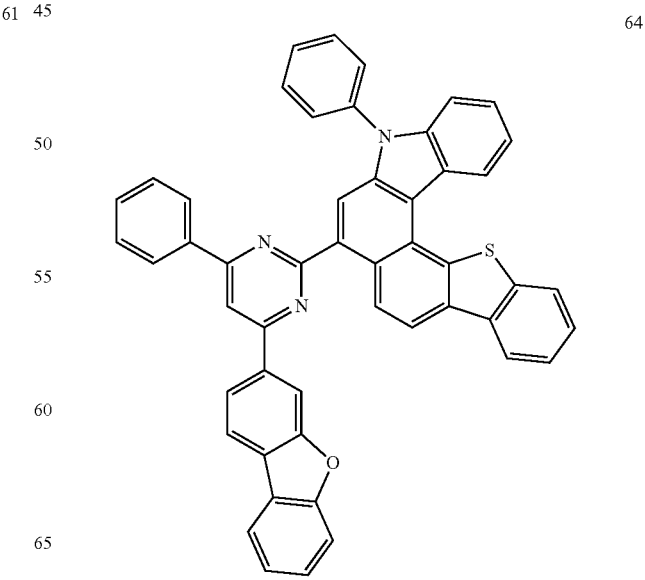

33
-continued
65
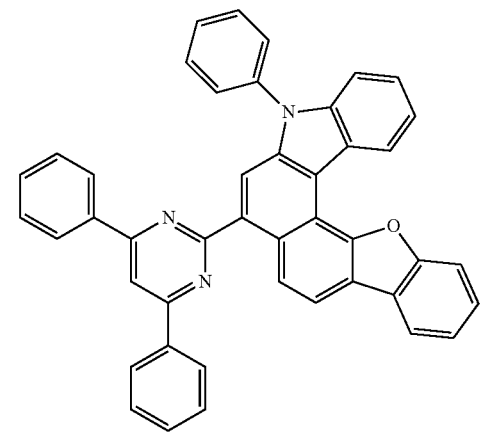
66
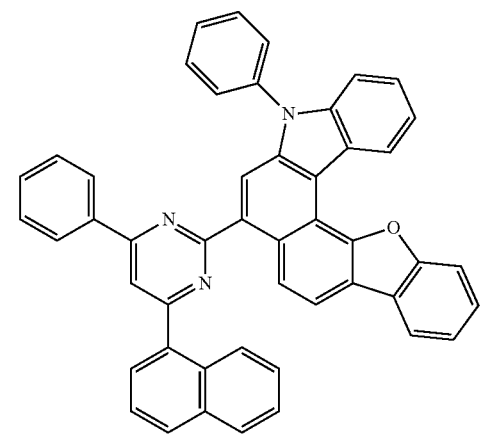
67
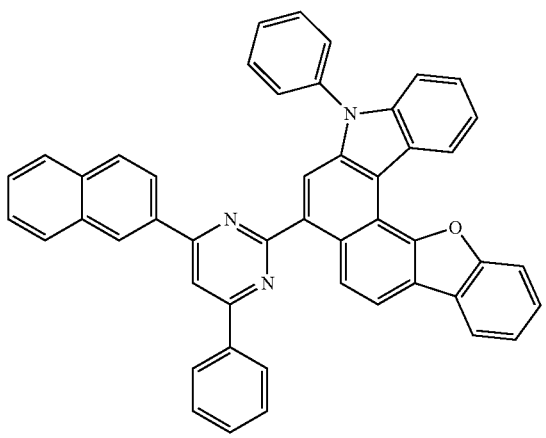
34
-continued
68
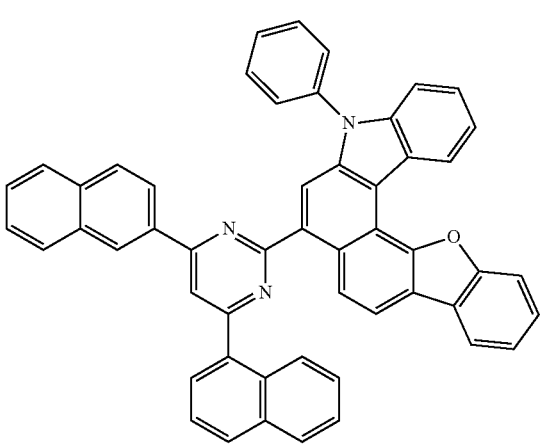
69
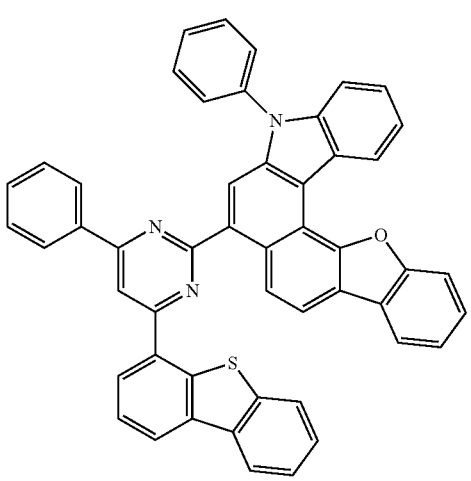
70
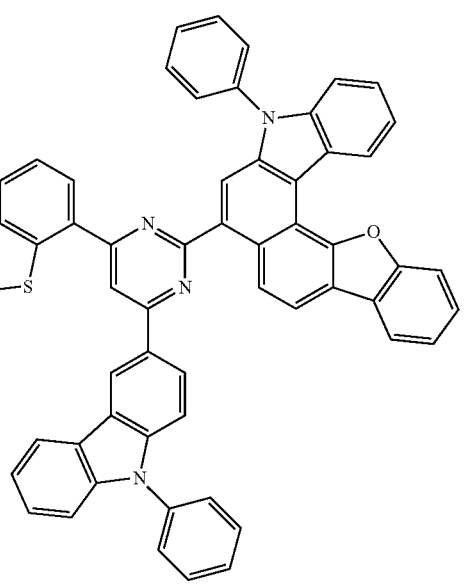

71
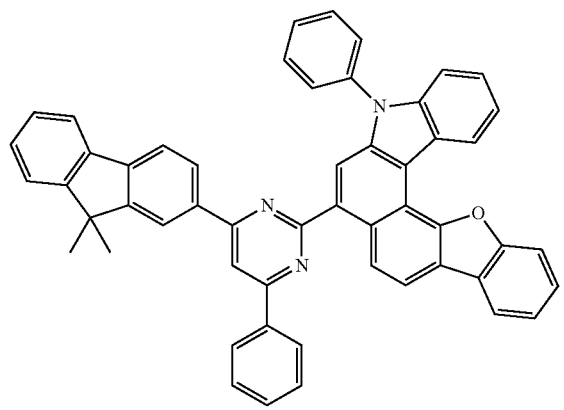
72
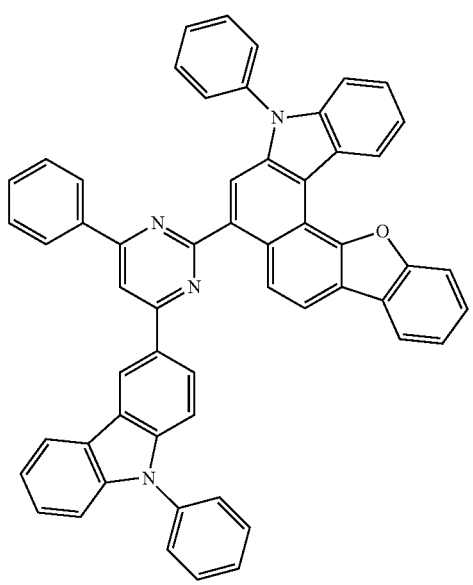
73
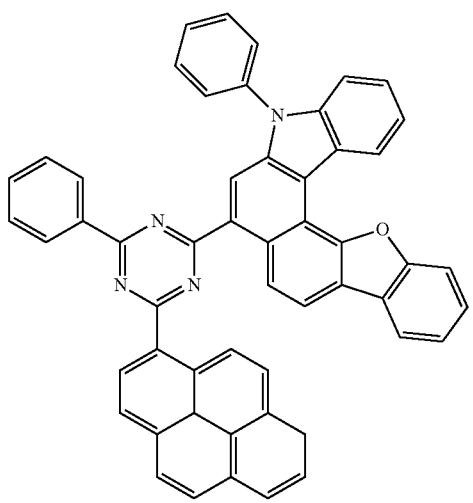
74
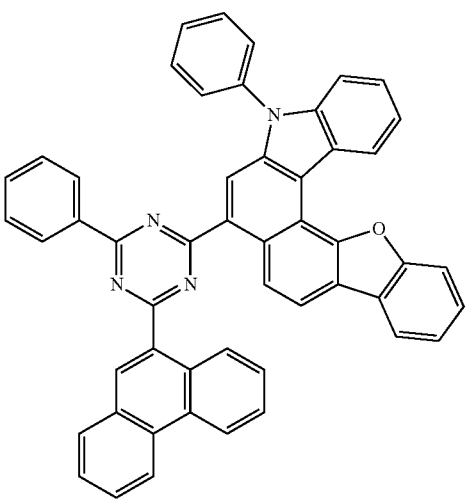
75
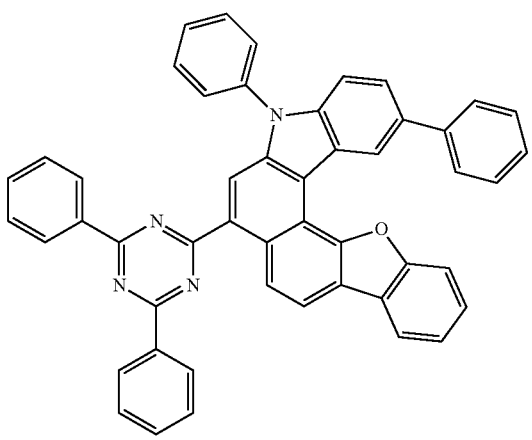
76
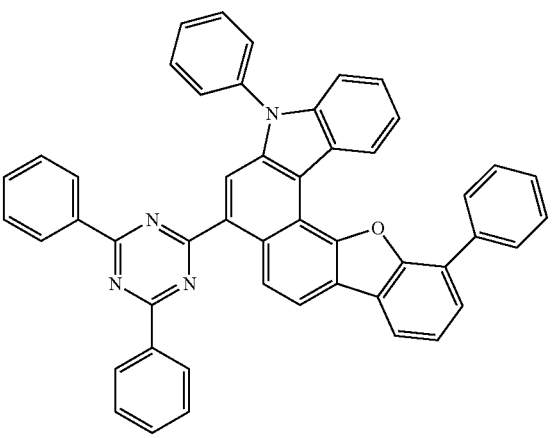

77
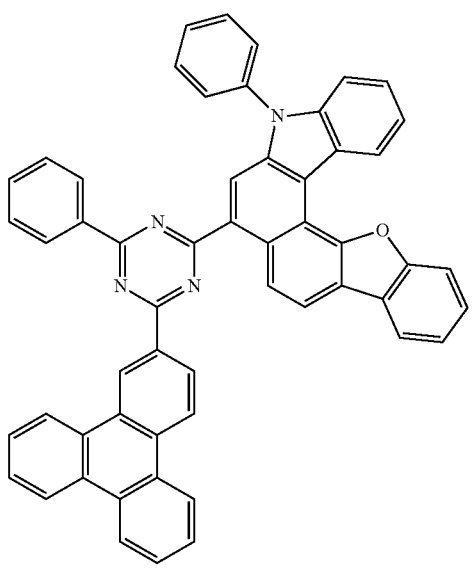
78
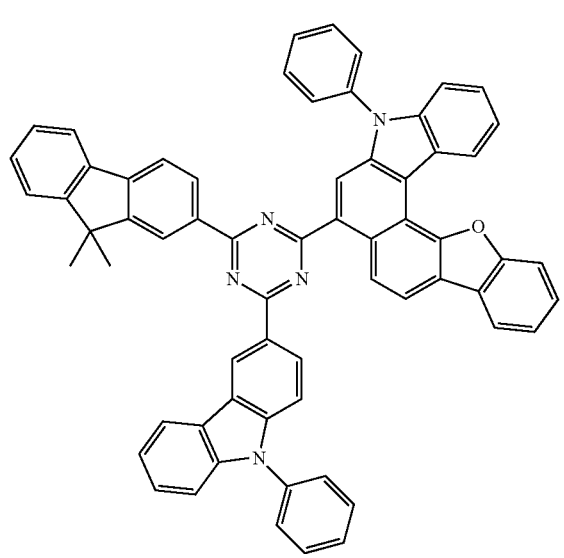
79
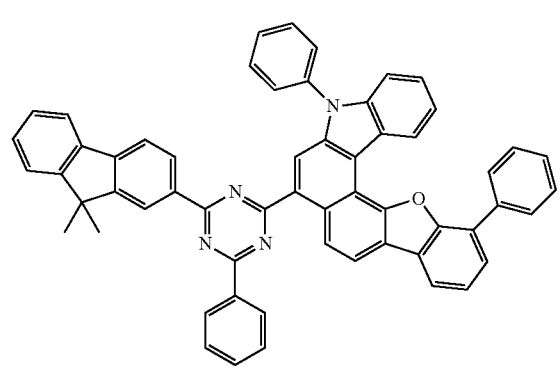
80
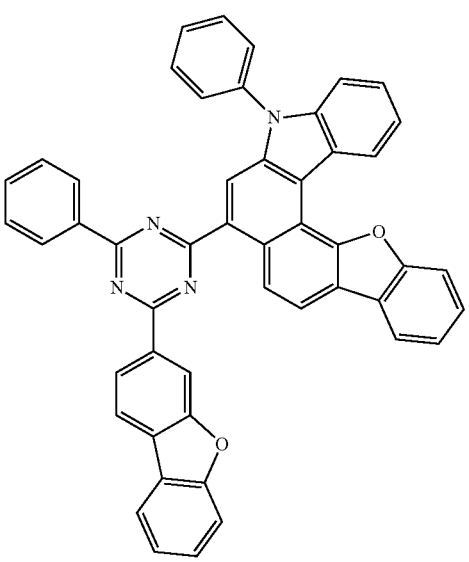
81
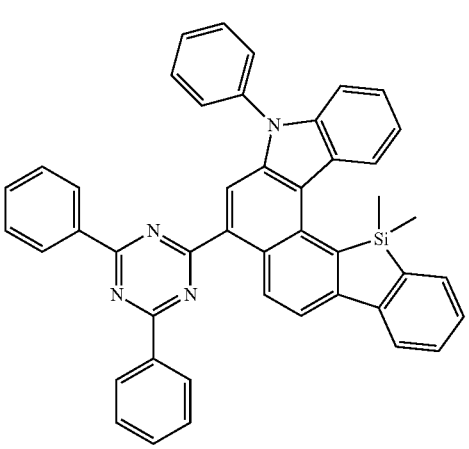
82
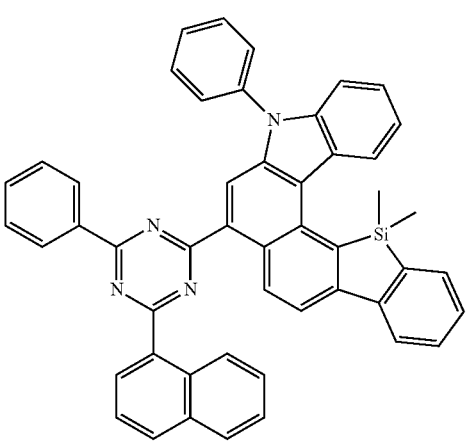

83
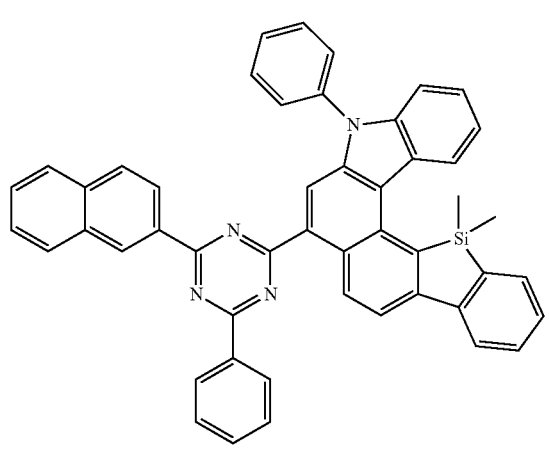
84
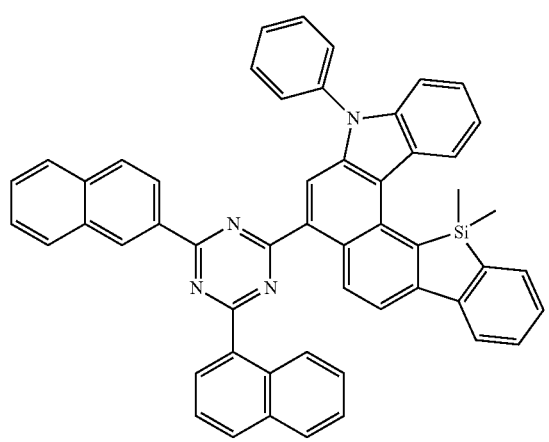
85
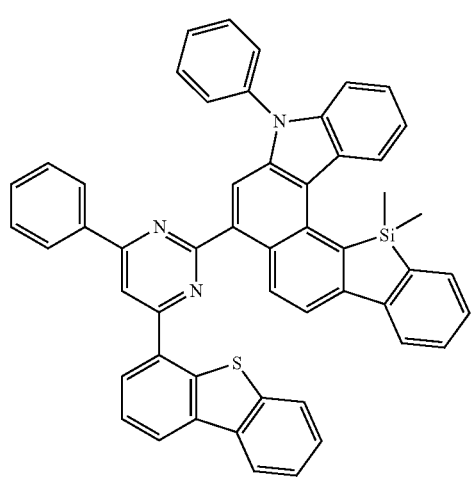
86
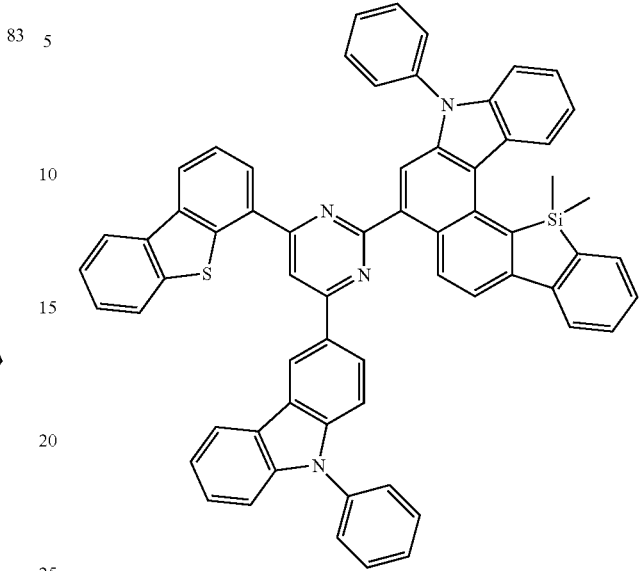
87
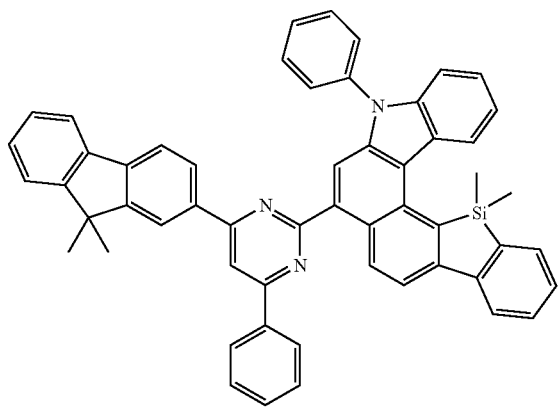
88
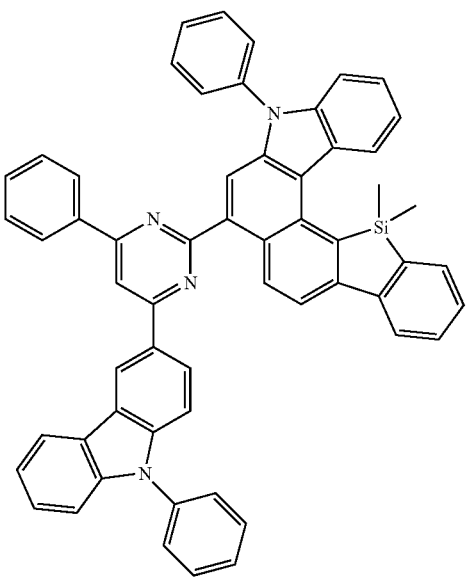

89
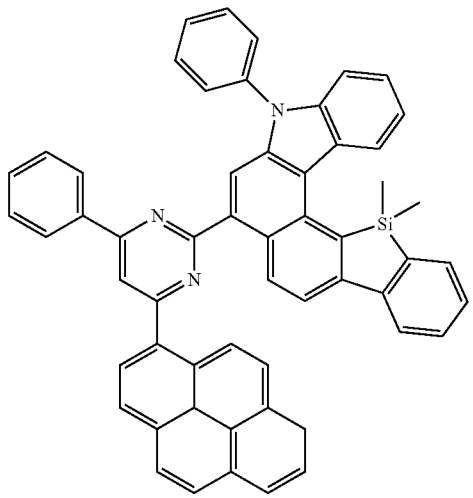
90
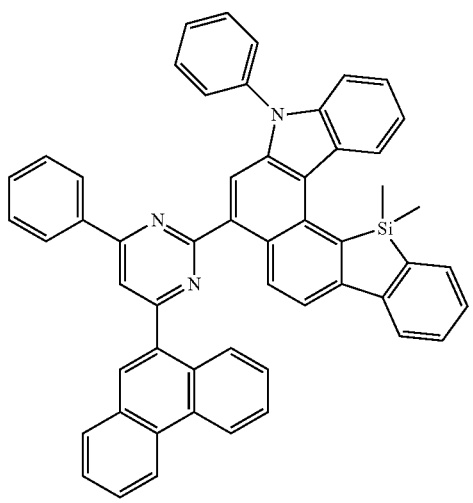
91
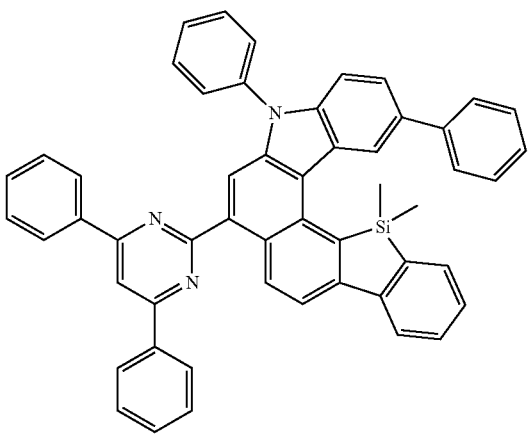
92
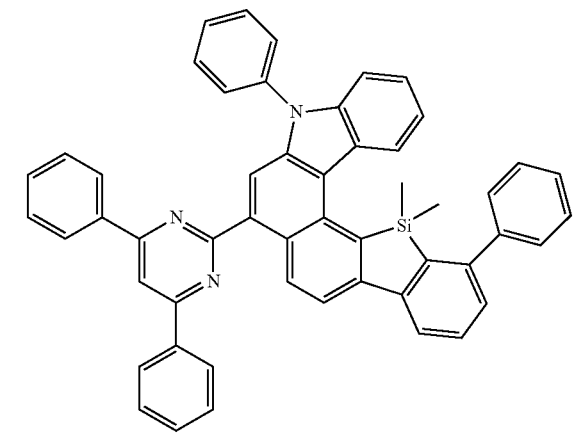
93
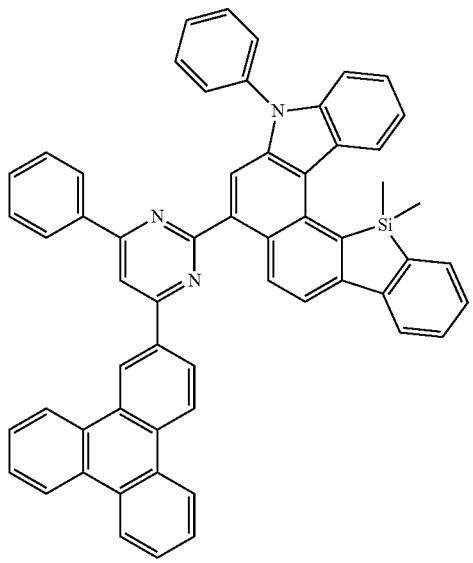
94
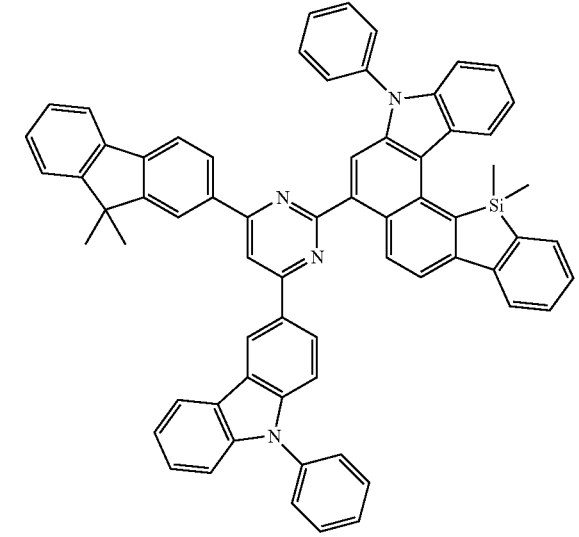

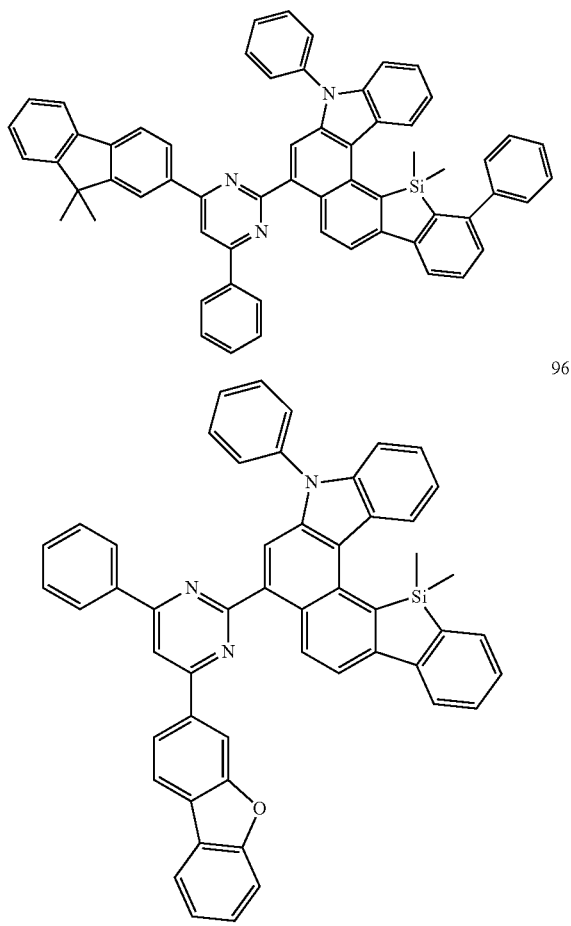

95

96

The fused ring compound represented by Formula 1 above may have a fused structure of intramolecular carbazols and heteroaromatic groups, or a fused structure of intramolecular carbazole and silol group, and a nitrogen-containing hetero ring, which together form a rigid backbone of the fused ring compound, and an aromatic group or heteroaromatic group as a substituent is bound to the backbone via a linker. Due to this structure, the fused ring compound of Formula 1 may have a high glass transition temperature and a high melting point.

An organic light-emitting device including the fused ring compound of Formula 1 may have high heat resistance against a Joule heat generated between organic layers, in an organic layer, and/or between an EML and a metal electrode when stored and/or operated. Therefore, the organic light-emitting device including the fused ring compound may have consistent thermal stability even with time in a high-temperature environment, and high durability and long lifetime.

The fused ring compound of Formula 1 may be synthesized by using organic synthesis. A synthesis method of the fused ring compound of Formula 1 may be understood by those of ordinary skill in the art from the examples that will be described below.

The fused ring compound of Formula 1 may be used between a pair of electrodes of an organic light-emitting device. For example, the fused ring compound may be used in an emission layer, in a layer between the anode and the emission layer (for example, a hole injection layer, a hole transport layer, or a functional layer with both hole injection and transport capabilities), and/or in a layer between the cathode and the emission layer (for example, an electron injection layer, an electron transport layer, or a functional layer with both hole injection and transport capabilities).

According to another aspect of the present invention, an organic light-emitting device includes a first electrode, a second electrode disposed opposite to the first electrode, and an organic layer disposed between the first electrode and the second electrode, wherein the organic layer includes the fused ring compound of Formula 1 described above.

The term "organic layer" as used herein refers to a single layer and/or a plurality of layers disposed between the first and second electrodes of the organic light-emitting device.

As used herein, the organic layer including the fused ring compound of Formula 1 can refer to the organic layer including one or at least two different fused ring compounds represented by Formula 1 above.

The organic layer may include at least one of a hole injection layer, a hole transport layer, a functional layer having both hole injection and hole transport capabilities, a buffer layer, an emission layer, a hole blocking layer, an electron transport layer, an electron injection layer, and a functional layer having both electron injection and electron transport capabilities.

The organic layer may include at least one of a hole injection layer, a hole transport layer, and a functional layer having both hole injection and hole transport capabilities, and at least one of the hole injection layer, the hole transport layer, and the functional layer having both hole injection and hole transport capabilities may include the fused ring compound of Formula 1.

At least one of the hole injection layer, the hole transport layer, and the functional layer having both hole injection and hole transport capabilities may further include a charge-generating material, which may be at least one of a quinine derivative, a metal oxide, and a cyano group-containing compound. Examples of the metal oxide are molybdenum oxides and vanadium oxides. The charge-generating material with strong electron acceptability may facilitate injection and transport of holes.

The organic layer may include at least one of an electron injection layer, an electron transport layer, and a functional layer having both electron injection and electron transport capabilities, and at least one of the electron injection layer, the electron transport layer, and the functional layer having both electron injection and electron transport capabilities may include the fused ring compound represented by Formula 1 above.

The organic layer may include an emission layer, and the emission layer may further include the fused ring compound represented by Formula 1 described above.

The fused ring compound of Formula 1 may have an appropriate energy level for use as a material for forming the emission layer, due to broken conjugation at $X_1$ and $X_2$ of the fused ring compound.

The fused ring compound of Formula 1 in the emission layer may be used as a phosphorescent host. The fused ring compound in the emission layer may serve as a phosphorescent host emitting red light, green light, or a blue light, and in particular, may be used as a phosphorescent host of green light.

The organic layer may include an emission layer, and at least one of an electron injection layer, an electron transport layer and a functional layer having both electron injection and electron transport capabilities, wherein the emission layer may include an arylamine compound. The arylamine compound may be any of suitable compounds used in the emission layer.

Hereinafter, a structure of an organic light-emitting device 10 according to an embodiment of the present invention and a method of manufacturing the same will now be described with reference to the drawing. However, the present invention is not limited thereto.

The drawing is a schematic sectional view of an organic light-emitting device (OLED) 10 according to an embodiment of the present invention.

The substrate 11, which may be any substrate that is used in general organic light-emitting devices, may be a glass substrate or a transparent plastic substrate with excellent mechanical strength, thermal stability, transparency, surface smoothness, ease of handling, and water resistance.

The first electrode 13 may be formed by depositing or sputtering a first electrode-forming material on the substrate 11. When the first electrode 13 constitutes an anode, a material having a high work function may be used as the first electrode-forming material to facilitate hole injection. The first electrode 13 may be a reflective electrode or a transmission electrode. A transparent material with high conductivity, such as ITO, IZO, $SnO_2$, and ZnO, may be used as the first electrode-forming material. In some embodiments, the first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like. The first electrode 13 may have a single-layer structure or a multi-layer structure including at least two layers. For example, the first electrode 13 may have a three-layered structure of ITO:Ag:ITO, but is not limited thereto.

The organic layer 15 may be disposed on the first electrode 13. The organic layer 15 may include a hole injection layer (HIL), a hole transport layer (HTL), a buffer layer, an emission layer (EML) 16, an electron transport layer (ETL), and an electron injection layer (EIL).

The HIL may be formed on the first electrode 13 using any of a variety of methods, such as vacuum deposition, spin coating, casting, Langmuir-Blodgett (LB) deposition, or the like. When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C. a pressure of about $10^{-8}$ torr to about $10^{-3}$ torr, and a deposition rate of about 0.01 Å/sec to about 100 Å/sec. However, the deposition conditions are not limited thereto. When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto. A HIL-forming material may be at least one of the fused ring compound of Formula 1 and a suitable HIL forming material. Non-limiting examples of suitable HIL-forming materials are N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4"-tris (3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and polyaniline)/poly(4-styrenesulfonate) (PANI/PSS). The thickness of the HIL may be from about 100 Å to about 10000 Å, and in some embodiments, may be from about 100 Å to about 1000 Å. When the thickness of the HIL is within these ranges, the HIL may have good hole injecting ability without a substantial increase in driving voltage.

Then, an HTL may be formed on the HIL by using any of a variety of suitable methods, such as vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to the material that is used to form the HTL. An HTL-forming material may be at least one of the fused ring compound of Formula 1 and any suitable HTL-forming materials. Non-limiting examples of suitable HTL-forming materials are carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl) triphenylamine (TCTA), and N,N'-di(1-naphthyl)-N,N'-diphenylbenzidine) (NPB). The thickness of the HTL may be from about 50 Å to about 2000 Å, and in some embodiments, may be from about 100 Å to about 1500 Å. When the thickness of the HTL is within these ranges, the HTL may have good hole transporting ability without a substantial increase in driving voltage.

The functional layer having both hole injection and hole transport capabilities may contain at least one of the fused ring compound of Formula 1, an HIL-forming material, and an HTL-forming material. A thickness of the functional layer having both hole injection and hole transport capabilities may be from about 500 Å to about 10,000 Å, and in some embodiments, may be from about 100 Å to about 1,000 Å. When the thickness of the functional layer having both hole injection and hole transport capabilities is within these ranges, the functional layer may have good hole injection and transport capabilities without a substantial increase in driving voltage.

At least one of the HIL, the HTL, and the functional layer having both hole injection and transport capabilities may further include a charge-generating material as described above for improved conductivity of the layer, in addition to one of the fused ring compound of Formula 1, a suitable HIL-forming material, and a suitable HTL-forming material as described above.

A buffer layer may be disposed between at least one of the HIL, HTL, and functional layer having both hole injection and transport capabilities, and the EML 16. The buffer layer may compensate for an optical resonance distance of light according to a wavelength of the light emitted from the EML 16, and thus may increase efficiency. The buffer layer may include any suitable HIL-forming material, or an HTL-forming material.

Then, the EML 16 may be formed on the HTL, the functional layer having both hole injection and transport capabilities, or the buffer layer by vacuum deposition, spin coating, casting, Langmuir-Blodget (LB) deposition, or the like. When the EML 16 is formed using vacuum deposition or spin coating, the deposition and coating conditions may be similar to those for the formation of the HIL, though the conditions for deposition and coating may vary according to the material that is used to form the EML 16.

The EML 16 may include the fused ring compound of Formula 1 as a host material. In some embodiments, the EML 16 may further include a suitable host, in addition to the fused ring compound of Formula 1. Non-limiting examples of the suitable host are $Alq_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, distyrylarylene (DSA), and dmCBP.

When the organic light-emitting device 10 includes at least one of a red EML, a green EML, and a blue EML, the EML 16 may include a dopant below (ppy=phenylpyridine).

Non-limiting examples of a blue dopant are compounds represented by the following formulae.

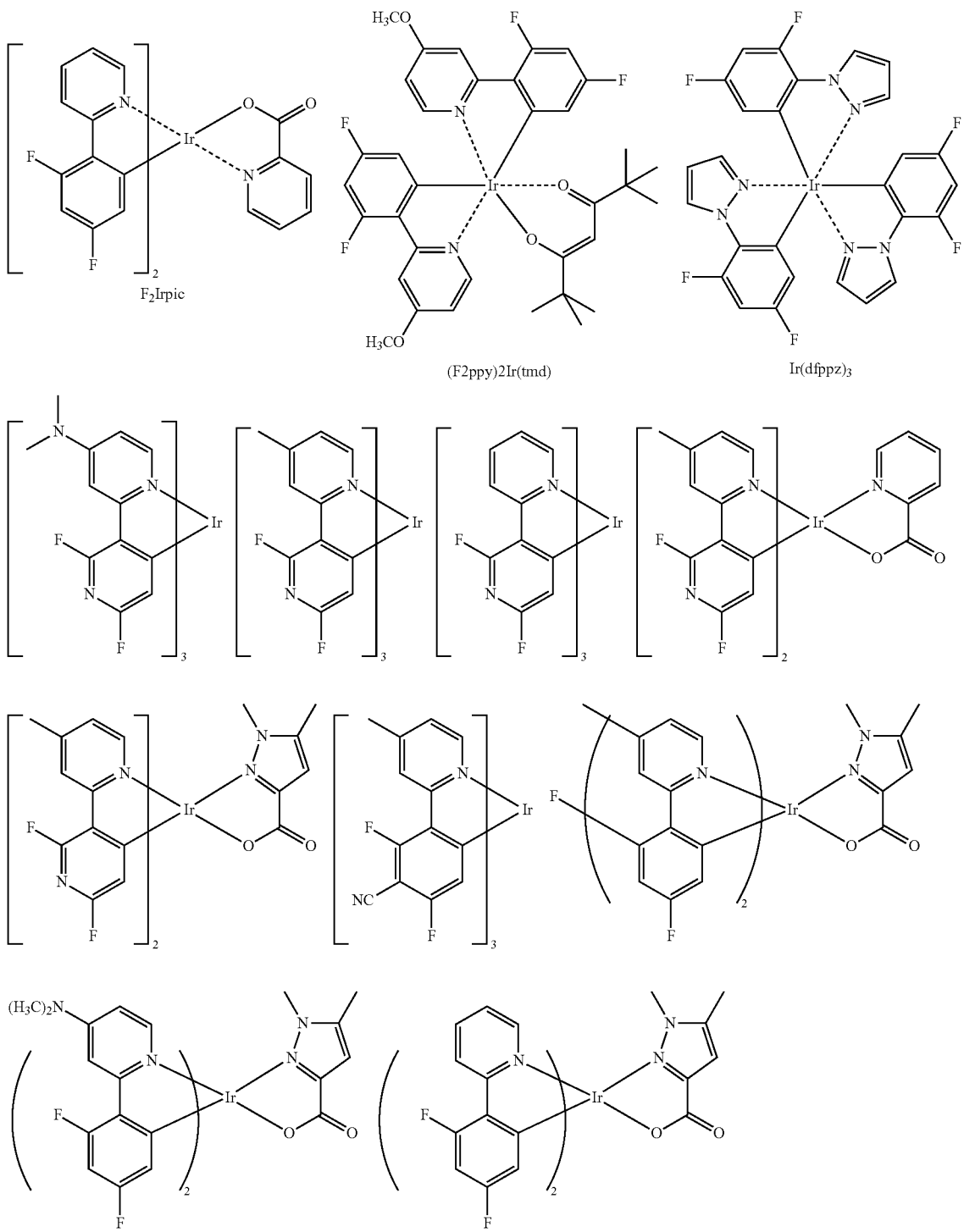

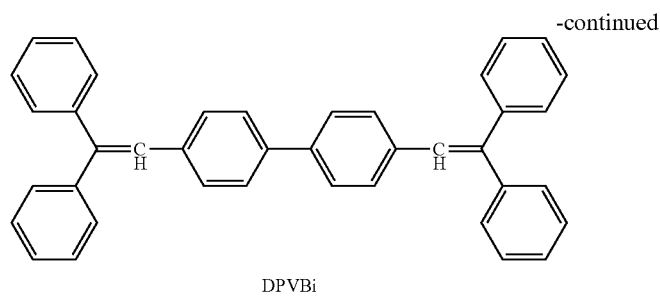
DPVBi
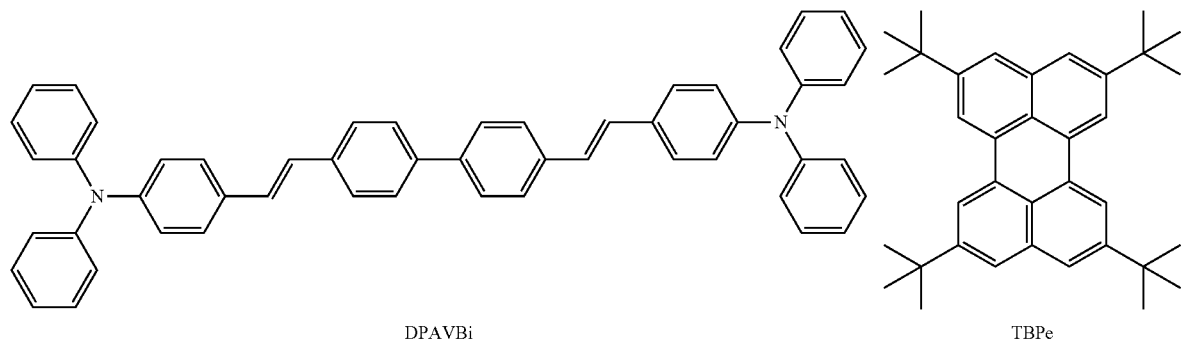
DPAVBi
TBPe
Non-limiting examples of red dopant are compounds represented by the following formulae.
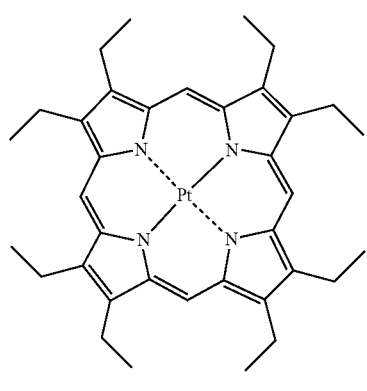
PtOEP
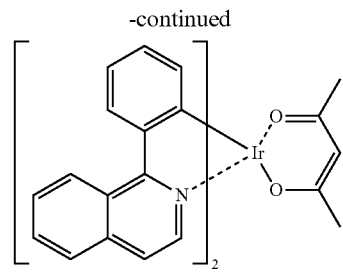
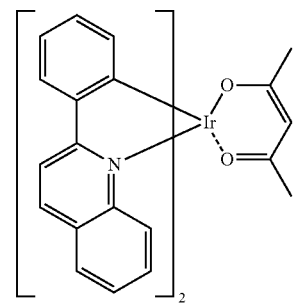
Ir(pq)₂(acac)          Ir(2-phq)₃
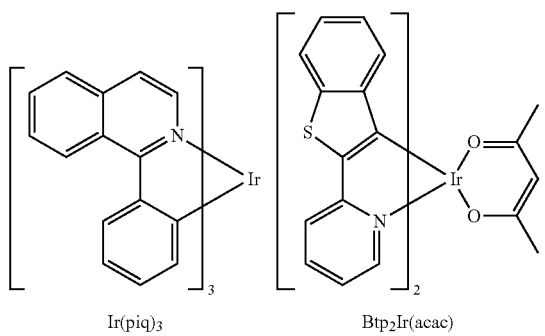
Ir(piq)₃          Btp₂Ir(acac)
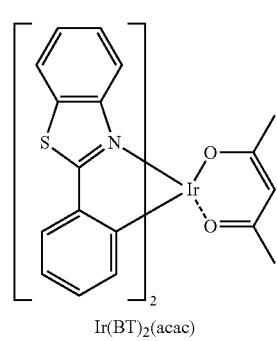
Ir(BT)₂(acac)

Non-limiting examples of the green dopant are compounds represented by the following formulae.

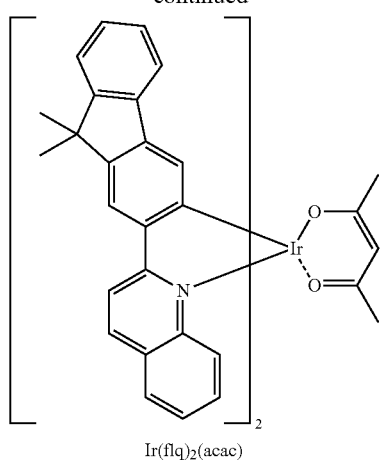

Ir(flq)₂(acac)

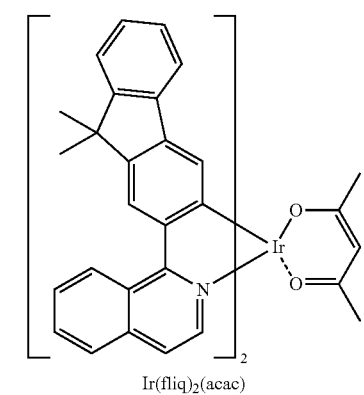

Ir(fliq)₂(acac)

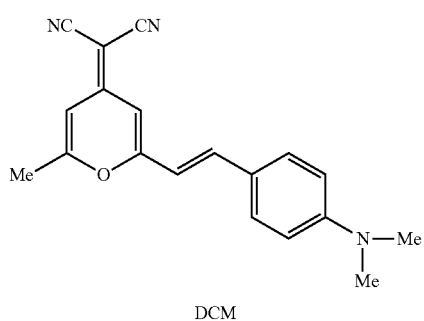

DCM

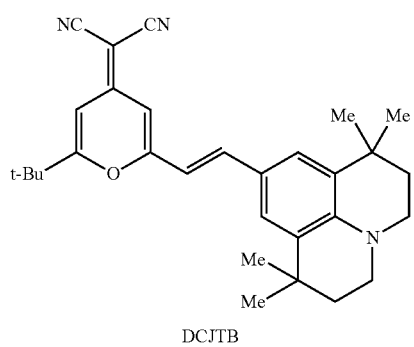

DCJTB

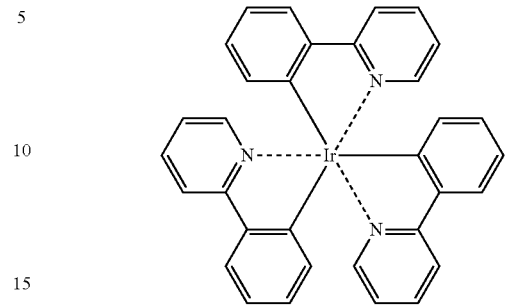

Ir(ppy)₃

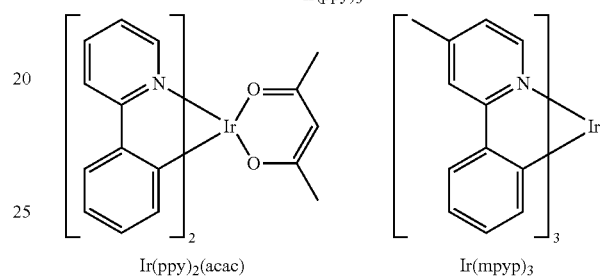

Ir(ppy)₂(acac)    Ir(mpyp)₃

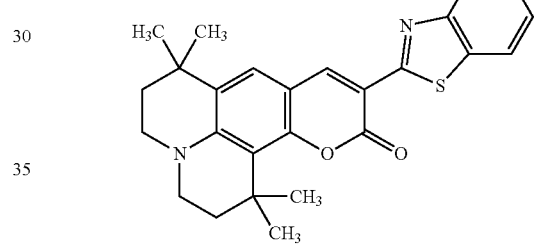

C545T

Non-limiting examples of dopants for the EML 16 are a Pt-complex and an Os-complex.

When the EML 16 of the organic light-emitting device 10, and at least one of the EIL, the ETL, and the functional layer having both electron injection and transport capabilities include the fused ring compound of Formula 1, the EML 16 may include a suitable arylamine compound.

When the EML 16 includes both a host and a dopant, the amount of the dopant may be from about 0.01 parts to about 15 parts by weight based on 100 parts by weight of the host. However, the amount of the dopant is not limited to this range.

A thickness of the EML 16 may be from about 100 Å to about 1000 Å, and in some embodiments, may be from about 200 Å to about 600 Å. When the thickness of the EML 16 is within these ranges, the EML 160 may have improved light emitting ability without a substantial increase in driving voltage.

Then, an ETL may be formed on the EML 16 using any of a variety of methods, such as vacuum deposition, spin coating, casting, or the like. When the ETL is formed using vacuum deposition or spin coating, the deposition and coating conditions may be similar to those for the formation of the HIL, though the deposition and coating conditions may vary according to a compound that is used to form the ETL. An HTL-forming material may be at least one of the fused ring compound of Formula 1 and any suitable HTL-forming materials able to stably transport electrons injected from the electron injection electrode (cathode). Non-limiting examples of suitable ETL forming materials are a quinoline derivative, such as tris(8-quinolinorate)aluminum (Alq3), TAZ, BAlq, beryllium bis(benzoquinolin-10-olate (Bebq₂), 9,10-di(naphthalene-2-yl)anthracene (ADN), Compound 201, and Compound 202.

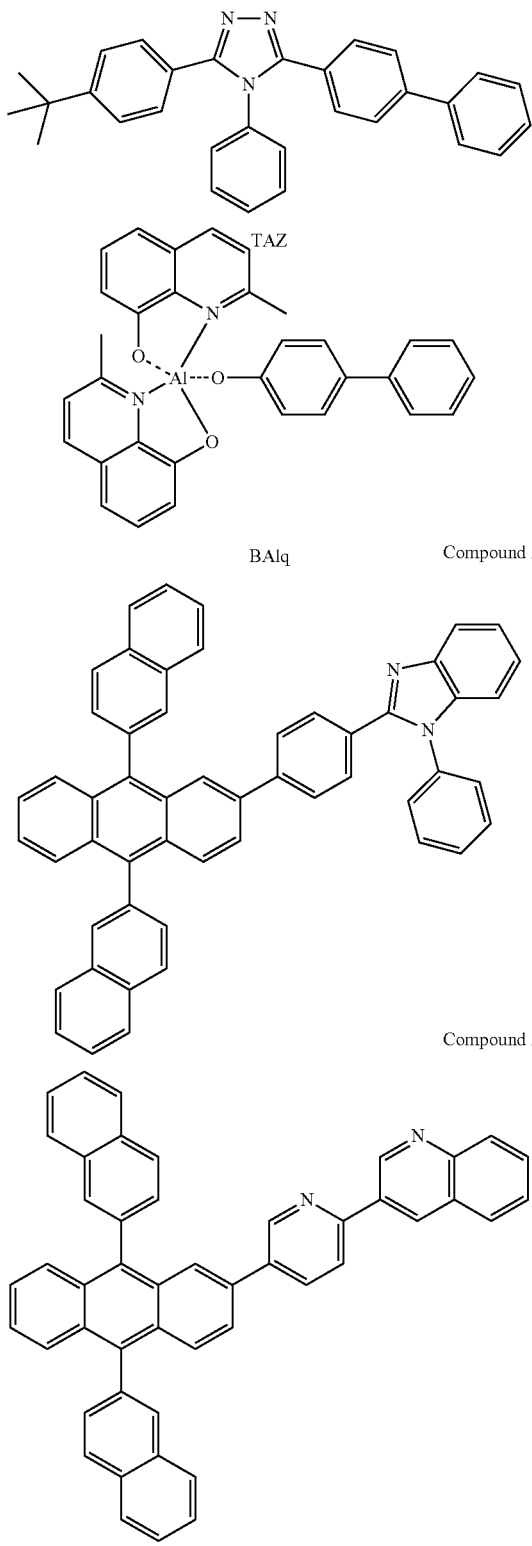

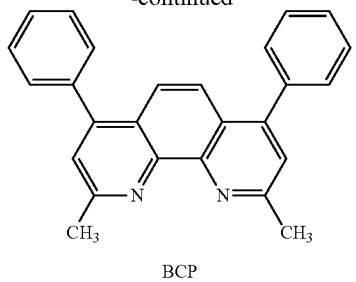

BCP

The thickness of the ETL may be from about 100 Å to about 1,000 Å, and in some embodiments, may be from about 150 Å to about 500 Å. When the thickness of the ETL is within these ranges, the ETL may have satisfactory electron transporting ability without a substantial increase in driving voltage.

The ETL may further include a metal complex, in addition to at least one of the fused ring compound of Formula 1 and the suitable ETL-forming material. The metal complex may be a lithium (Li) complex. Non-limiting examples of the Li complex are lithium quinolate (LiQ) and Compound 203 below:

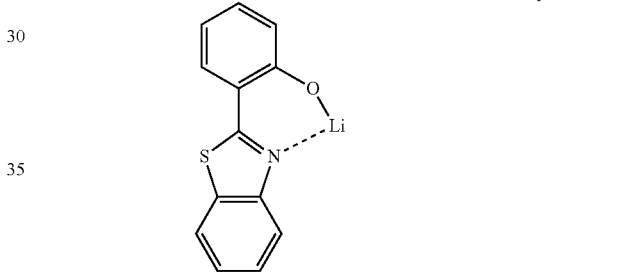

An EIL, which facilitates injection of electrons from the cathode, may be formed on the ETL. Examples of an EIL-forming material are LiF, NaCl, CsF, Li₂O, and BaO, which are suitable in the art. The deposition and coating conditions for forming the EIL may be similar to those for the formation of the HIL, though the deposition and coating conditions may vary according to the material that is used to form the EIL. A thickness of the EIL may be from about 1 Å to about 100 Å, and in some embodiments, from about 3 Å to about 90 Å. When the thickness of the EIL is within these ranges, the EIL may have satisfactory electron injection ability without a substantial increase in driving voltage.

The second electrode 19 is disposed on the organic layer 15. The second electrode 19 may be a cathode that is an electron injection electrode. Suitable metals for forming the second electrode 19 are a metel, an alloy and an electro-conductive compound that have a low work function, and mixtures thereof. For example, the second electrode 19 may be formed as a transmission electrode in a thin film form using Li, Mg, Al, Ca, Mg:In, Mg:Ag, or the like. In some embodiments, to manufacture a top-emission light-emitting device, the transmission electrode may be formed of indium tin oxide (ITO) or indium zinc oxide (IZO).

When a phosphorescent dopant is used in the EML, an HBL may be formed between the HTL and the EML 16 or between the functional layer having both hole injection and transport capabilities and the EML 16 by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. The HBL may be formed using a suitable HBL-forming material, for example, an oxadiazole derivative, a triazole derivative, a phenanthroline derivative, or the like, but is not limited thereto. For example, the HBL may be formed from BCP (2,9-dimethyl-4,7-diphenyl-1,10-phenanthroline) represented by the following formula.

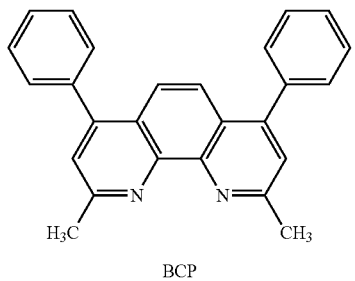 [SMILES: Cc1cc(-c2ccccc2)c2ccc3c(-c4ccccc4)cc(C)nc3c2n1 ; "BCP"]

BCP

A thickness of the HBL may be from about 20 Å to about 1000 Å, and in some embodiments, may be from about 30 Å to about 300 Å. When the thickness of the HBL is within these ranges, the HBL may have improved hole blocking properties without a substantial decrease in driving voltage.

According to another aspect of the present invention, an organic light-emitting display apparatus includes an organic light-emitting device including the fused ring compound of Formula 1 above. The organic light-emitting display apparatus may include a transistor with a source, a drain, a gate, and an active layer; and the above-described organic light-emitting device, wherein one of the source and the drain of the transistor is electrically connected to the first electrode of the organic light-emitting device. The active layer of the transistor may be in any of a variety of forms, for example, as an amorphous silicon layer, a crystalline silicon layer, an organic semiconductor layer, or an oxide semiconductor layer.

As used herein, examples of the unsubstituted $C_1$-$C_{40}$ alkyl group are $C_1$-$C_{41}$ linear or branched alkyl groups such as methyl, ethyl, propyl, isobutyl, sec-butyl, pentyl, iso-amyl, or hexyl. The substituted $C_1$-$C_{40}$ alkyl group is a $C_1$-$C_{40}$ alkyl group of which at least one hydrogen atom is substituted with a deuterium atom, a halogen atom, a hydroxyl group, a nitro group, a cyano group, an amino group, an amidino group, hydrazine, hydrazone, a carboxyl group or a salt thereof, sulfonic acid or a salt thereof, phosphoric acid or a salt thereof, a $C_1$-$C_{40}$ alkyl group, a $C_2$-$C_{40}$ alkenyl group, a $C_2$-$C_{40}$ alkynyl group, a $C_6$-$C_{40}$ aryl group, a $C_2$-$C_{40}$ heteroaryl group, —N($Q_{101}$)($Q_{102}$), or Si($Q_{103}$)($Q_{104}$)($Q_{105}$)($Q_{106}$)- (wherein $Q_{101}$ to $Q_{106}$ may each be independently selected from the group consisting of a hydrogen atom, a $C_1$-$C_{40}$ alkyl group, a $C_2$-$C_{40}$ alkenyl group, a $C_2$-$C_{40}$ alkynyl group, a $C_6$-$C_{40}$ aryl group, and a $C_2$-$C_{40}$ heteroaryl group).

As used herein, the unsubstituted alkoxy group refers to a group having a structure of —$OA_1$, wherein $A_1$ is an unsubstituted $C_1$-$C_{40}$ alkyl group as described above. Non-limiting examples of the unsubstituted $C_1$-$C_{60}$ alkoxy group are a methoxy group, an ethoxy group, and an isopropyloxy group. The substituted $C_1$-$C_{40}$ alkoxy group refers to a $C_1$-$C_{40}$ alkoxy group of which at least one hydrogen atom is substituted with the same substituents as described in connection with the substituted $C_1$-$C_{40}$ alkyl group.

As used herein, the unsubstituted $C_2$-$C_{40}$ alkenyl group indicates a hydrocarbon chain having at least one carbon-carbon double bond in the center or at a terminal of the unsubstituted $C_2$-$C_{40}$ alkyl group. Non-limiting examples of the alkenyl group are an ethenyl group, a propenyl group, and a butenyl group. The substituted $C_2$-$C_{40}$ alkenyl group refers to a $C_2$-$C_{40}$ alkenyl group of which at least one hydrogen atom is substituted with the same substituents as described in connection with the substituted $C_1$-$C_{40}$ alkyl group.

As used herein, the unsubstituted $C_2$-$C_{40}$ alkynyl group (or $C_2$-$C_{30}$ alkynyl group) is a $C_2$-$C_{40}$ alkyl group having at least one carbon-carbon triple bond in the center or at a terminal of the $C_2$-$C_{40}$ alkyl group. Non-limiting examples of the unsubstituted $C_2$-$C_{40}$ alkynyl group are ethynyl and propynyl. The substituted $C_2$-$C_{40}$ alkynyl group refers to a $C_2$-$C_{40}$ alkynyl group of which at least one hydrogen atom is substituted with the same substituents as described in connection with the substituted $C_1$-$C_{40}$ alkyl group.

As used herein, the unsubstituted $C_3$-$C_{40}$ cycloalkyl group refers to a group in which carbon atoms of an unsubstituted $C_3$-$C_{40}$ alkyl group form a ring. The substituted $C_3$-$C_{40}$ cycloalkyl group refers to a $C_3$-$C_{40}$ cycloalkyl group of which at least one hydrogen atom is substituted with the same substituents as described in connection with the substituted $C_1$-$C_{40}$ alkyl group.

As used herein, the substituted or unsubstituted $C_3$-$C_{40}$ cycloalkenyl group refers to a group in which carbon atoms of an unsubstituted $C_3$-$C_{40}$ alkenyl group form a ring. The substituted $C_3$-$C_{40}$ cycloalkenyl group refers to a $C_3$-$C_{40}$ cycloalkenyl group of which at least one hydrogen atom is substituted with the same substituents as described in connection with the substituted $C_1$-$C_{40}$ alkyl group.

As used herein, the unsubstituted $C_6$-$C_{40}$ aryl group refers to a monovalent group having a carbocyclic aromatic system having 6 to 40 carbon atoms including at least one aromatic ring. The unsubstituted $C_6$-$C_{40}$ arylene group refers to a bivalent group having a carbocyclic aromatic system having 6 to 40 carbon atoms including at least one aromatic ring. When the aryl group or the arylene group have at least two rings, they may be fused to each other via a single bond. The substituted $C_6$-$C_{40}$ aryl group is a $C_6$-$C_{40}$ aryl group of which at least one hydrogen atom is substituted with the same substituents as described in connection with the substituted $C_1$-$C_{40}$ alkyl group. The substituted $C_6$-$C_{40}$ arylene group is a $C_6$-$C_{40}$ arylene group of which at least one hydrogen atom is substituted as the same substituents as described in connection with the substituted $C_1$-$C_{40}$ alkyl group.

As used herein, a substituted or unsubstituted $C_6$-$C_{40}$ arylalkyl group refers to a combining group of an alkyl group and a substituted or unsubstituted $C_6$-$C_{40}$ aryl group. The substituted $C_6$-$C_{40}$ arylalkyl group refers to a $C_6$-$C_{40}$ arylalkyl group of which at least one hydrogen atom is substituted with the same substitutents as described in connection with the substituted $C_1$-$C_{40}$ alkyl group.

As used herein, the unsubstituted $C_6$-$C_{40}$ aryloxy group is represented by —$OA_2$ (wherein $A_2$ is a substituted or unsubstituted $C_6$-$C_{30}$aryl group). The substituted $C_6$-$C_{40}$ aryloxy group is a $C_6$-$C_{40}$ aryloxy group of which at least one hydrogen atom is substituted with the same substituents as described in connection with the substituted $C_1$-$C_{40}$ alkyl group.

As used herein, the unsubstituted $C_6$-$C_{40}$ arylthio group is represented by —$SA_3$ (wherein $A_3$ is a substituted or unsubstituted $C_6$-$C_{40}$ aryl group). The substituted $C_6$-$C_{40}$ arylthio group is a $C_6$-$C_{40}$ arylthio group of which at least one hydrogen atom is substituted with the same substituents as described in connection with the substituted $C_1$-$C_{40}$ alkyl group.

As used herein, the unsubstituted $C_6$-$C_{40}$ arylamino group is represented by —$N(A_4)(A_5)$ (wherein $A_4$ and $A_6$ are each independently a substituted or unsubstituted $C_6$-$C_{40}$ aryl group). The substituted $C_6$-$C_{40}$ arylthio group is a $C_6$-$C_{40}$ arylthio group of which at least one hydrogen atom is substituted with the same substituents as described in connection with the substituted $C_1$-$C_{40}$ alkyl group.

As used herein, the unsubstituted $C_2$-$C_{40}$ heteroaryl group is a monovalent group with at least one aromatic ring including at least one heteroatom selected from among N, O, P, and S, and 2 to 40 carbon atoms. The unsubstituted $C_2$-$C_{40}$ heteroarylene group is a bivalent group with at least one aromatic ring including at least one heteroatom selected from among N, O, P, and S, and 2 to 40 carbon atoms. In this regard, when the $C_2$-$C_{40}$ heteroaryl group or the $C_2$-$C_{40}$ heteroarylene group includes at least two rings, they may be fused together via a single bond. The substituted $C_2$-$C_{40}$ heteroaryl group is a $C_2$-$C_{40}$ heteroaryl group of which at least one hydrogen atom is substituted with the same substituents as described in connection with the substituted $C_1$-$C_{40}$ alkyl group. The substituted $C_2$-$C_{40}$ heteroarylene group is a $C_2$-$C_{40}$ heteroarylene group of which at least one hydrogen atom is substituted as the same substituents as described in connection with the substituted $C_1$-$C_{40}$ alkyl group.

Hereinafter, the present invention will be described in detail with reference to the following synthesis examples and other examples. However, these examples are for illustrative purposes only and are not intended to limit the scope of the present invention.

First, Intermediate E was prepared from Compound A via Intermediates B, C and D, as illustrated in Reaction Scheme 1 below.

Reaction Scheme 1

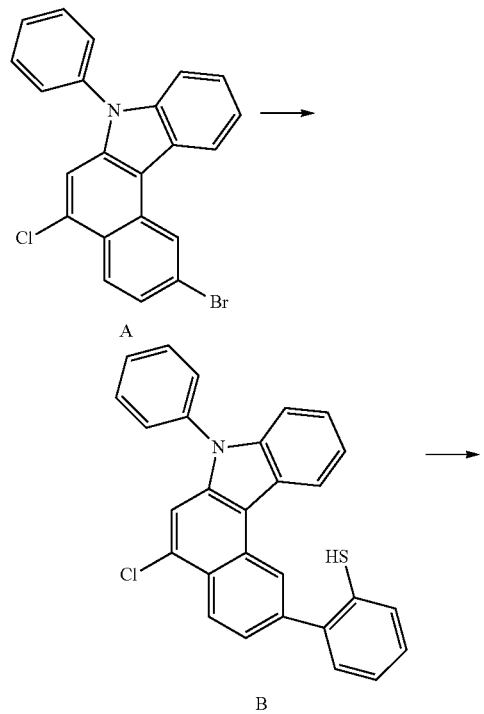

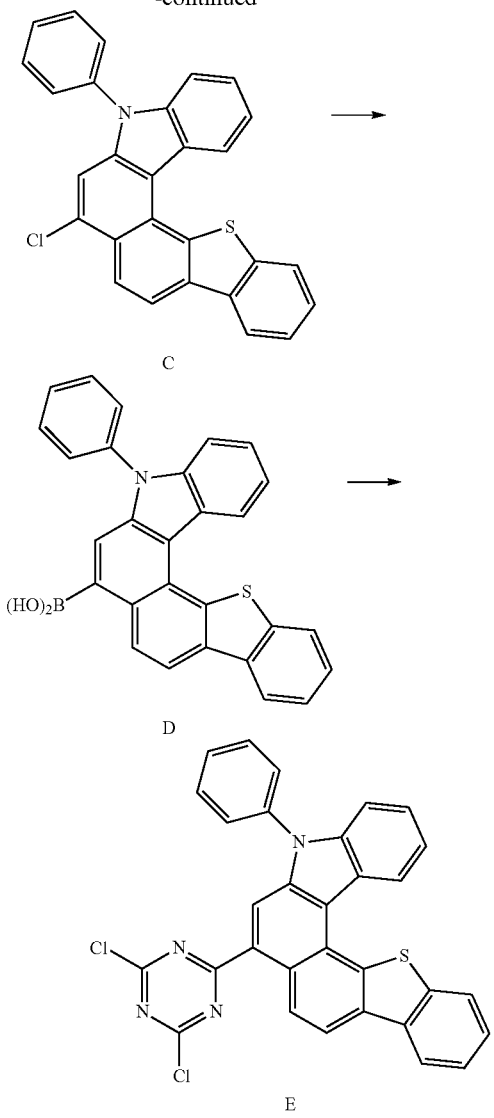

Synthesis of Intermediate E

<Step 1> Synthesis of Intermediate B 10 g (1 eq, 0.024 mol) of 2-bromo-5-chloro-7-phenyl-7H-benzo[c]carbazole and 4.5 g (1.2 eq, 0.029 mol) of 2-mercaptophenylboronic acid were dissolved in 400 ml of toluene. 0.95 g (0.02 eq, 0.001 mmol) of Pd(PPh$_3$)$_4$ and 100 mL of a 2M K$_2$CO$_3$ saturated solution were added into the solution, and then heated while stirring for about 12 hours.

A reaction solution from complete reaction was filtered through Celite, and a filtered product was refined by column chromatography to obtain 7.57 g of Intermediate B with a yield of about 72.4%.

GC-Mass (calc.: 435.2 g/mol, found: 434 g/mol)<

Step 1-1> Synthesis of Intermediate C 10 g (1 eq, 0.022 mol) of Intermediate B was put into a flask, and 100 ml of ether was added thereto, and 25 ml of a hydrogen peroxide solution (32%) was slowly added into the mixture. After being agitated at room temperature for about 5 hours, the mixture was washed with excess deionized water to obtain an organic phase, which was then dried using MgSO$_4$, and then refined by column chromatography to obtain 5.1 g of Intermediate C with a yield of about 52.1%.

GC-Mass (calc.: 433.07 g/mol, found: 432 g/mol)<
<Step 1-2> Synthesis of Intermediate D After 5 g (1 eq, 0.0115 mol) of Intermediate C was added into 100 ml of tetrahydrofuran (THF) in a reaction vessel, the temperature of the reaction vessel was lowered to about −78° C. (using acetone and dry ice). After 30 minutes, 12.2 ml of n-BuLi (1.6M in Hex) was slowly added into the reaction vessel. After 1 hour, 17.3 ml of 2-isopropyl borate was slowly added into the reaction vessel.

The temperature was increased to room temperature, and then maintained for 1 hours.

A reaction solution from complete reaction was washed with excess deionized water, and then was refined by column chromatography to obtain 3.9 g of Intermediate D with a yield of about 77.6%.

GC-Mass (calc.: 443.12 g/mol, found: 442 g/mol)
<Step 1-3> Synthesis of Intermediate E 10 g (1 eq, 0.022 mol) of Intermediate D and 3.7 g (0.9 eq, 0.02 mol) of 2,4,6-trichloro-1,3,5-triazine were dissolved in 40011ml of toluene. 0.95 g (0.01 eq, 0.001 mmol) of Pd(PPh$_3$)$_4$ and 100 mL of a 2M K$_2$CO$_3$ saturated solution were added into the solution, and then heated while stirring for about 12 hours.

A reaction solution from complete reaction was filtered through Celite, and a filtered product was refined by column chromatography to obtain 6.63 g of Intermediate E with a yield of about 55.1%.

GC-Mass (talc.: 546.05 g/mol, found: 545 g/mol)

Next, Compounds 1, 2, 5, 7, 8, and 13 were prepared from Intermediate E via Intermediate F, as illustrated in Reaction Scheme 2 below.

Synthesis of Compound 1

10 g (1 eq, 0.018 mol) of Intermediate E and 4.8 g of (2.2 eq, 0.0396 mol) of phenyl boronic acid were dissolved in 1000 ml of toluene. 0.9 g (0.007 eq, 0.0009 mmol) of Pd(PPh$_3$)$_4$ and 150 mL of a 2M K$_2$CO$_3$ saturated solution were added into the solution, and then heated while stirring for about 12 hours.

A reaction solution from complete reaction was filtered through Celite, and a filtered product was refined by column chromatography to obtain 9.5 g of Compound 1 with a yield of about 84%.

GC-Mass (calc.: 598.12 g/mol, found: 597 g/mol)
Elemental Analysis: C, 81.88; H, 4.15; N, 8.88; S, 5.08
Synthesis of Compound 2

8.1 g of Compound 2 was synthesized using Intermediate F and naphthalen-1-yl boronic acid, instead of Intermediate E and phenyl boronic acid, in the same manner as in the synthesis of Compound 1 (Yield: about 79.5%).

GC-Mass (calc.: 680.82 g/mol, found: 679 g/mol)
Elemental Analysis: C, 82.92; H, 4.15; N, 8.23; S, 4.71
Synthesis of Compound 5

9.2 g of Compound 5 was synthesized using dibenzo[b,d]thiophen-4-yl boronic acid, instead of naphthalene-1-yl boronic acid, in the same manner as in the synthesis of Compound 2 (Yield: about 82.1%).

GC-Mass (calc.: 736.90 g/mol, found: 735 g/mol)
Elemental Analysis: C, 79.86; H, 3.83; N, 7.60; S, 8.70
Synthesis of Compound 7

8.1 g of Compound 7 was synthesized using 9,9-dimethyl-9H-fluoren-2-yl boronic acid, instead of naphthalen-1-yl Reaction Scheme 2

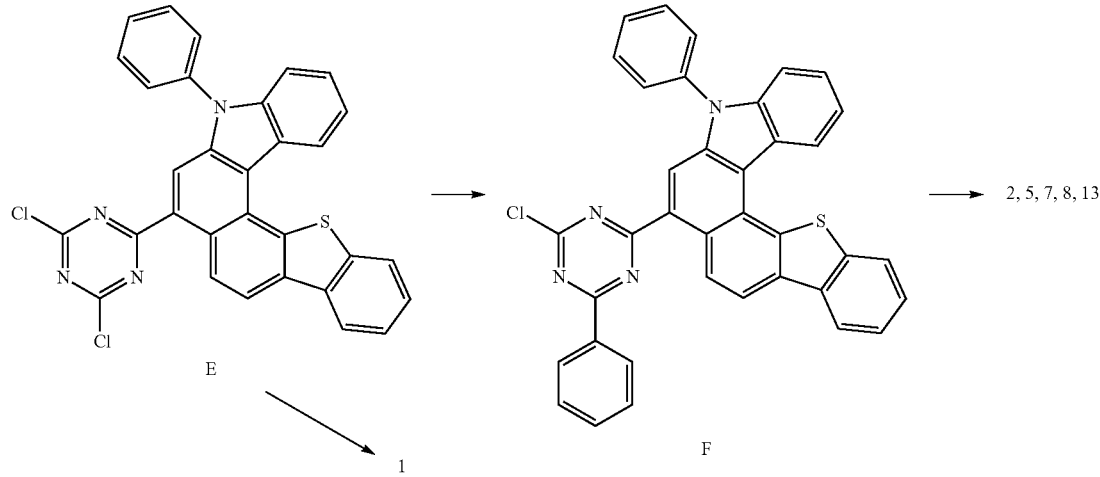

Synthesis of Intermediate F 10 g (1 eq, 0.018 mol) of Intermediate E and 2 g of (0.9 eq, 0.016 mol) of phenyl Moronic acid were dissolved in 600 ml of toluene. 0.5 g (0.01 eq, 0.0005 mmol) of Pd(PPh$_3$)$_4$ and 75 mL of a 2M K$_2$CO$_3$ saturated solution were added into the solution, and then heated while stirring for about 12 hours.

A reaction solution from complete reaction was filtered through Celite, and a filtered product was refined by column chromatography to obtain 5.51 g of intermediate F with a yield of about 52%.

GC-Mass (calc.: 598.12 g/mol, found: 597 g/mol)

boronic acid, in the same manner as in the synthesis of Compound 2 (Yield: about 72.2%).

GC-Mass (calc.: 746.92 g/mol, found: 745 g/mol)
Elemental Analysis: C, 83.62; H, 4.59; N, 7.50; S, 4.29
Synthesis of Compound 8

9.3 g of Compound 8 was synthesized using 9-phenyl-9H-carbazol-3-yl boronic acid, instead of naphthalen-1-yl boronic acid, in the same manner as in the synthesis of Compound 2 (Yield: about 75.9%).

GC-Mass (calc.: 795.95 g/mol, found: 798 g/mol)
Elemental Analysis: C, 82.99; H, 4.18; N, 8.80; S, 4.03

Synthesis of Compound 11

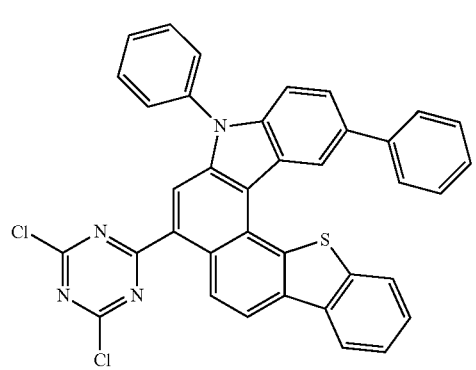

G

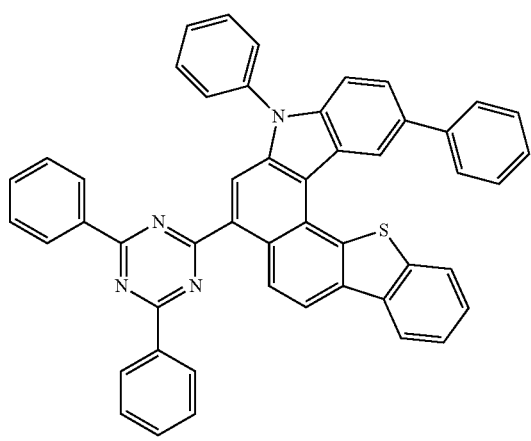

11

7.9 g of Compound 11 was synthesized using Intermediate G in the same manner as in the synthesis of Compound 1 (Yield: about 71.4%).

GC-Mass (calc.: 706.22 g/mol, found: 705 g/mol)

Elemental Analysis: C, 83.26; H, 4.28; N, 7.93; S, 4.54

Synthesis of Compound 12

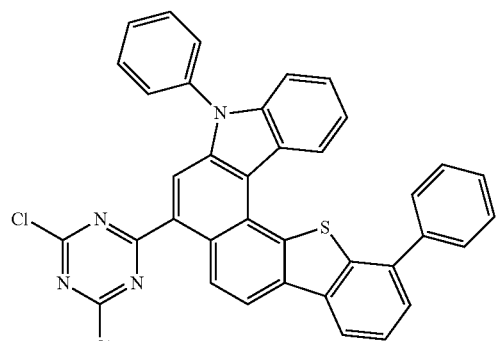

H

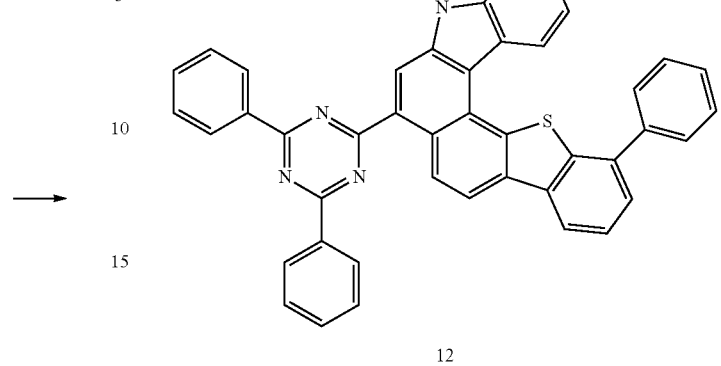

12

7.2 g of Compound 12 was synthesized using Intermediate H in the same manner as in the synthesis of Compound 1 (Yield: about 70.6%).

GC-Mass (calc.: 706.22 g/mol, found: 705 g/mol)

Elemental Analysis: C, 83.26; H, 4.28; N, 7.93; S, 4.54

Synthesis of Compound 13

8.7 g of Compound 13 was synthesized using triphenylen-2-yl boronic acid, instead of naphthalen-1-yl boronic acid, in the same manner as in the synthesis of Compound 2 (Yield: about 77.9%).

GC-Mass (calc.: 780.93 g/mol, found: 779 g/mol)

Elemental Analysis: C, 84.59; H, 4.13; N, 7.17; S, 4.11

Intermediate L was prepared from Intermediate J via Intermediate K, as illustrated in Reaction Scheme 3.

Reaction Scheme 3

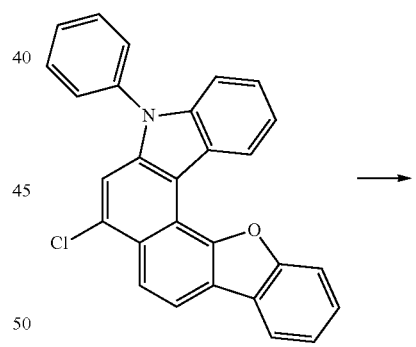

J

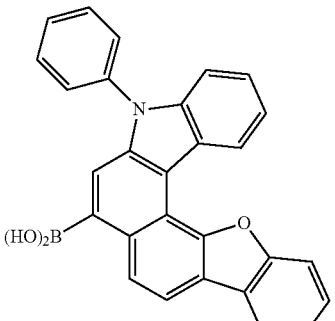

K

Synthesis of Intermediate L

<Step 2> Synthesis of Intermediate K

After 6.3 g (1 eq, 0.0115 mol) of Intermediate J was added to 150 ml of THF in a reaction vessel, the temperature of the reaction vessel was lowered to about −78° C. (using acetone and dry ice). After 30 minutes, 15.8 ml of n-BuLi (1.6M in Hex) was slowly added into the reaction vessel. After 1 hour, 20.1 ml of 2-isopropyl borate was slowly added into the reaction vessel.

The temperature was increased to room temperature, and then maintained for 1 hour for exchanging.

A reaction solution from complete reaction was washed with excess deionized water, and then with excess hexane to obtain 4.1 g of Intermediate K with a yield of about 72.7%.

GC-Mass (calc.: 427.14 g/mol, found: 426 g/mol)

<Step 2-1> Synthesis of Intermediate L 10 g (1 eq, 0.022 mol) of Intermediate K and 3.7 g (0.9 eq, 0.02 mol) of 2,4,6-trichloro-1,3,5-triazine were dissolved in 400 ml of toluene. 0.95 g (0.01 eq, 0.001 mmol) of Pd(PPh$_3$)$_4$ and 100 mL of a 2M K$_2$CO$_3$ saturated solution were added into the solution, and then heated while stirring for about 12 hours.

A reaction solution from complete reaction was filtered through Celite, and a filtered product was refined by column chromatography to obtain 6.63 g of Intermediate L with a yield of about 55.1%.

GC-Mass (calc.: 530.07 g/mol, found: 529 g/mol)

Next, Intermediate M was prepared from Intermediate L, as illustrated in Reaction Scheme 4.

Synthesis of Intermediate M 5.1 g of Intermediate M was synthesized from Intermediate L in the same manner as in the synthesis of Intermediate E (Yield: about 47%).

GC-Mass (calc.: 572.14 g/mol, found: 571 g/mol)

Synthesis of Compound 17

8.7 g of Compound 17 was synthesized from Intermediate L in the same manner as in the synthesis of Compound 1 (Yield: about 81%).

GC-Mass (calc.: 614.21 g/mol, found: 613 g/mol)

Elemental Analysis: C, 84.02; H, 4.26; N, 9.11; O, 2.60

Synthesis of Compound 21

7.7 g of Compound 21 was synthesized from Intermediate M in the same manner as in the synthesis of Compound 5 (Yield: about 73.6%).

GC-Mass (calc.: 720.2 g/mol, found: 719 g/mol)

Elemental Analysis: C, 81.64; H, 3.92; N, 7.77; O, 2.22; S, 4.45

Synthesis of Compound 33

8.3 g of Compound 33 was synthesized using pyres-1-yl boronic acid in the same manner as in the synthesis of Compound 21 (Yield: about 79.5%).

GC-Mass (calc.: 740.26 g/mol, found: 739 g/mol)

Elemental Analysis: C, 85.92; H, 4.35; N, 7.56; O, 2.16

Synthesis of Compound 37

7.9 g of Compound 37 was synthesized from Intermediate M in the same manner as in the synthesis of Compound 13 (Yield: about 69.1%).

GC-Mass (calc.: 764.26 g/mol, found: 763 g/mol)

Elemental Analysis: C, 86.37; H, 4.22; N, 7.33; O, 2.09

Synthesis of Compound 39

8.87 g of Compound 39 was synthesized using 9,9-dimethyl-9H-fluorene-2-yl boronic acid, instead of pyren-1-yl boronic acid, in the same manner as in the synthesis of Compound 33 (Yield: about 72.5%).

GC-Mass (calc.: 730.27 g/mol, found: 729 g/mol)

Elemental Analysis: C, 85.46; H, 4.69; N, 7.67; O, 2.19

Synthesis of Compound 40

7.14 g of Compound 40 was synthesized using dibenzo[b,d]furan-3-yl boronic acid, instead of pyren-1-yl boronic acid, in the same manner as in the synthesis of Compound 33 (Yield: about 62.5%).

GC-Mass (calc.: 704.22 g/mol, found: 703 g/mol)

Elemental Analysis: C, 83.51; H, 4.00; N, 7.95; O, 4.54

EXAMPLE 1

To manufacture an anode, a corning 15 Ω/cm$^2$ (500 Å) ITO glass substrate was cut to a size of 50 mm×50 mm×0.5 mm and then sonicated in isopropyl alcohol and in pure water each for five minutes, and then cleaned by ultrasonication, followed by ultraviolet (UV) irradiation, and exposure to ozone for washing. The resulting glass substrate was loaded into a vacuum deposition device.

2-TNATA was vacuum-deposited on the ITO glass substrate to form an HIL having a thickness of 600 Å on the anode, and then NPS was vacuum-deposited on the HIL to form an HTL having a thickness of 300 Å.

Ir(ppy)$_3$ as a green phosphorescent dopant and Compound 1 as a host were co-deposited on the HTL in a weight ratio of about 87:13 to form a green EML having a thickness of about 300 Å.

Alq3 was vacuum-deposited on the EML to form an ETL having a thickness of 300 Å.

Al was vacuum-deposited on the ETL to form a cathode having a thickness of about 1200 Å, thereby completing the manufacture of an organic light-emitting device.

EXAMPLE 2

An organic light-emitting device was manufactured in the same manner as in Example 1, except that Compound 2, instead of Compound 1, was used to form the EML.

EXAMPLE 3

An organic light-emitting device was manufactured in the same manner as in Example 1, except that Compound 5, instead of Compound 1, was used to form the EML.

EXAMPLE 4

An organic light-emitting device was manufactured in the same manner as in Example 1, except that Compound 7, instead of Compound 1, was used to form the EML.

EXAMPLE 5

An organic light-emitting device was manufactured in the same manner as in Example 1, except that Compound 8, instead of Compound 1, was used to form the EML.

EXAMPLE 6

An organic light-emitting device was manufactured in the same manner as in Example 1, except that Compound 11, instead of Compound 1, was used to form the EML.

EXAMPLE 7

An organic light-emitting device was manufactured in the same manner as in Example 1, except that Compound 12, instead of Compound 1, was used to form the EML.

EXAMPLE 8

An organic light-emitting device was manufactured in the same manner as in Example 1, except that Compound 13, instead of Compound 1, was used to form the EML.

EXAMPLE 9

An organic light-emitting device was manufactured in the same manner as in Example 1, except that Compound 17, instead of Compound 1, was used to form the EML.

EXAMPLE 10

An organic light-emitting device was manufactured in the same manner as in Example 1, except that Compound 21, instead of Compound 1, was used to form the EML.

EXAMPLE 11

An organic light-emitting device was manufactured in the same manner as in Example 1, except that Compound 33, instead of Compound 1, was used to form the EML.

EXAMPLE 12

An organic light-emitting device was manufactured in the same manner as in Example 1, except that Compound 37, instead of Compound 1, was used to form the EML.

EXAMPLE 13

An organic light-emitting device was manufactured in the same manner as in Example 1, except that Compound 39, instead of Compound 1, was used to form the EML.

EXAMPLE 14

An organic light-emitting device was manufactured in the same manner as in Example 1, except that Compound 40, instead of Compound 1, was used to form the EML.

EXAMPLE 15

An organic light-emitting device was manufactured in the same manner as in Example 1, except that Compound 53, instead of Compound 1, was used to form the EML.

COMPARATIVE EXAMPLE 1

An organic light-emitting device was manufactured in the same manner as in Example 1, except that CBP, instead of Compound 1, was used to form the EML.

EVALUATION EXAMPLE

Driving voltage, luminescent efficiency, color coordinates, luminocity, and lifetime of the OLEDs prepared according to Examples 1 to 15 and Comparative Example 1 were measured using a PR650 (Spectroscan) source measurement unit (available from PhotoResearch, Inc.). The results are shown in Table 1 below.

TABLE 1

| Example | Current density (mA/cm$^2$) | Driving voltage (V) | Luminescent efficiency (cd/A) | Color coordinates | Luminocity (cd/m$^2$) | T95 Half life-span (hr @ 100 mA/cm$^2$) |
|---|---|---|---|---|---|---|
| Example 1 | 5.4 | 4.0 | 71.2 | (0.32, 0.62) | 3,500 | 397 |
| Example 2 | 5.1 | 4.7 | 61.9 | (0.32, 0.63) | 3,500 | 332 |
| Example 3 | 5.5 | 4.9 | 61.7 | (0.33, 0.63) | 3,500 | 275 |
| Example 4 | 5.7 | 3.9 | 69.3 | (0.32, 0.61) | 3,500 | 259 |
| Example 5 | 5.4 | 4.2 | 68.2 | (0.33, 0.62) | 3,500 | 264 |

TABLE 1-continued

| Example | Current density (mA/cm²) | Driving voltage (V) | Luminescent efficiency (cd/A) | Color coordinates | Luminocity (cd/m²) | T95 Half life-span (hr @ 100 mA/cm²) |
|---|---|---|---|---|---|---|
| Example 6 | 5.9 | 4.1 | 66.6 | (0.31, 0.60) | 3,500 | 247 |
| Example 7 | 5.5 | 3.8 | 72.4 | (0.32, 0.60) | 3,500 | 219 |
| Example 8 | 5.4 | 3.7 | 65.5 | (0.32, 0.62) | 3,500 | 337 |
| Example 9 | 5.8 | 3.7 | 60.7 | (0.30, 0.62) | 3,500 | 356 |
| Example 10 | 5.2 | 4.2 | 62.9 | (0.31, 0.65) | 3,500 | 287 |
| Example 11 | 5.5 | 3.8 | 72.4 | (0.32, 0.60) | 3,500 | 225 |
| Example 12 | 5.4 | 3.7 | 65.5 | (0.32, 0.62) | 3,500 | 377 |
| Example 13 | 5.8 | 3.7 | 60.7 | (0.30, 0.62) | 3,500 | 295 |
| Example 14 | 5.2 | 4.2 | 62.9 | (0.31, 0.65) | 3,500 | 319 |
| Example 15 | 5.2 | 4.2 | 62.9 | (0.31, 0.65) | 3,500 | 278 |
| Comparative Example 1 | 6.2 | 5.1 | 51.2 | (0.32, 0.62) | 3,500 | 175 |

Referring to Table 1, the organic light-emitting devices of Examples 1 to 15 are found to have a lower driving voltage, an improved luminescent efficiency, and a considerably longer lifetime, as compared with the organic light-emitting device of Comparative Example 1.

In a quantitative comparison of the results, the organic light-emitting devices of Examples 1 to 15 had a lower driving voltage by about 15-25% and a higher luminescent efficiency by about 10-20%, as compared with the organic light-emitting device of Comparative Example 1. In particular, in terms of life time characteristics, the organic light-emitting devices of Examples 1 to 15 were found to have an increase in lifetime (T95) of about 35-130%, relative to the organic light-emitting device of Comparative Example 1. This is attributed to the high thermal stability of the fused ring compound of Formula 1 used in the organic light-emitting devices of Examples 1 to 15.

As described above, according to the one or more embodiments of the present invention, a fused ring compound of Formula 1 has high thermal resistance, and may improve luminosity and lifetime of an organic light-emitting device when used in an organic layer of the organic light-emitting device.

The organic light-emitting device may have a higher luminescent efficiency, as compared with an existing organic light-emitting device, and may have an increased lifetime due to improved lifetime characteristics of the fused ring compound used in the organic layer.

An organic light-emitting display apparatus including the organic light-emitting device may have an increased lifetime and an increased power efficiency with reduced power consumption.

While the present invention has been particularly shown and described with reference to exemplary embodiments thereof, it will be understood by those of ordinary skill in the art that various changes in form and details may be made therein without departing from the spirit and scope of the present invention as defined by the following claims, and equivalents thereof.

What is claimed is:

1. A fused ring compound represented by Formula 1 below:

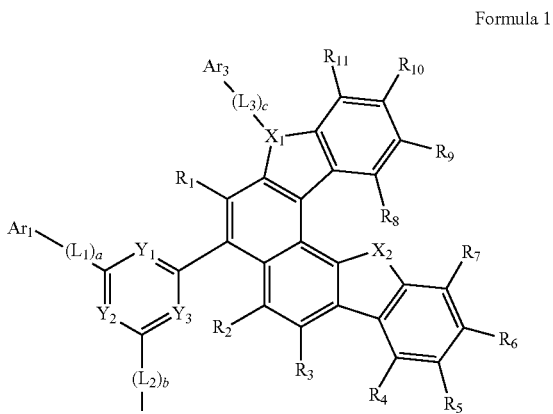

Formula 1 wherein, in Formula 1, $X_1$ is a nitrogen atom (N);

$X_2$ is one of S, O, $Si(R_{12})(R_{13})$, or $N(R_{14})$;

$Y_1$ to $Y_3$ are each independently one of C or N, wherein at least one of $Y_1$ to $Y_3$ is N;

$Ar_1$ to $Ar_3$ are each independently selected from the group consisting of a substituted or unsubstituted $C_6$-$C_{40}$ aryl group, a substituted or unsubstituted $C_6$-$C_{40}$ arylalkyl, a substituted or unsubstituted $C_6$-$C_{40}$ aryloxy group, a substituted or unsubstituted $C_6$-$C_{40}$ arylthio group, a substituted or unsubstituted $C_6$-$C_{40}$ arylamino group, and a substituted or unsubstituted $C_2$-$C_{40}$ heteroaryl group;

$R_1$ to $R_{14}$ are each independently a hydrogen atom, a deuterium atom, a halogen atom, a hydroxyl group, a cyano group, a nitro group, an amino group, a carboxyl group, a substituted or unsubstituted $C_1$-$C_{40}$ alkyl group, a substituted or unsubstituted $C_1$-$C_{40}$ alkoxy group, a substituted or unsubstituted $C_2$-$C_{40}$ alkenyl group, a substituted or unsubstituted $C_2$-$C_{40}$ alkynyl group, a substituted or unsubstituted $C_3$-$C_{40}$ cycloalkyl group, a substituted or unsubstituted $C_3$-$C_{40}$ cycloalkenyl group, a substituted or unsubstituted $C_6$-$C_{40}$ aryl group, a substituted or unsubstituted $C_6$-$C_{40}$ arylalkyl group, a substituted or unsubstituted $C_6$-$C_{40}$ aryloxy group, a substituted or unsubstituted $C_6$-$C_{40}$ arylthio group, a substituted or unsubstituted $C_6$-$C_{40}$ arylamino group, or a substituted or unsubstituted $C_2$-$C_{40}$ heteroaryl group, wherein at least two adjacent groups of $R_1$ to $R_{14}$ are optionally fused;

$L_1$ to $L_3$ are each independently a substituted or unsubstituted $C_6$-$C_{40}$ arylene group; and a, b and c are each independently an integer from 0 to 3.

2. The fused ring compound of claim 1, wherein $X_2$ is one of S, O, or $Si(R_{12})(R_{13})$.

3. The fused ring compound of claim 1, wherein $Y_1$ and $Y_2$ are each N, and $Y_3$ is C; $Y_1$ and $Y_3$ are each N, and $Y_2$ is C; $Y_2$ and $Y_3$ are each N, and $Y_1$ is C; or $Y_1$, $Y_2$, and $Y_3$ are each N.

4. The fused ring compound of claim 1, wherein $Y_1$ and $Y_3$ are each N, and $Y_2$ is C; or $Y_1$, $Y_2$, and $Y_3$ are each N.

5. The fused ring compound of claim 1, wherein the fused ring compound is represented by one of Formulae 2a to 2f below:

Formula 2a

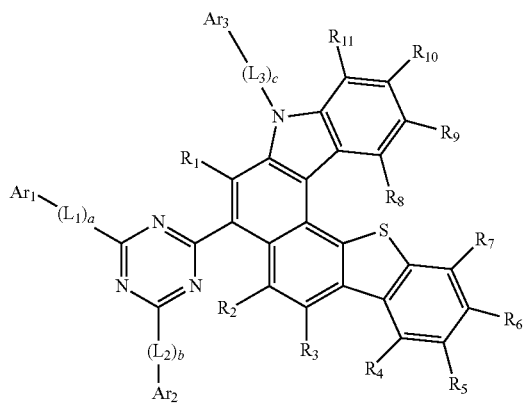

Formula 2b

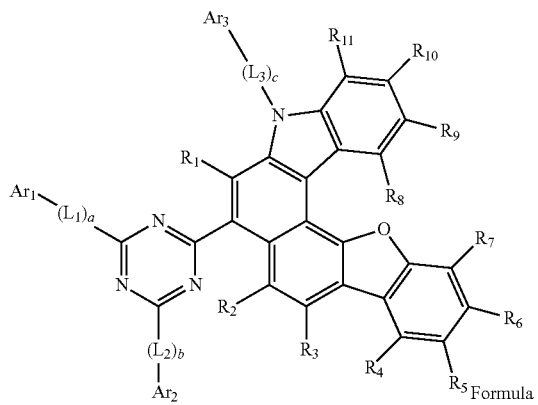

Formula 2c

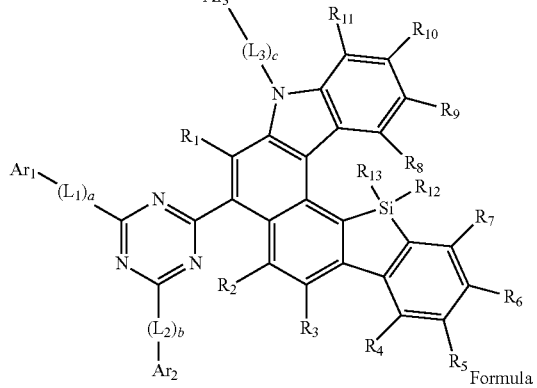

Formula 2d

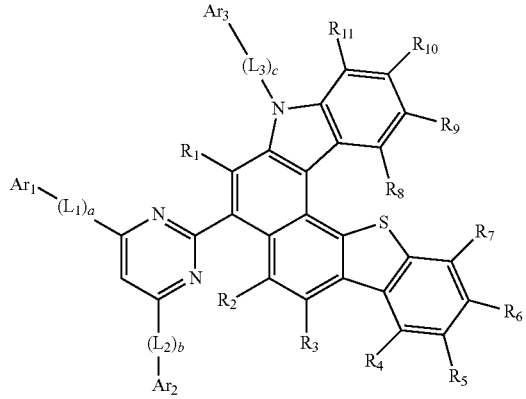

Formula 2e

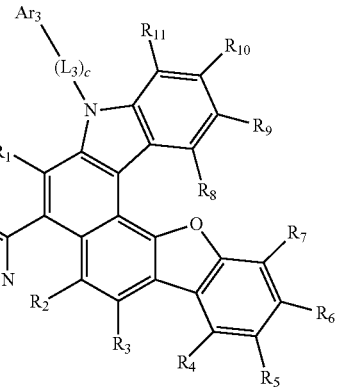

Formula 2f

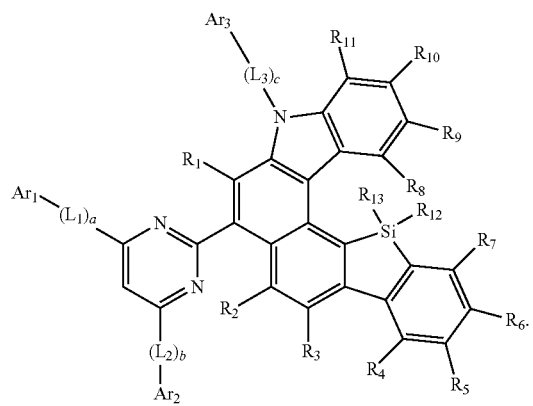

6. The fused ring compound of claim 1, wherein $Ar_1$ to $Ar_3$ are each independently one of a substituted or unsubstituted $C_6$-$C_{40}$ aryl group, or a substituted or unsubstituted $C_2$-$C_{40}$ heteroaryl group;

$L_1$ to $L_3$ are each independently one of a substituted or unsubstituted phenylene group, or a substituted or unsubstituted naphthalene group; and a, b and c are each independently an integer from 0 to 1.

7. The fused ring compound of claim 1, wherein $Ar_1$ to $Ar_3$ are each independently one of a substituted or unsubstituted phenyl group, a substituted or unsubstituted naphthyl group, a substituted or unsubstituted anthryl group, a substituted or unsubstituted phenanthrenyl group, a substituted or unsubstituted phenalenyl group, a substituted or unsubstituted pyrenyl group, a substituted or unsubstituted chrysenyl group, a substituted or unsubstituted triphenylenyl group, a substituted or unsubstituted tetracenyl group, a substituted or unsubstituted tetraphenyl group, a substituted or unsubstituted benzoanthryl group, a substituted or unsubstituted benzophenanthrenyl group, a substituted or unsubstituted biphenyl group, a substituted or unsubstituted terphenyl group, a substituted or unsubstituted indenyl group, a substituted or unsubstituted fluorenyl group, a substituted or unsubstituted benzofluorenyl group, a substituted or unsubstituted fluoranthenyl group, a substituted or unsubstituted benzothiophenyl group, a substituted or unsubstituted dibenzothiophenyl group, a substituted or unsubstituted benzonaphthothiophenyl group, a substituted or unsubstituted benzofuranyl group, a substituted or unsubstituted dibenzofuranyl group, a substituted or unsubstituted benzonaphthofuranyl group, a substituted or unsubstituted benzosilolyl group, a substituted or unsubstituted dibenzosilolyl group, a substituted or unsubstituted benzonaphthosilolyl group, a substituted or unsubstituted indolyl group, a substituted or unsubstituted carbazolyl group, a substituted or unsubstituted benzocarbazolyl group, a substituted or unsubstituted quinolinyl group, a substituted or unsubstituted acridinyl group, a substituted or unsubstituted isoquinolinyl group, or a substituted or unsubstituted benzoisoquinolinyl group;

- $L_1$ to $L_3$ are each independently one of a substituted or unsubstituted phenylene group, or a substituted or unsubstituted naphthalene group; and
- a, b and c are each independently an integer from 0 to 1.

8. The fused ring compound of claim 1, wherein $Ar_1$ to $Ar_3$ are each independently one of a substituted or unsubstituted phenyl group, a substituted or unsubstituted naphthyl group, a substituted or unsubstituted anthryl group, a substituted or unsubstituted phenanthrenyl group, a substituted or unsubstituted phenalenyl group, a substituted or unsubstituted pyrenyl group, a substituted or unsubstituted chrycenyl group, a substituted or unsubstituted triphenylenyl group, a substituted or unsubstituted tetracenyl group, a substituted or unsubstituted tetraphenyl group, a substituted or unsubstituted benzoanthryl group, a substituted or unsubstituted benzophenanthrenyl group, a substituted or unsubstituted indenyl group, a substituted or unsubstituted fluorenyl group, a substituted or unsubstituted benzothiophenyl group, a substituted or unsubstituted dibenzothiophenyl group, a substituted or unsubstituted benzofuranyl group, a substituted or unsubstituted dibenzofuranyl group, a substituted or unsubstituted benzosilol group, a substituted or unsubstituted dibenzosilol group, a substituted or unsubstituted indolyl group, a substituted or unsubstituted carbazolyl group, a substituted or unsubstituted quinolinyl group, or a substituted or unsubstituted acridinyl group;

- $L_1$ to $L_3$ are each independently one of a substituted or unsubstituted phenylene group, or a substituted or unsubstituted naphthalene group; and
- a, b and c are each independently an integer from 0 to 1.

9. The fused ring compound of claim 2, wherein $Ar_1$ to $Ar_3$ are each independently represented by one of Formulae 3a to 3m below:

Formula 3a

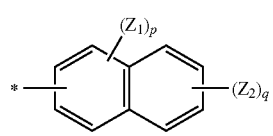

Formula 3b

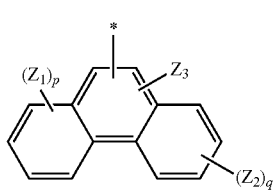

Formula 3c

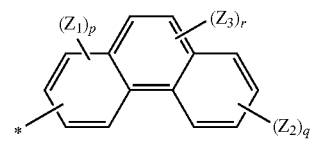

Formula 3d

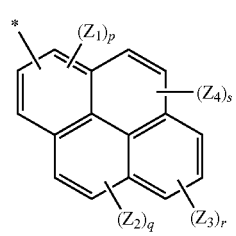

Formula 3e

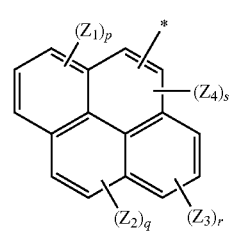

Formula 3f

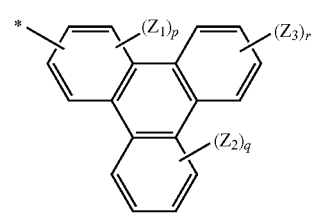

Formula 3g

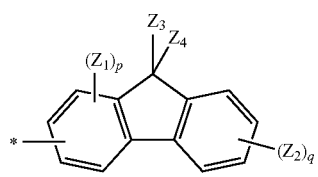

Formula 3h

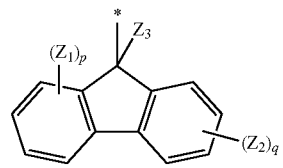

Formula 3i

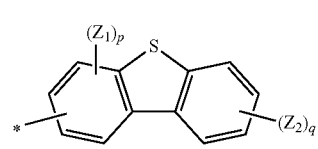

Formula 3j

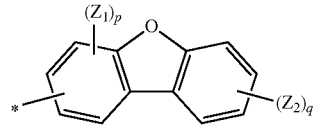

Formula 3k

Formula 3l

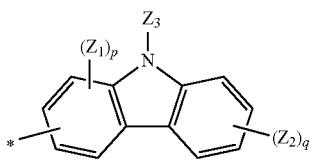

Formula 3m

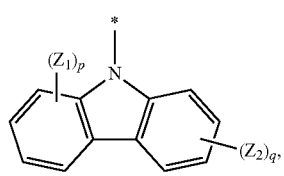

wherein in Formulae 3a to 3m, $Z_1$ to $Z_4$ are each independently one of a hydrogen atom, a deuterium atom, a halogen atom, a hydroxyl group, a cyano group, a nitro group, an amino group, a carboxyl group, a substituted or unsubstituted methyl group, a substituted or unsubstituted ethyl group, a substituted or unsubstituted propyl group, a substituted or unsubstituted butyl group, or a substituted or unsubstituted phenyl group;

p, q, r and s are each independently an integer from 1 to 5; and

* indicates a binding site with residue of the fused ring compound represented by Formula 1 excluding the moieties represented by Formulae 3a to 3m.

10. The fused ring compound of claim 8, wherein $Ar_1$ to $Ar_3$ are each independently represented by one of Formulae 4a to 4j below:

Formula 4a

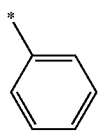

Formula 4b

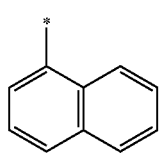

Formula 4c

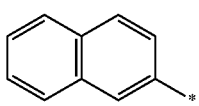

Formula 4d

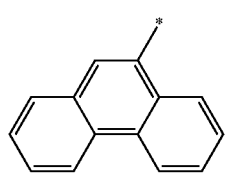

Formula 4e

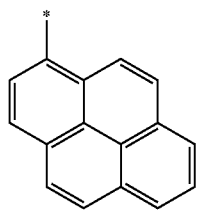

Formula 4f

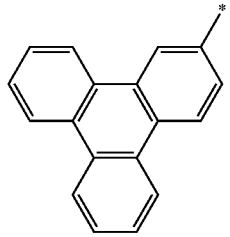

Formula 4g

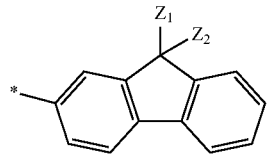

Formula 4h

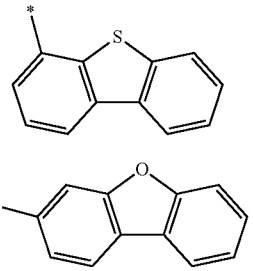

Formula 4i

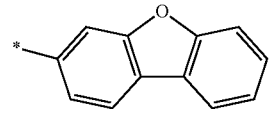

Formula 4j

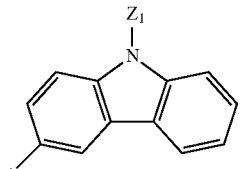

wherein, in Formulae 4a to 4j, $Z_1$ and $Z_2$ are each independently one of a hydrogen atom, a deuterium atom, a halogen atom, a hydroxyl group, a cyano group, a nitro group, an amino group, a carboxyl group, a substituted or unsubstituted methyl group, a substituted or unsubstituted ethyl group, a substituted or unsubstituted propyl group, a substituted or unsubstituted butyl group, or a substituted or unsubstituted phenyl group; and

* indicates a binding site with residue of the fused ring compound represented by Formula 1 excluding the moieties represented by Formulae 3a to 3m.

11. The fused ring compound of claim 1, wherein $R_1$ to $R_{14}$ are each independently one of a hydrogen atom, a deuterium atom, a substituted or unsubstituted methyl group, a substituted or unsubstituted ethyl group, a substituted or unsubstituted propyl group, a substituted or unsubstituted butyl group, or a substituted or unsubstituted phenyl group.

12. The fused ring compound of claim 1, wherein the fused ring compound is one of compounds 1 to 96 below:

-continued
1
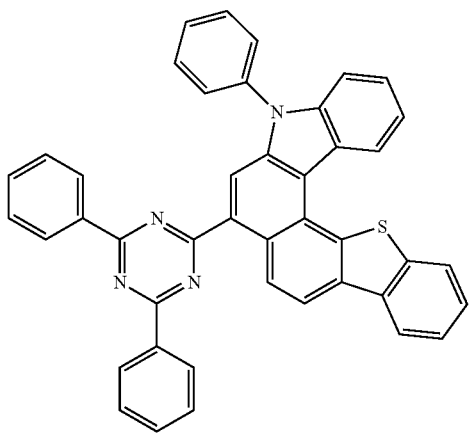
2
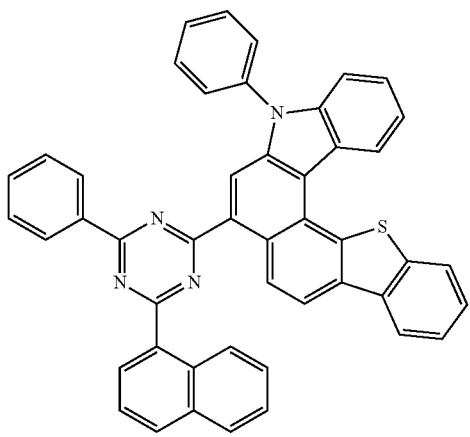
3
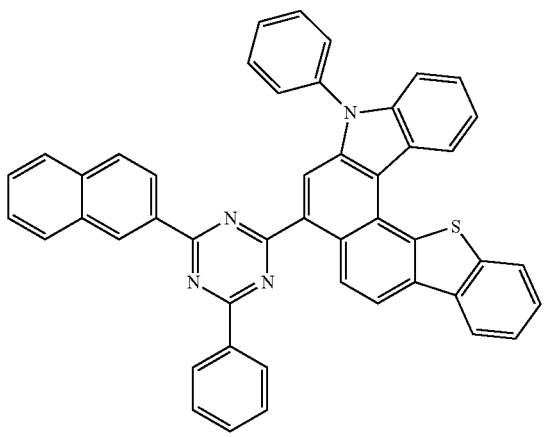
4
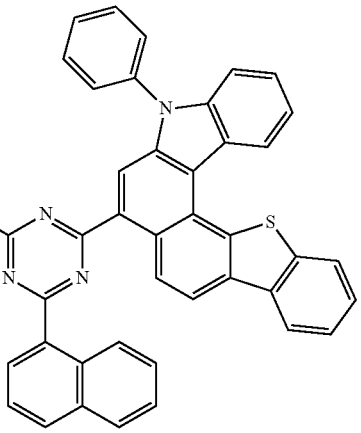
5
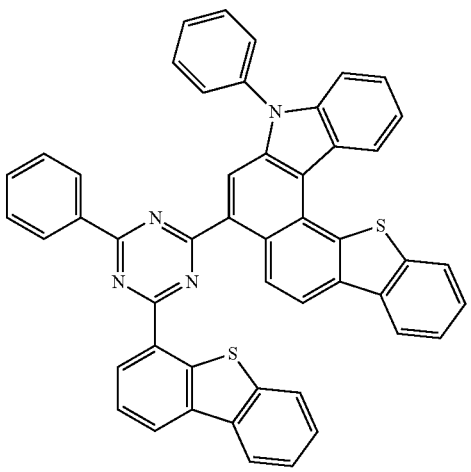
6
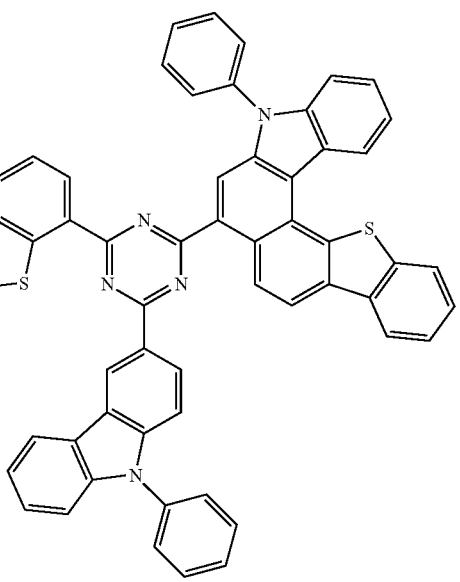

77
-continued
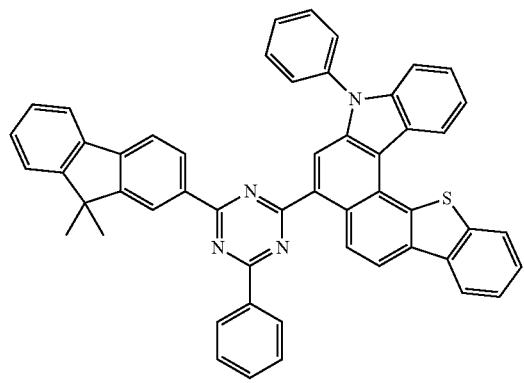
7
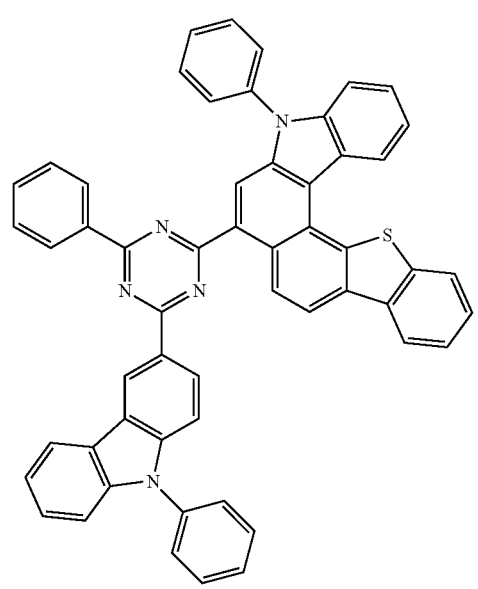
8
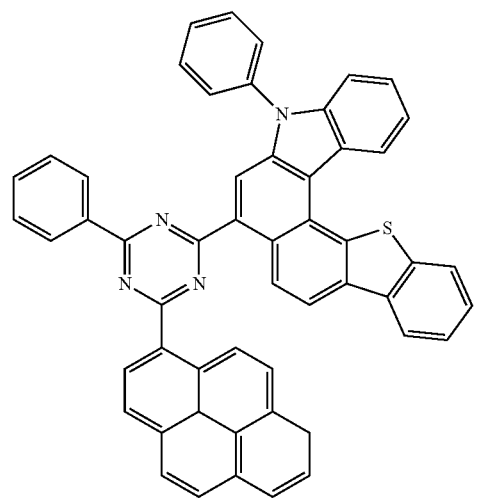
9
78
-continued
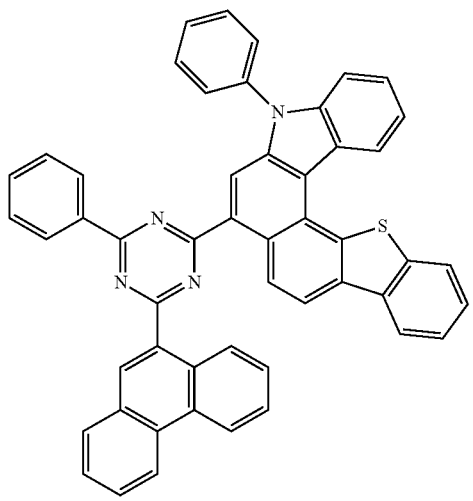
10
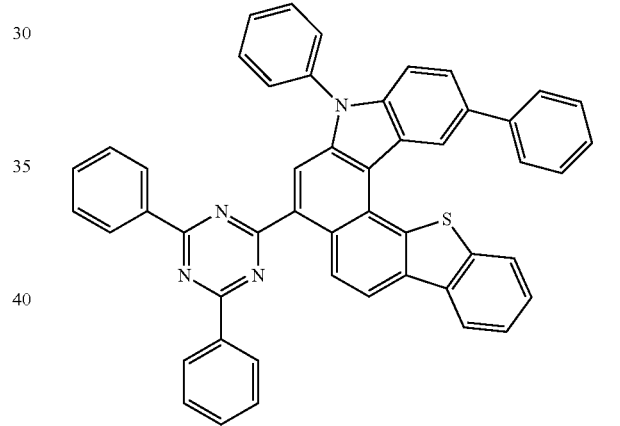
11
12

79
-continued
13
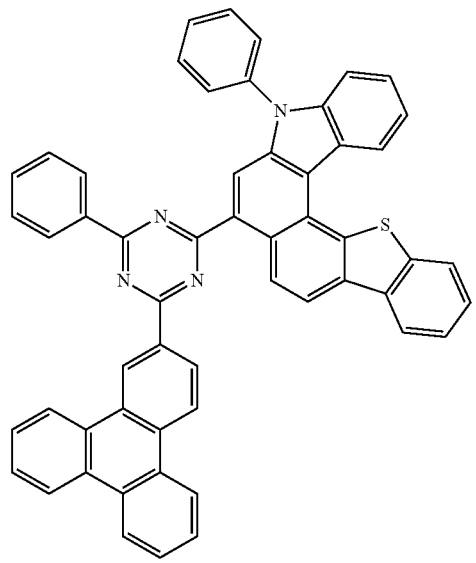
14
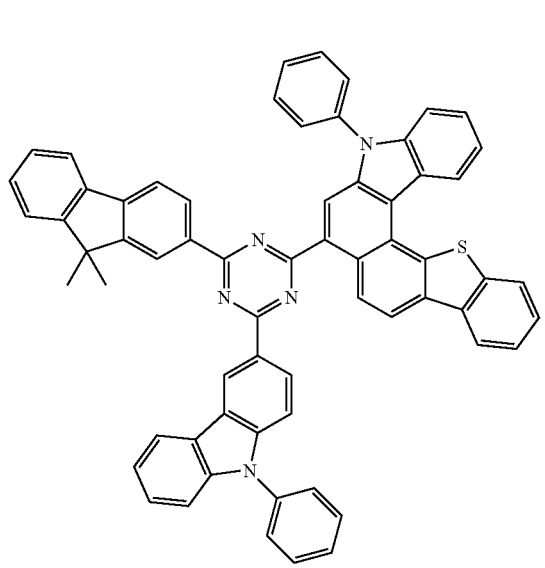
15
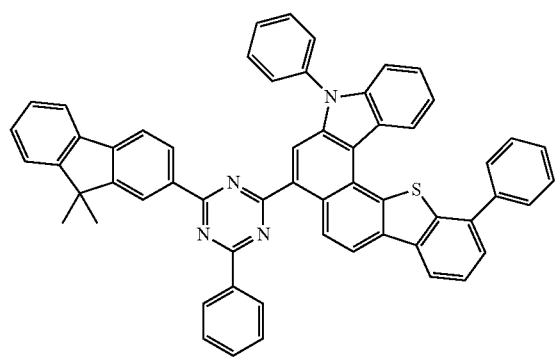
80
-continued
16
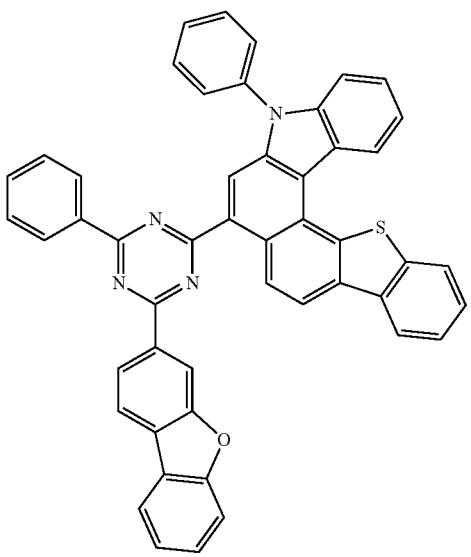
17
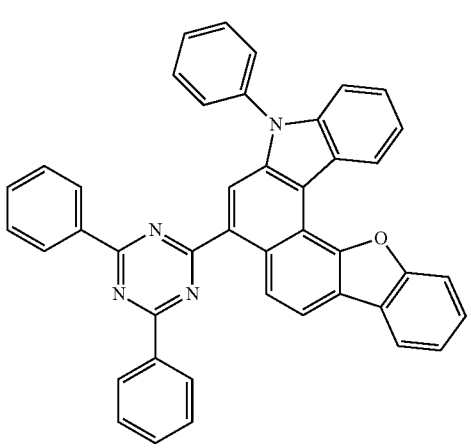
18
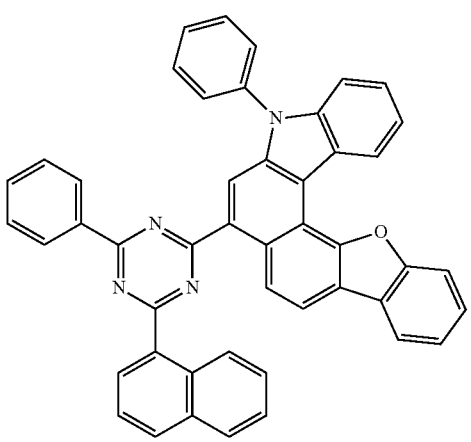

19
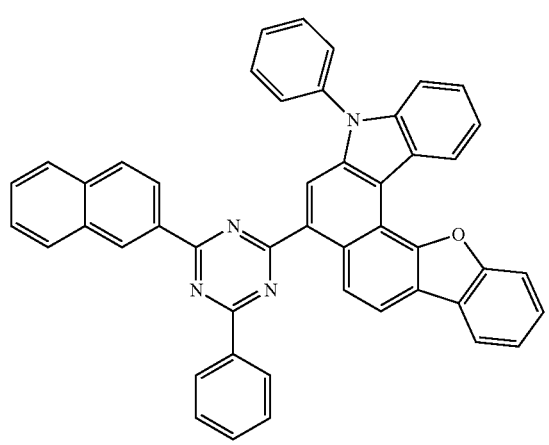
20
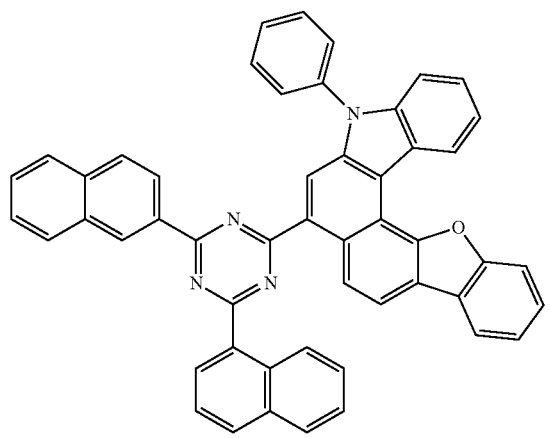
21
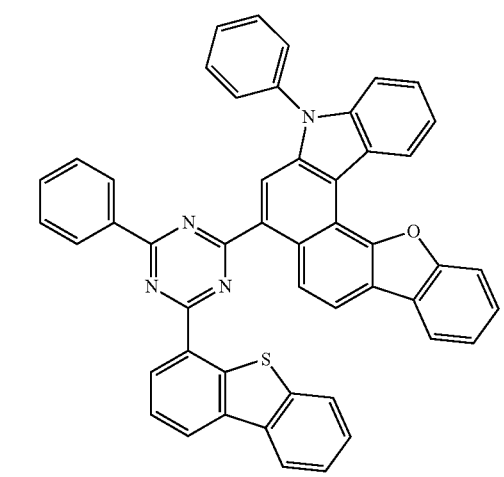
22
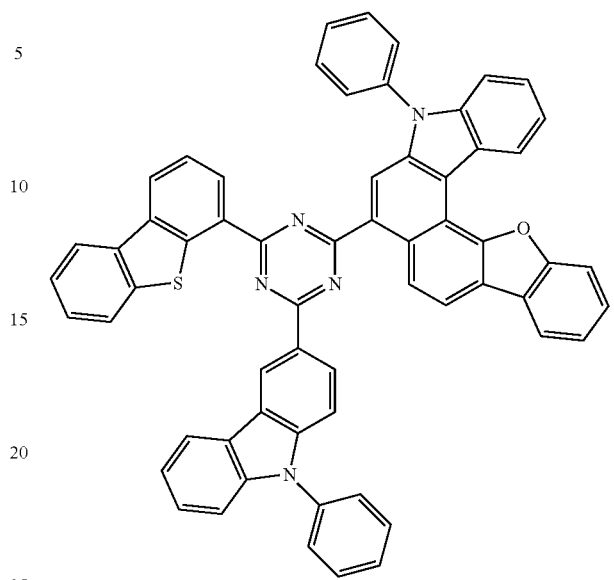
23
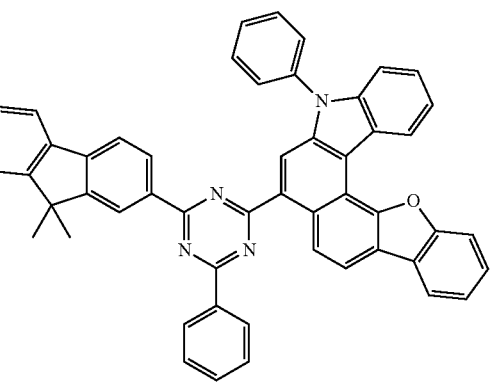
24
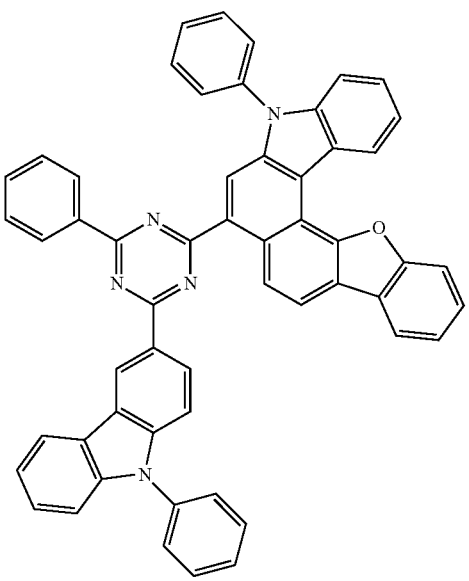

25
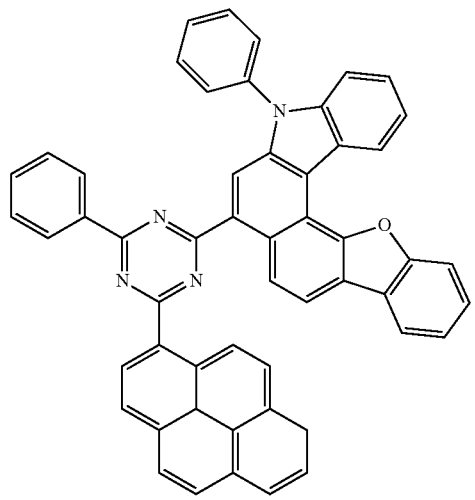
26
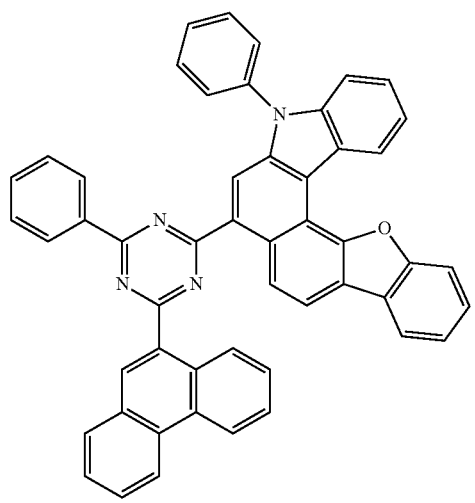
27
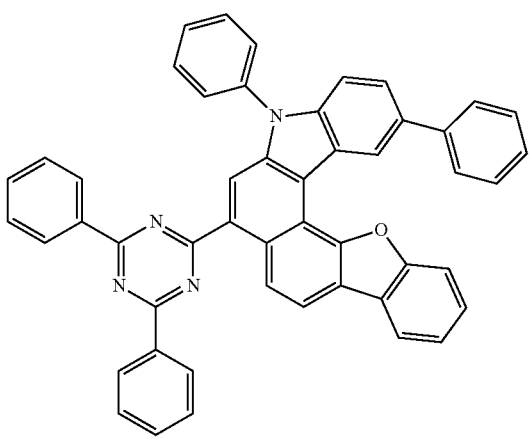
28
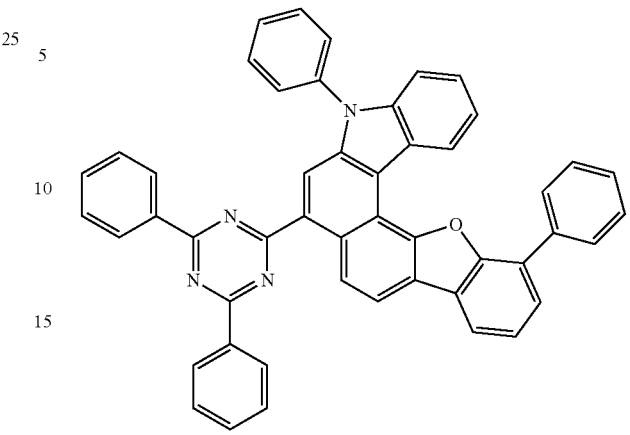
29
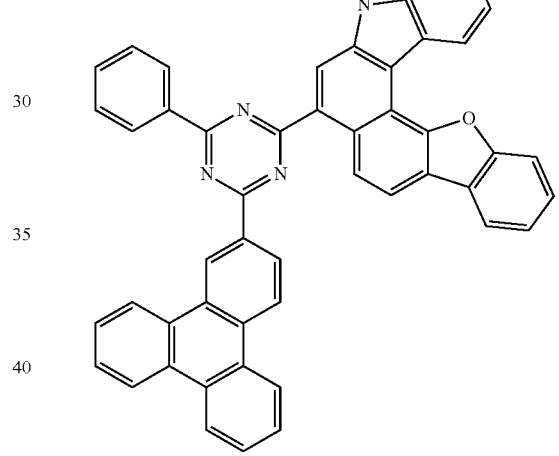
30
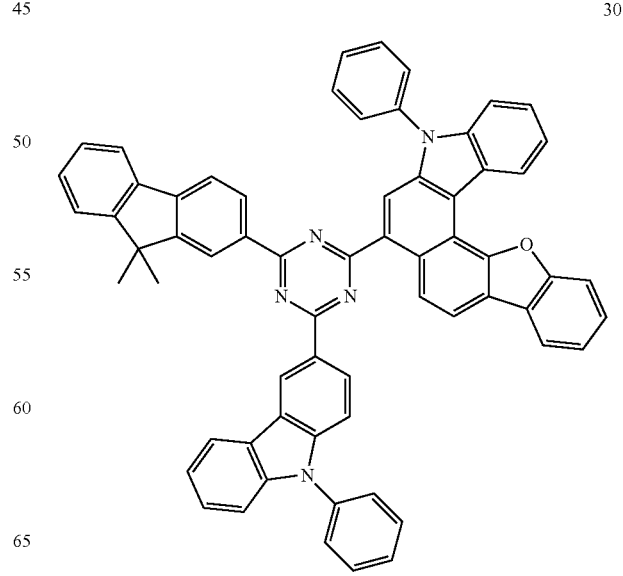

31
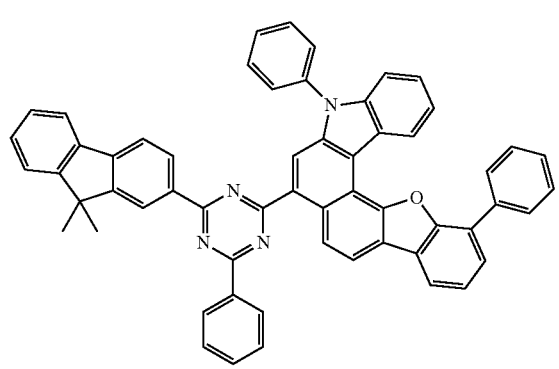
32
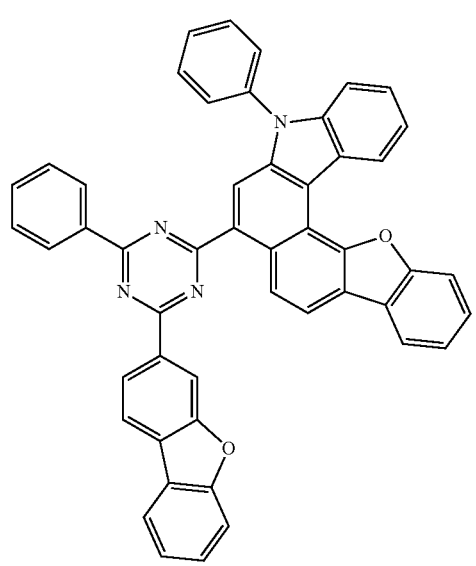
33
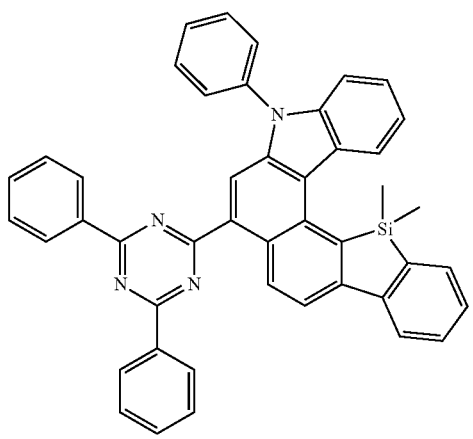
34
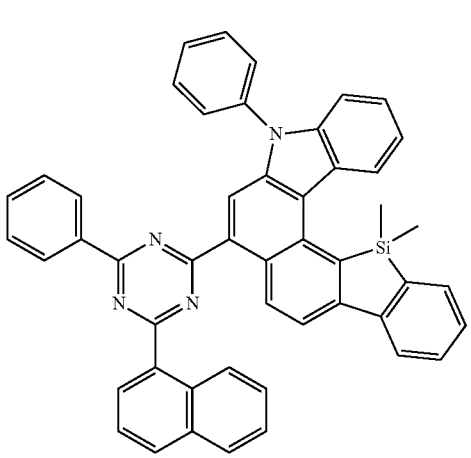
35
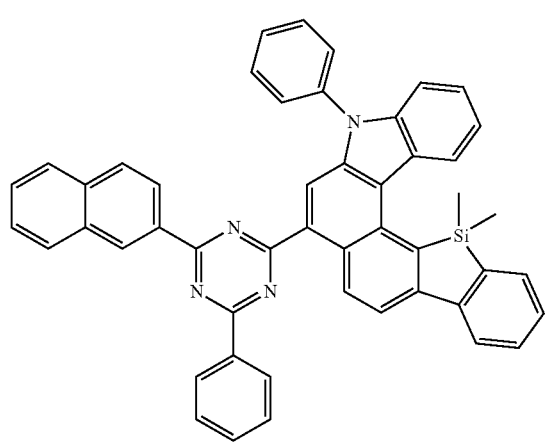
36
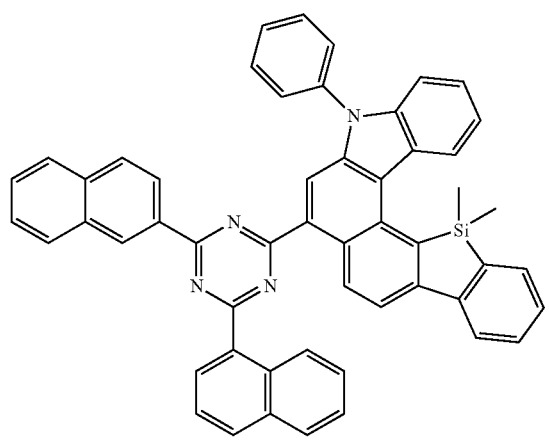

87
-continued
37
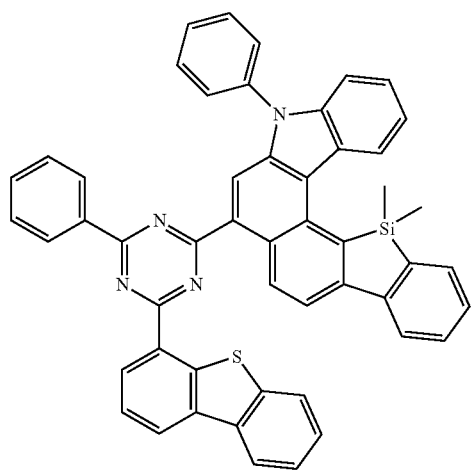
38
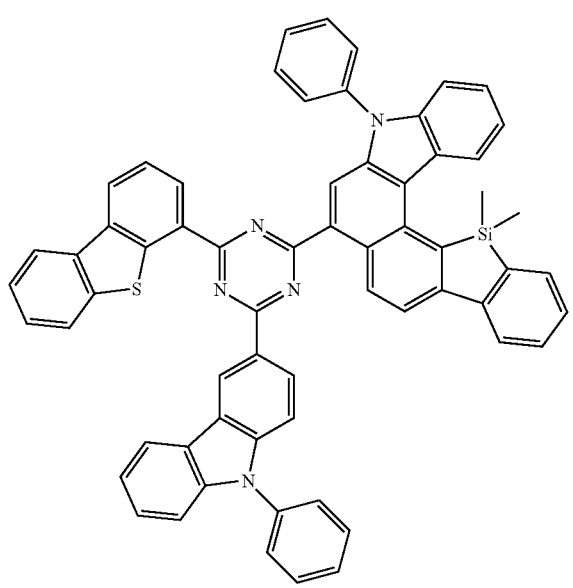
39
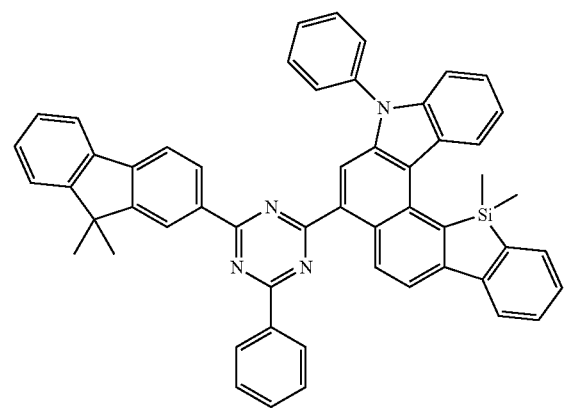
88
-continued
40
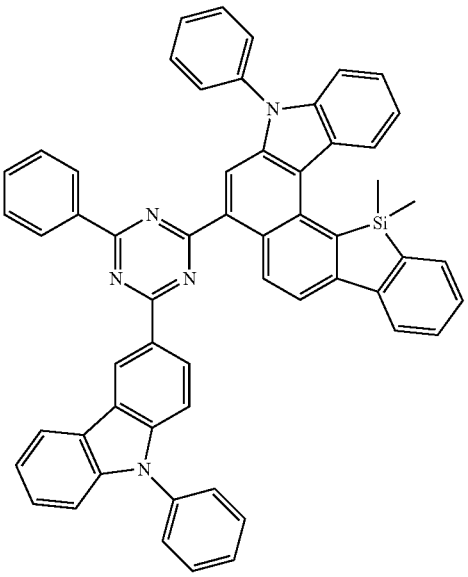
41
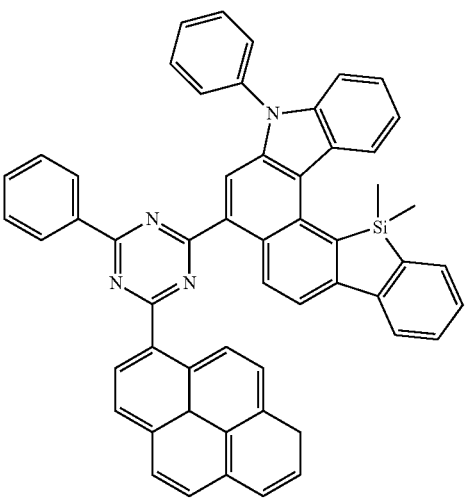
42
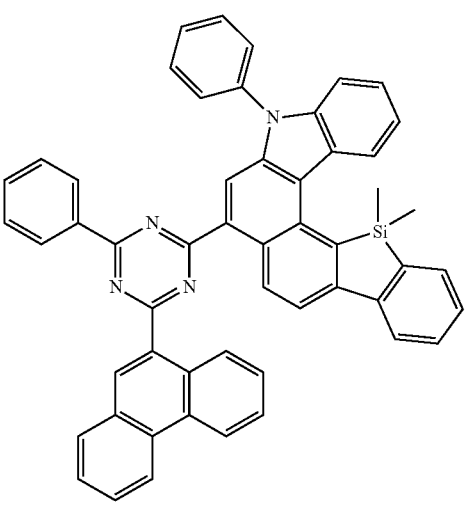

43
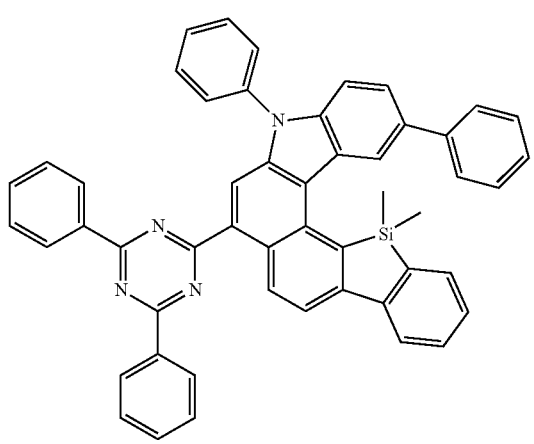
44
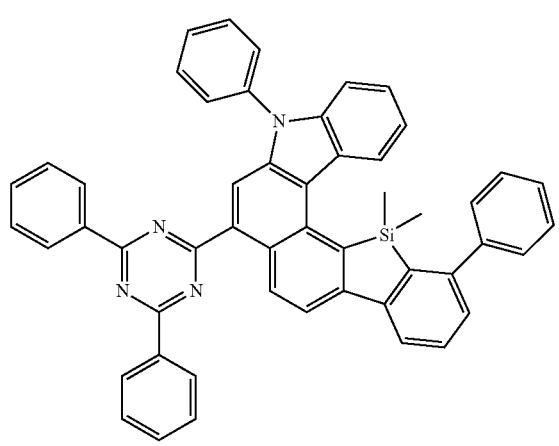
45
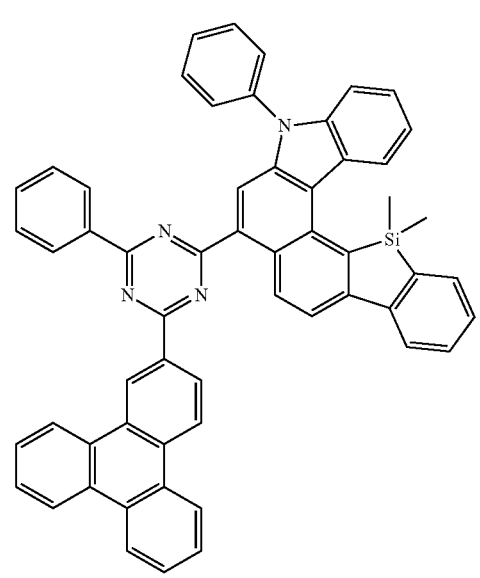
46
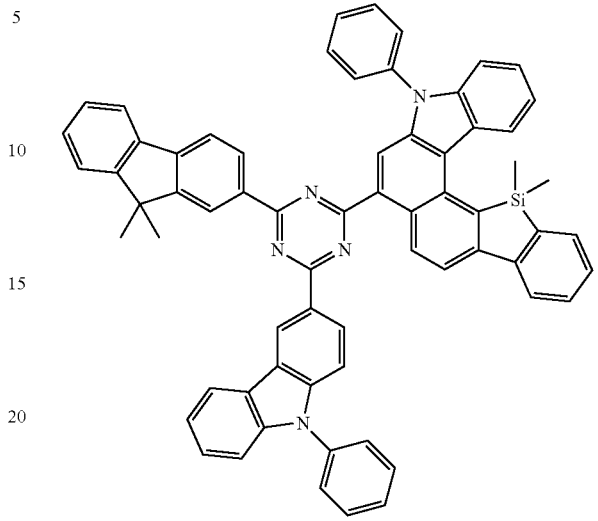
47
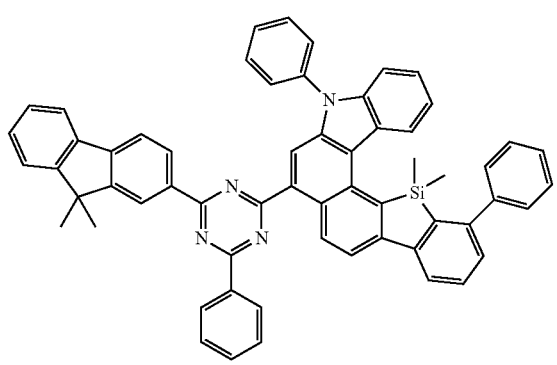
48
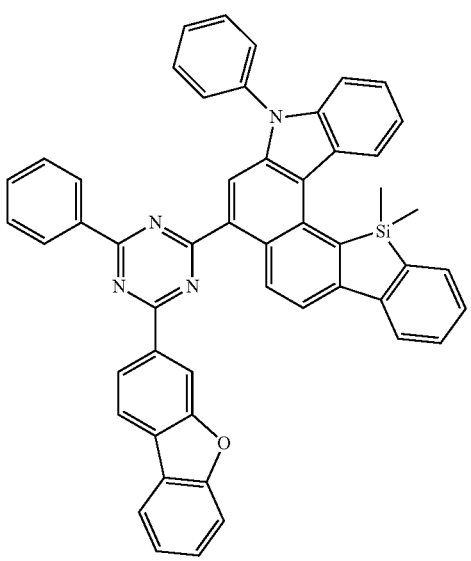

| 49 | 52 |
|---|---|
| 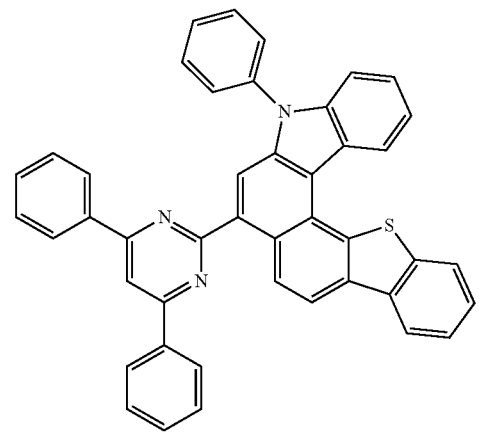 | 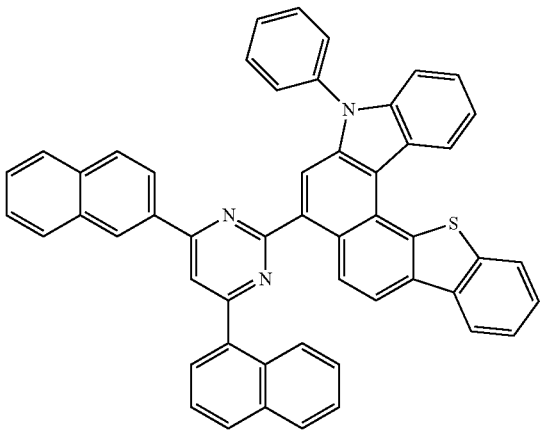 |
| 50 | 53 |
| 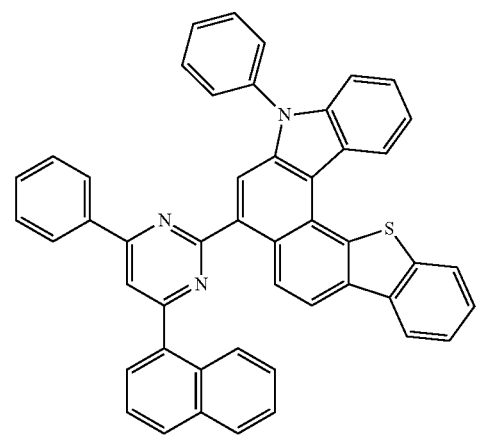 | 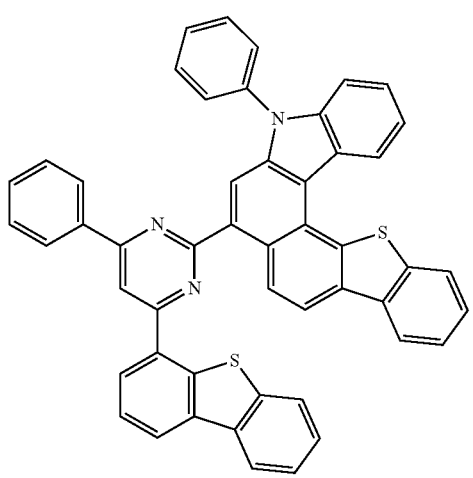 |
| 51 | 54 |
| 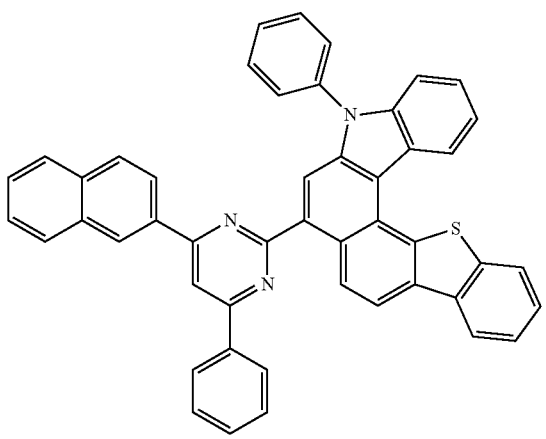 | 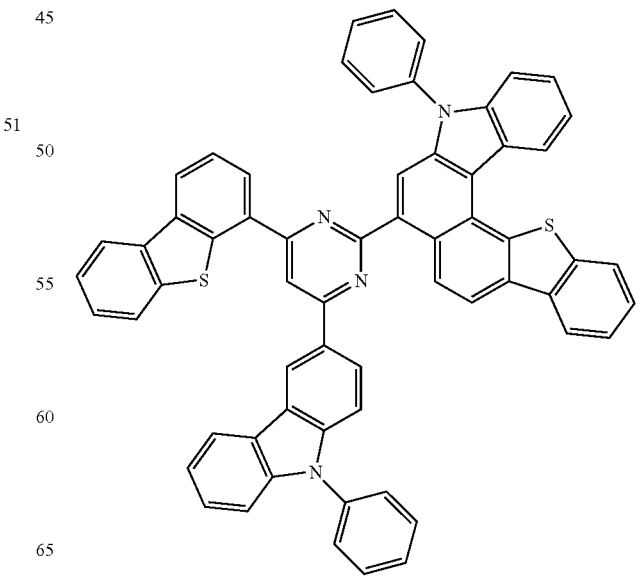 |

93
-continued
55
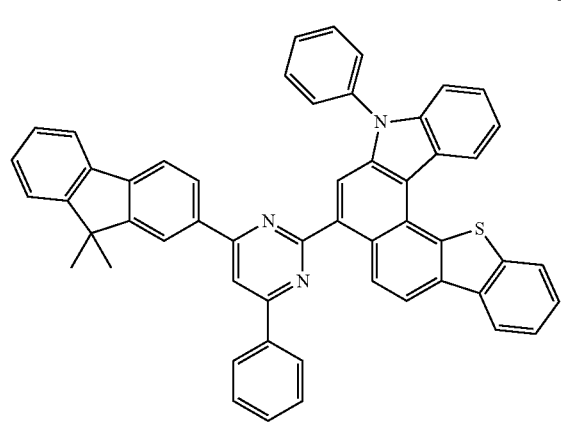
56
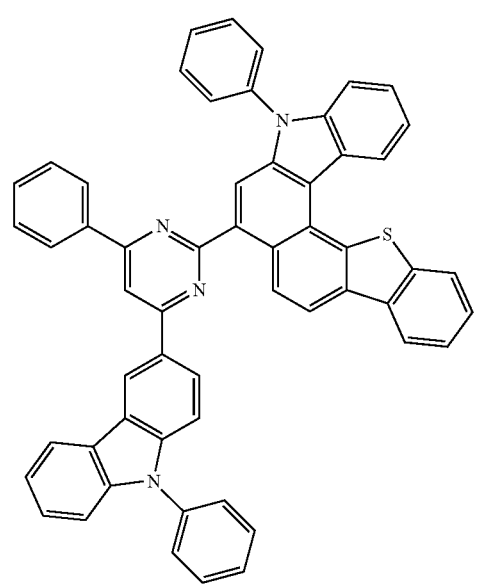
57
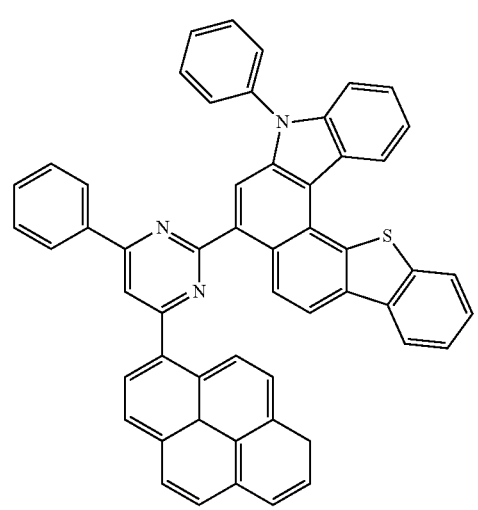
94
-continued
58
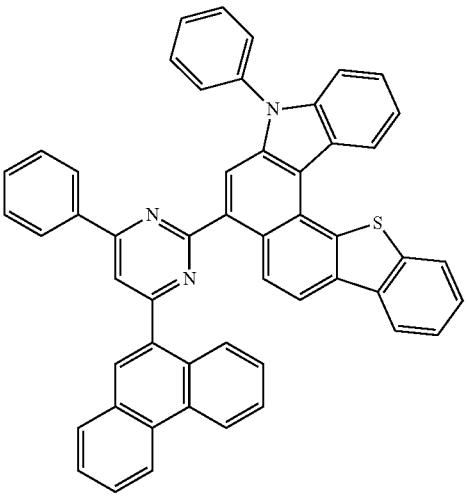
59
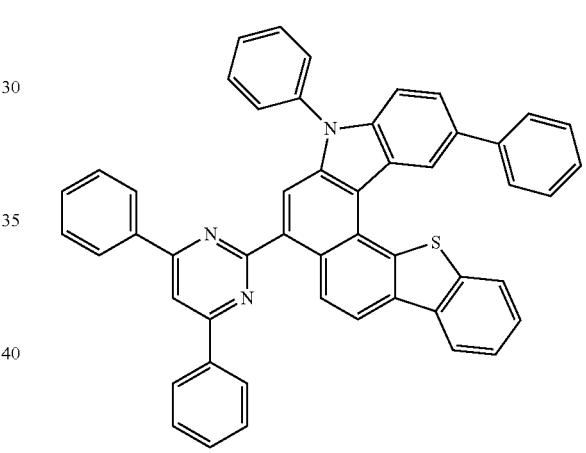
60
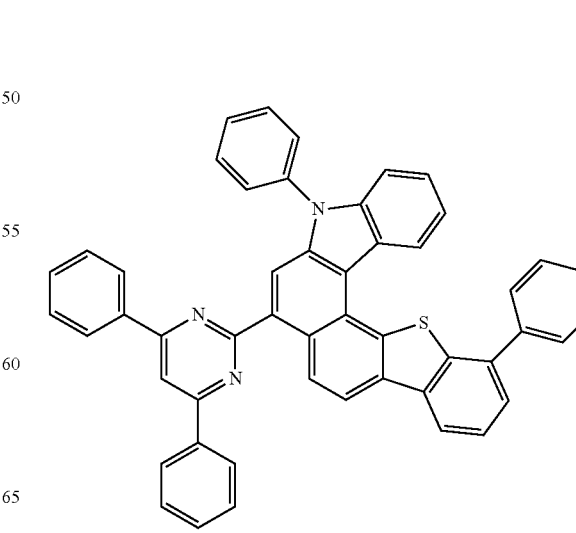

61
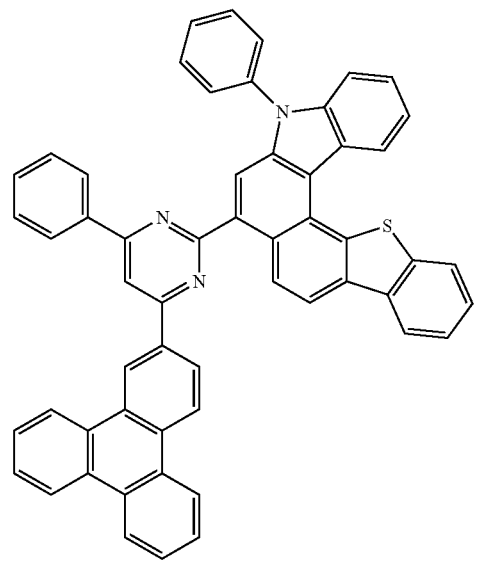
62
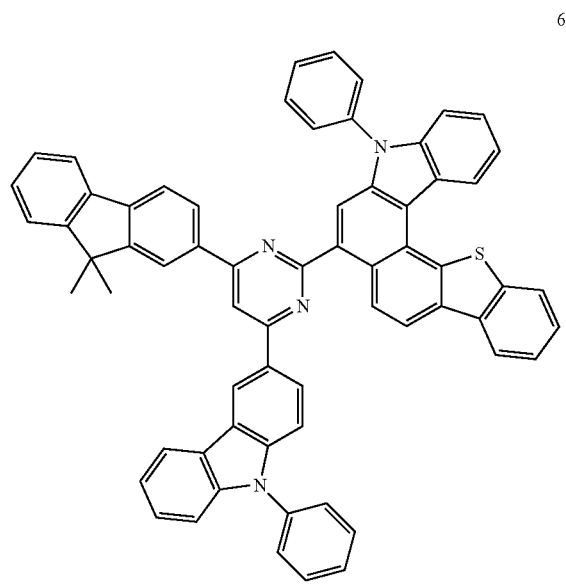
63
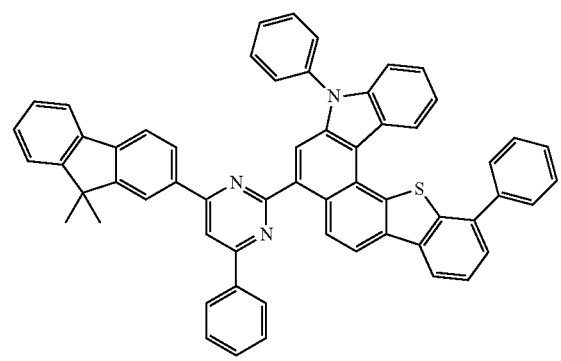
64
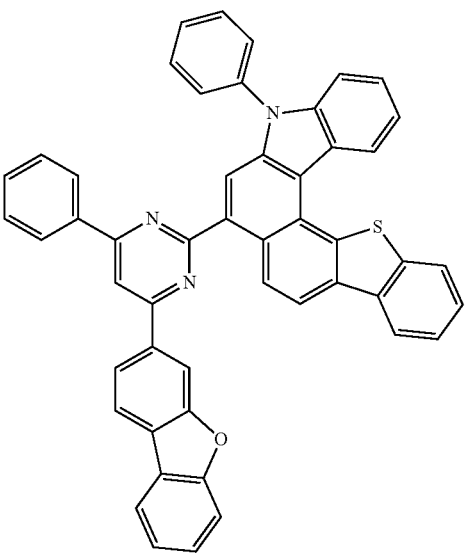
65
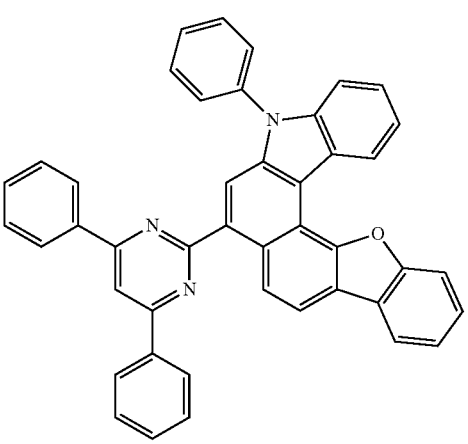
66
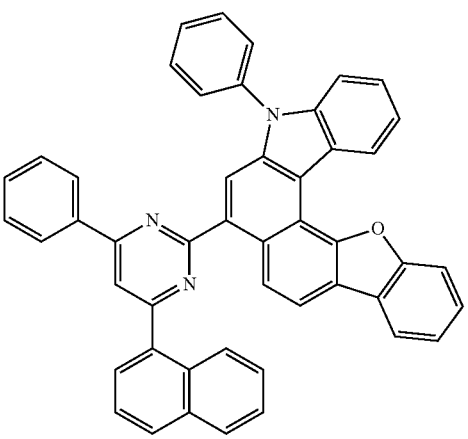

97
-continued
67
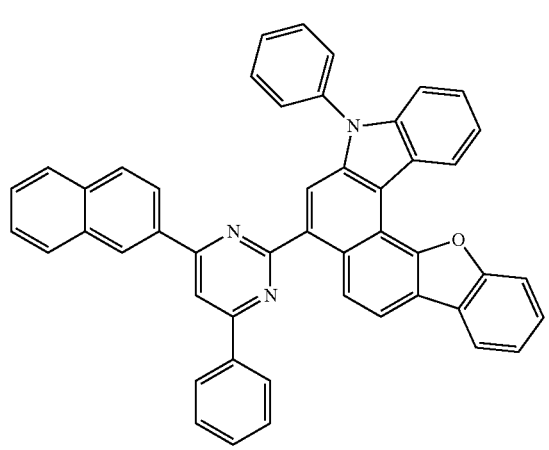
68
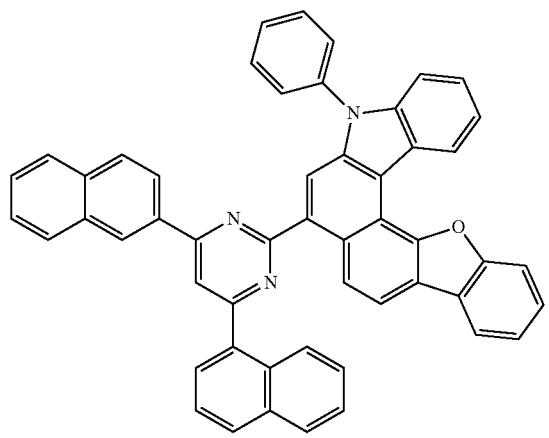
69
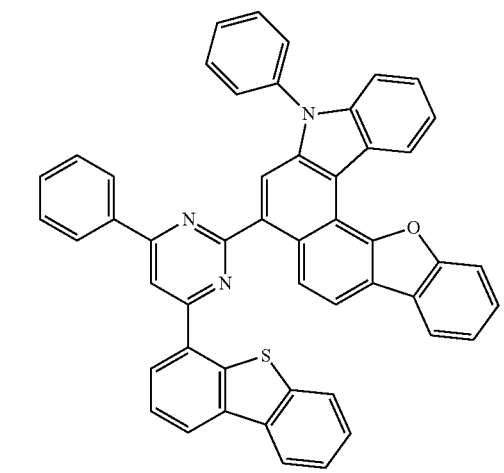
98
-continued
70
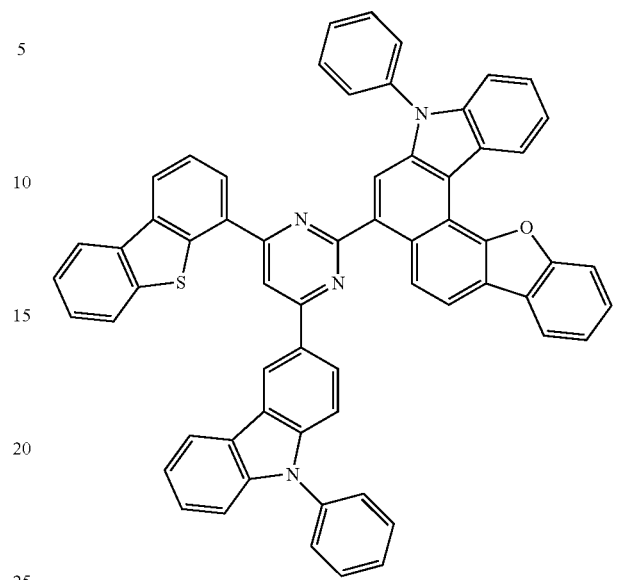
71
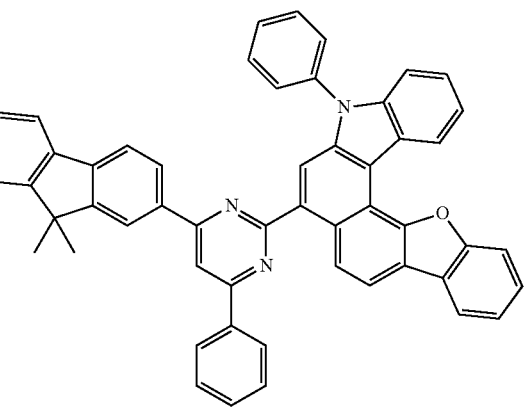
72
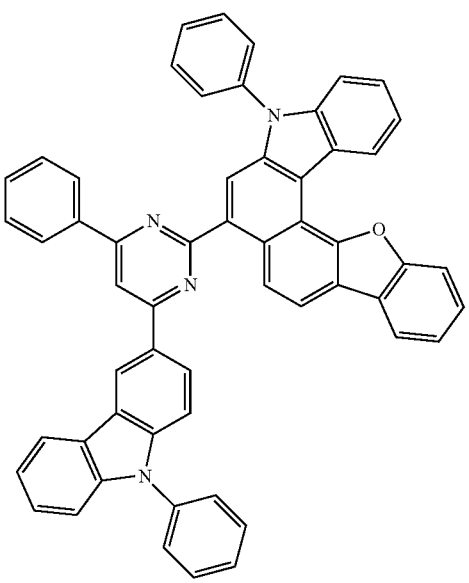

99
-continued
73
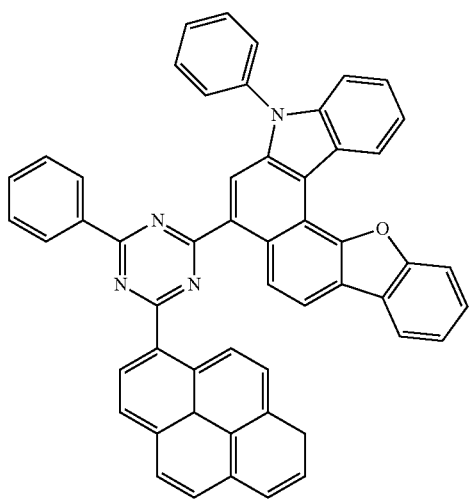
74
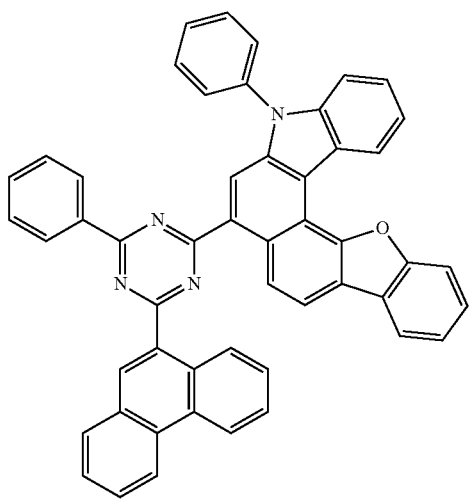
75
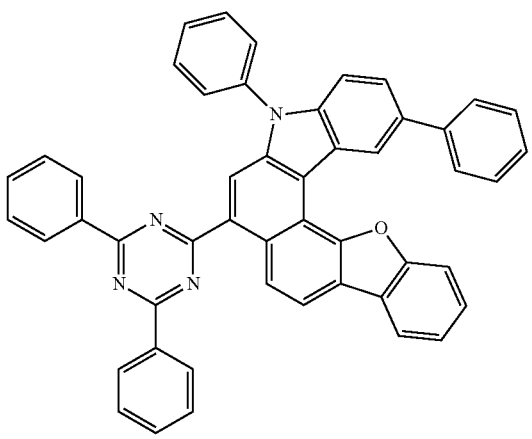
100
-continued
76
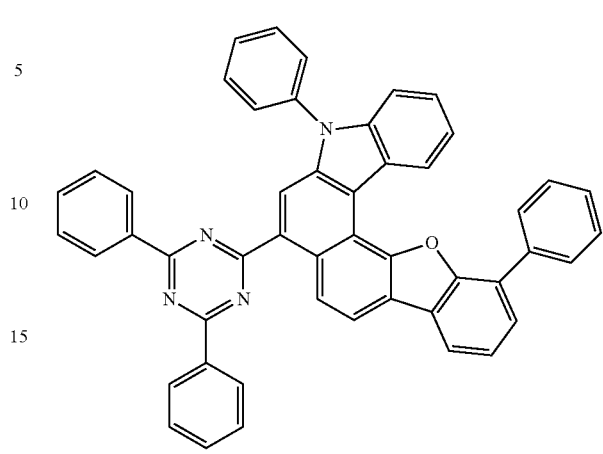
77
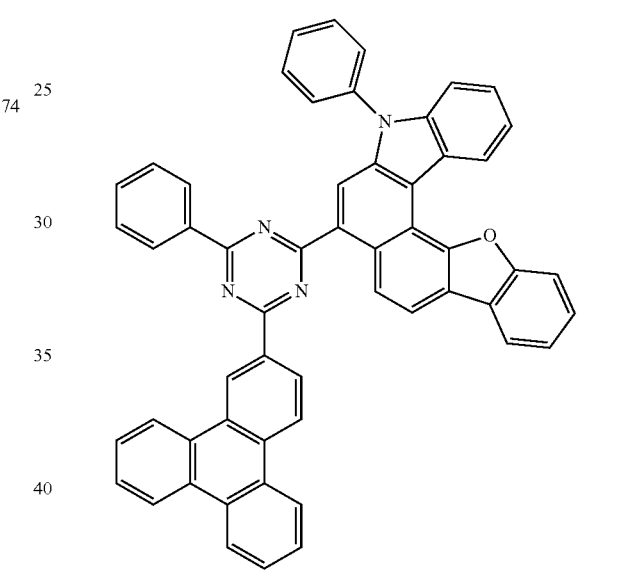
78
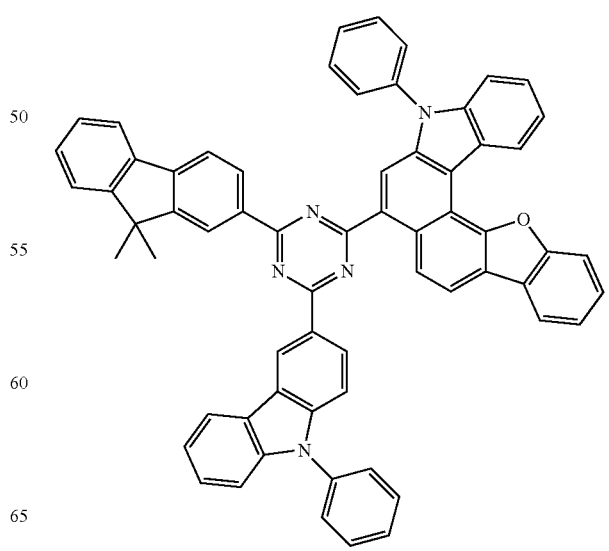

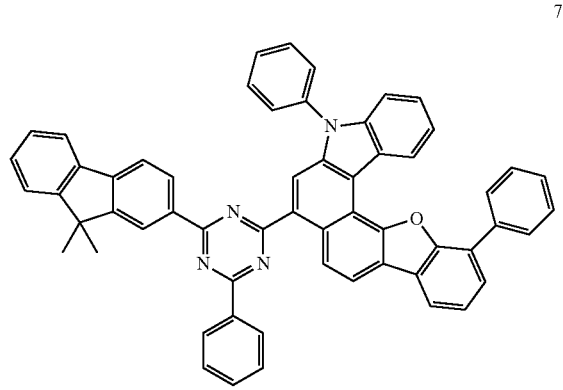
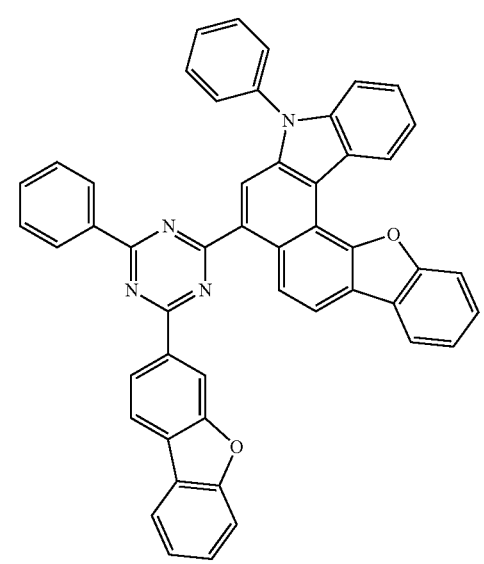
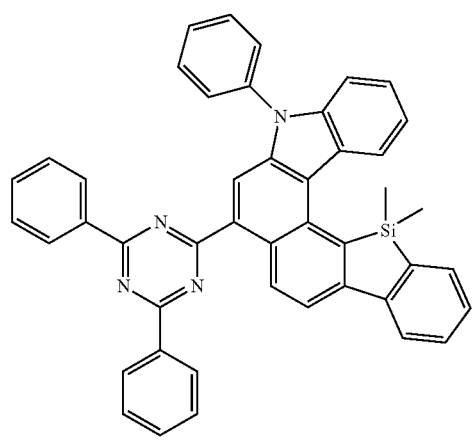
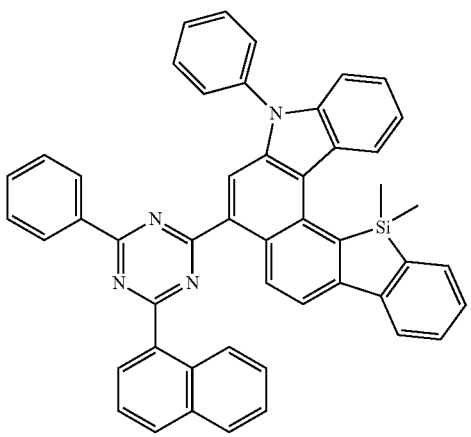
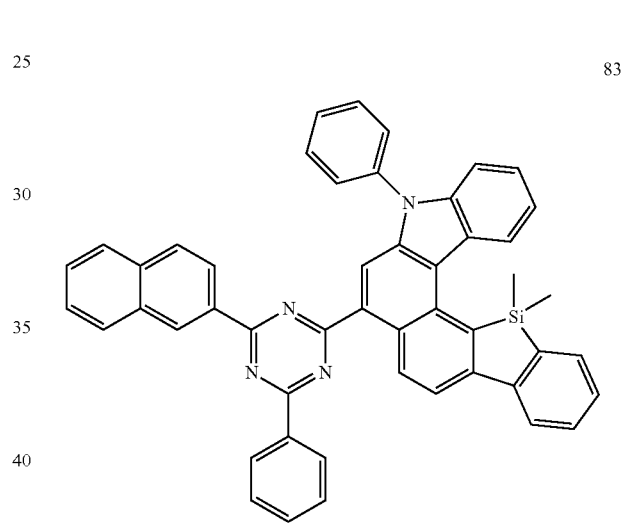
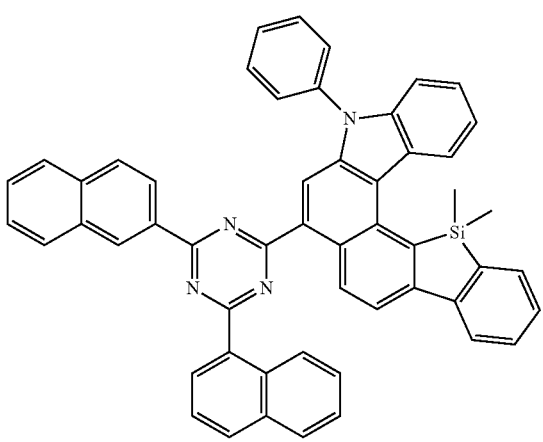

85
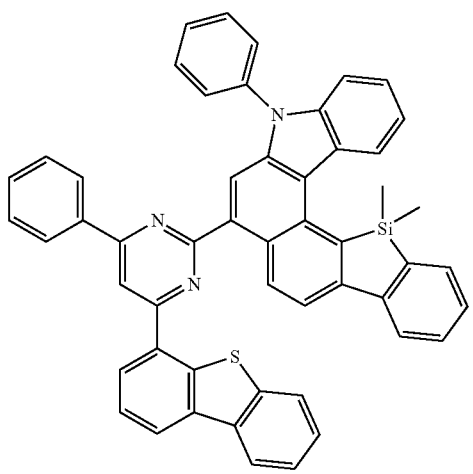
86
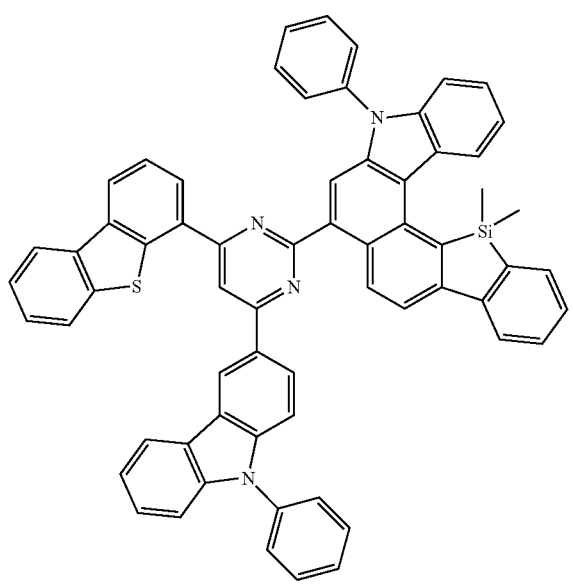
87
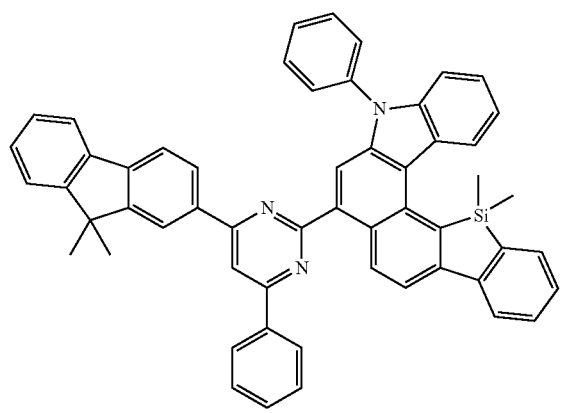
88
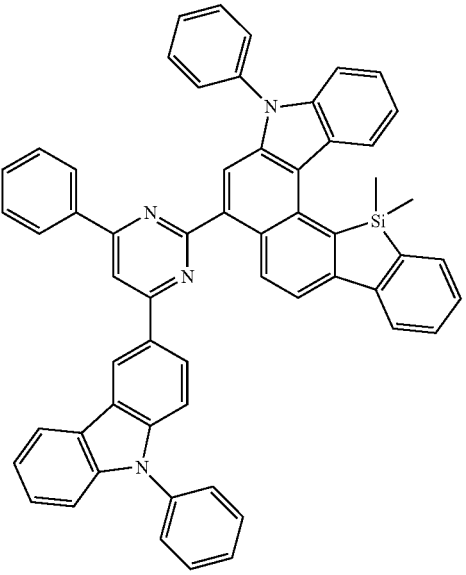
89
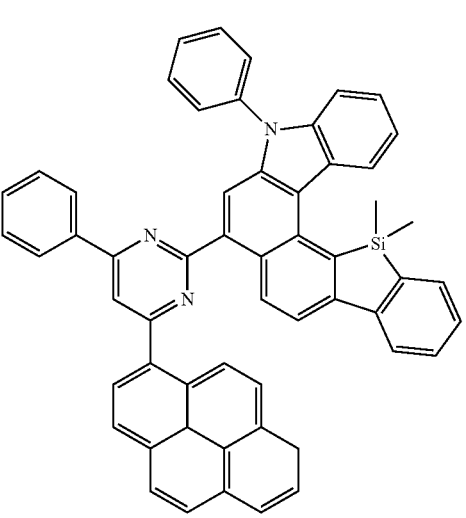
90
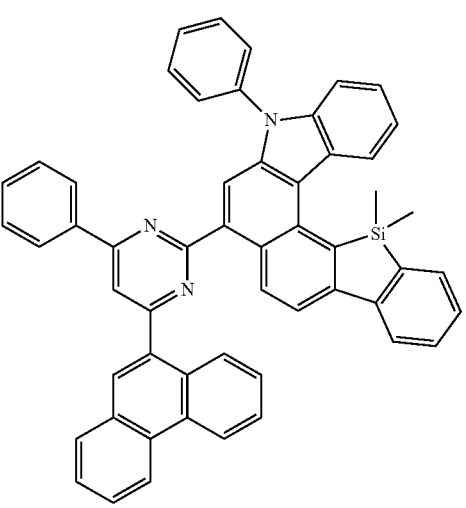

91
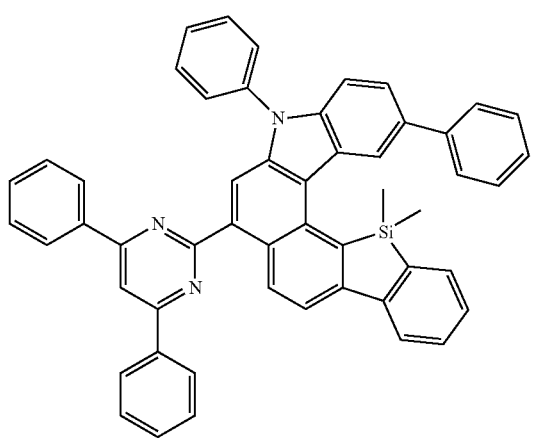
92
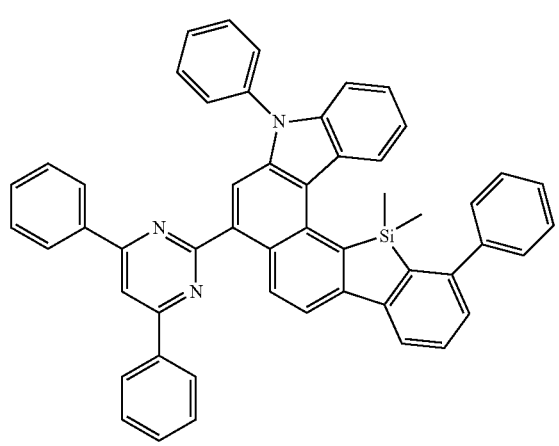
93
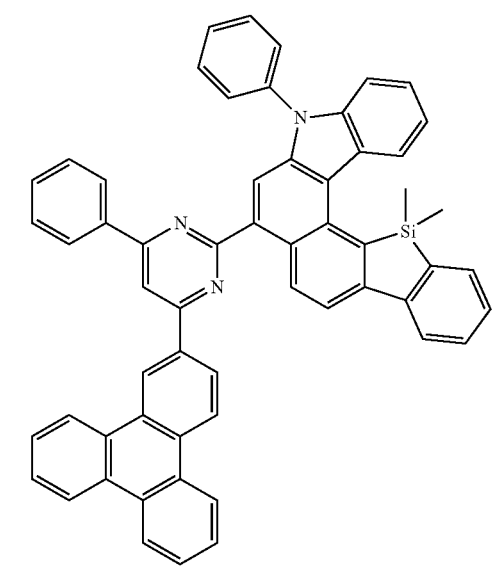
94
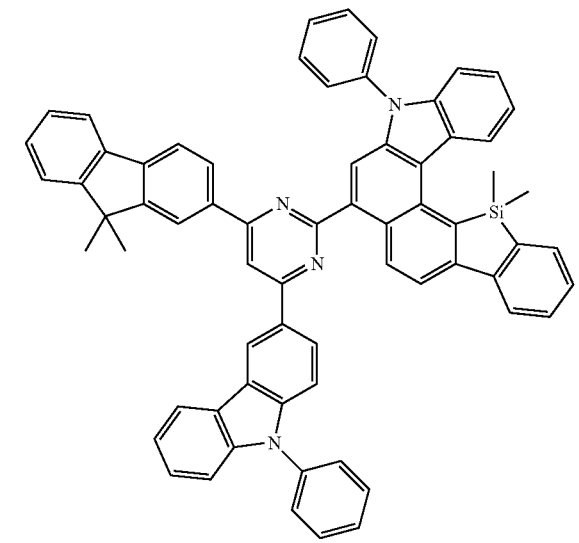
95
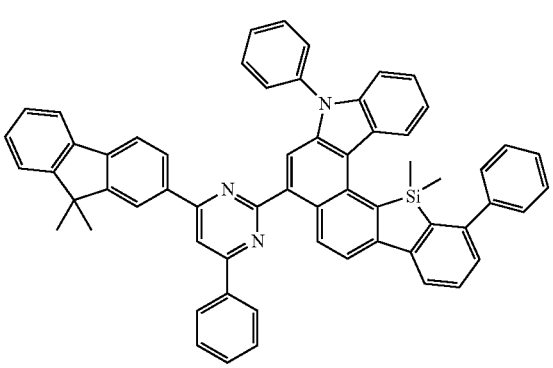
96
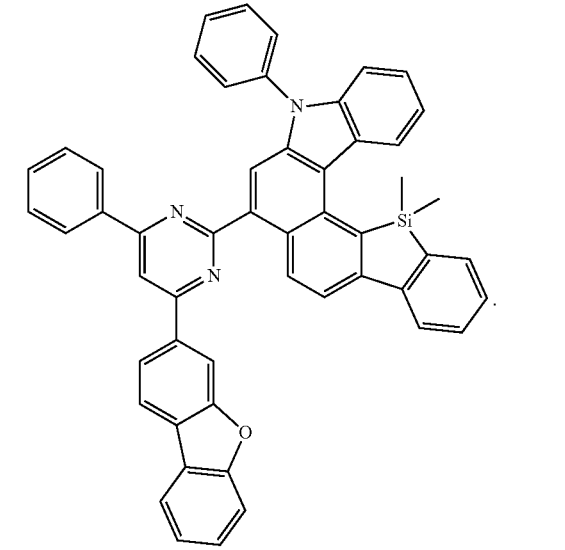
13. An organic light-emitting device comprising a first electrode, a second electrode disposed opposite to the first electrode, and an organic layer disposed between the first electrode and the second electrode, the organic layer comprising the fused ring compound of claim 1.

14. The organic light-emitting device of claim 13, wherein the organic layer comprises at least one of a hole injection layer, a hole transport layer, a functional layer having both hole injection and hole transport capabilities, a buffer layer, an emission layer, a hole blocking layer, an electron transport layer, an electron injection layer, or a functional layer having both electron injection and electron transport capabilities.

15. The organic light-emitting device of claim 13, wherein the organic layer comprises at least one of a hole injection layer, a hole transport layer, or a functional layer having both hole injection and hole transport capabilities, and at least one of the hole injection layer, the hole transport layer, or the functional layer having both hole injection and hole transport capabilities comprises the fused ring compound.

16. The organic light-emitting device of claim 15, wherein at least one of the hole injection layer, the hole transport layer, or the functional layer having both hole injection and hole transport capabilities further comprises a charge-generating material, and the charge-generating material is at least one of a quinine derivative, a metal oxide, or a cyano group-containing compound.

17. The organic light-emitting device of claim 13, wherein the organic layer comprises at least one of an electron injection layer, an electron transport layer, or a functional layer having both electron injection and electron transport capabilities, and at least one of the electron injection layer, the electron transport layer, or the functional layer having both electron injection and electron transport capabilities comprises the fused ring compound.

18. The organic light-emitting device of claim 13, wherein the organic layer comprises an emission layer, and the emission layer comprises the fused ring compound.

19. The organic light-emitting device of claim 18, wherein the fused ring compound serves as a phosphorescent host.

20. The organic light-emitting device of claim 13, wherein the organic layer comprises an emission layer, and at least one of an electron injection layer, an electron transport layer or a functional layer having both electron injection and electron transport capabilities; and the emission layer comprises an arylamine compound.

21. An organic light-emitting display device comprising: a transistor comprising a source, a drain, a gate, and an active layer; and the organic light-emitting device according to claim 13, wherein one of the source or the drain of the transistor is electrically connected to the first electrode of the organic light-emitting device.

* * * * *